US011739366B2

(12) United States Patent
Klimanskaya et al.

(10) Patent No.: US 11,739,366 B2
(45) Date of Patent: Aug. 29, 2023

(54) METHODS FOR DETECTION OF RARE SUBPOPULATIONS OF CELLS AND HIGHLY PURIFIED COMPOSITIONS OF CELLS

(75) Inventors: Irina V. Klimanskaya, Upton, MA (US); Roger Gay, Acton, MA (US)

(73) Assignee: Astellas Institute for Regenerative Medicine, Westborough, MA (US)

( * ) Notice: Subject to any disclaimer, the term of this patent is extended or adjusted under 35 U.S.C. 154(b) by 0 days.

(21) Appl. No.: 13/811,708

(22) PCT Filed: Jul. 25, 2011

(86) PCT No.: PCT/US2011/045232
§ 371 (c)(1),
(2), (4) Date: Jul. 26, 2013

(87) PCT Pub. No.: WO2012/012803
PCT Pub. Date: Jan. 26, 2012

(65) Prior Publication Data
US 2013/0302824 A1    Nov. 14, 2013

Related U.S. Application Data

(60) Provisional application No. 61/414,770, filed on Nov. 17, 2010, provisional application No. 61/367,038, filed on Jul. 23, 2010.

(51) Int. Cl.
G01N 33/53 (2006.01)
C12Q 1/42 (2006.01)
G01N 33/569 (2006.01)
G01N 33/50 (2006.01)

(52) U.S. Cl.
CPC .......... *C12Q 1/42* (2013.01); *G01N 33/5005* (2013.01); *G01N 33/56966* (2013.01)

(58) Field of Classification Search
None
See application file for complete search history.

(56) References Cited

U.S. PATENT DOCUMENTS

| | | | |
|---|---|---|---|
| 6,207,299 B1 | 3/2001 | Krauth et al. | |
| 6,322,901 B1 | 11/2001 | Bawendi et al. | |
| 6,335,205 B1* | 1/2002 | Bausback | 436/514 |
| 6,576,291 B2 | 6/2003 | Bawendi et al. | |
| 6,649,138 B2 | 11/2003 | Adams et al. | |
| 6,682,596 B2 | 1/2004 | Zehunder et al. | |
| 6,800,480 B1 | 10/2004 | Bodnar et al. | |
| 6,815,064 B2 | 11/2004 | Treadway et al. | |
| 7,736,896 B2 | 6/2010 | Klimanskaya et al. | |
| 7,794,704 B2 | 9/2010 | Klimanskaya et al. | |
| 7,795,025 B2 | 9/2010 | Klimanskaya et al. | |
| 8,268,303 B2 | 9/2012 | Klimanskaya et al. | |
| 9,040,038 B2 | 5/2015 | Klimanskaya et al. | |
| 9,040,039 B2 | 5/2015 | Klimanskaya et al. | |
| 9,040,770 B2 | 5/2015 | Klimanskaya et al. | |
| 9,045,732 B2 | 6/2015 | Klimanskaya et al. | |
| 9,080,150 B2 | 7/2015 | Klimanskaya et al. | |
| 9,181,524 B2 | 11/2015 | Klimanskaya et al. | |
| 9,193,950 B2 | 11/2015 | Klimanskaya et al. | |
| 9,562,217 B2 | 2/2017 | Klimanskaya et al. | |
| 9,649,340 B2 | 5/2017 | Klimanskaya et al. | |
| 9,650,607 B2 | 5/2017 | Klimanskaya et al. | |
| 9,730,962 B2 | 8/2017 | Klimanskaya et al. | |
| 10,077,424 B2 | 9/2018 | Malcuit et al. | |
| 10,485,829 B2 | 11/2019 | Malcuit et al. | |
| 2002/0119565 A1 | 8/2002 | Clarke et al. | |
| 2002/0168657 A1* | 11/2002 | Chen et al. | 435/6 |
| 2003/0109420 A1* | 6/2003 | Valkirs | G01N 33/6887 435/7.1 |
| 2004/0037815 A1 | 2/2004 | Clarke et al. | |
| 2004/0133095 A1 | 7/2004 | Dunki-Jacobs et al. | |
| 2005/0012182 A1 | 1/2005 | Jang et al. | |
| 2005/0032126 A1 | 2/2005 | Coombs et al. | |
| 2005/0118713 A1* | 6/2005 | Strelchenko et al. | 435/366 |
| 2005/0164382 A1* | 7/2005 | Xu | C12N 5/0657 435/366 |
| 2006/0051325 A1 | 3/2006 | Clarke et al. | |
| 2006/0073125 A1 | 4/2006 | Clarke et al. | |

(Continued)

FOREIGN PATENT DOCUMENTS

| | | | |
|---|---|---|---|
| JP | 2005-505746 A | 2/2005 | |
| JP | 2008-518616 A | 6/2008 | |

(Continued)

OTHER PUBLICATIONS

Wulff et al., DAKI Flow Cytometry Educational Guide 2nd Edition, 2006, 130 pages.*
Vector Laboratories, Vector Red Substrate, 1 page, 2014 retrieved from https://www.vectorlabs.com/data/protocols/SK-5100.pdf on Mar. 11, 2015.*
Scordato et al., Yellow Excitation: Texas Red HYQ, 2 pages, 2013, retrieved from http://www.microscopyu.com/articles/fluorescence/filtercubes/yellow/texasredhyq/texasredhyqindex.html on Mar. 11, 2015.*
Invitation to Pay Additional Fees for Application No. PCT/US2011/045232 dated Mar. 30, 2012.

(Continued)

*Primary Examiner* — Gary Counts
(74) *Attorney, Agent, or Firm* — Wolf, Greenfield & Sacks, P.C.

(57) ABSTRACT

Methods are provided for detection of a target cell type within a cell population, and compositions are provided comprising cells and an indicator that indicates the number of cells of the target cell type in the cell population. Examples are provided in which these methods are used to detect human embryonic stem cells within a differentiated cell population with exquisite sensitivity. Differentiated cells produced from embryonic stem cells can be characterized by these methods before transplantation into a recipient, thereby providing further assurance of safety.

22 Claims, 4 Drawing Sheets

(56) References Cited

U.S. PATENT DOCUMENTS

| | | | |
|---|---|---|---|
| 2007/0061910 A1* | 3/2007 | Han et al. | 800/19 |
| 2007/0160974 A1 | 7/2007 | Sidhu et al. | |
| 2007/0190647 A1 | 8/2007 | Clarke et al. | |
| 2007/0212737 A1 | 9/2007 | Clarke et al. | |
| 2007/0231325 A1 | 10/2007 | Clarke et al. | |
| 2007/0259969 A1 | 11/2007 | Clarke et al. | |
| 2007/0297983 A1 | 12/2007 | Ferrone et al. | |
| 2008/0057041 A1* | 3/2008 | Chung et al. | 424/93.7 |
| 2008/0064049 A1 | 3/2008 | Clarke et al. | |
| 2008/0064099 A1 | 3/2008 | Parikh et al. | |
| 2008/0175870 A1 | 7/2008 | Mather et al. | |
| 2008/0178305 A1 | 7/2008 | Clarke et al. | |
| 2008/0194022 A1 | 8/2008 | Clarke et al. | |
| 2008/0200369 A1* | 8/2008 | Fukuda | 514/2 |
| 2009/0004205 A1 | 1/2009 | Clarke et al. | |
| 2009/0123439 A1* | 5/2009 | Yun | C12Q 1/6886 424/93.21 |
| 2009/0233324 A1 | 9/2009 | Kopf-Sill | |
| 2009/0275128 A1 | 11/2009 | Thomson et al. | |
| 2010/0105100 A1 | 4/2010 | Sakurada et al. | |
| 2010/0169990 A1 | 7/2010 | Clarke et al. | |
| 2011/0117062 A1 | 5/2011 | Klimanskaya et al. | |
| 2011/0274662 A1 | 11/2011 | Malcuit et al. | |
| 2012/0258451 A1 | 10/2012 | Klimanskaya | |
| 2013/0149284 A1 | 6/2013 | Malcuit et al. | |
| 2013/0195806 A1 | 8/2013 | Gay et al. | |
| 2013/0302286 A1 | 11/2013 | Klimanskaya et al. | |
| 2013/0302426 A1 | 11/2013 | Klimanskaya et al. | |
| 2013/0302824 A1 | 11/2013 | Klimanskaya et al. | |
| 2015/0086512 A1 | 3/2015 | Malcuit et al. | |
| 2015/0328261 A1 | 11/2015 | Klimanskaya et al. | |
| 2015/0366915 A1 | 12/2015 | Gay et al. | |
| 2018/0023052 A1 | 1/2018 | Klimanskaya et al. | |
| 2018/0052150 A1 | 2/2018 | Klimanskaya et al. | |
| 2018/0064761 A1 | 3/2018 | Klimanskaya et al. | |
| 2019/0062703 A1 | 2/2019 | Malcuit et al. | |
| 2019/0282622 A1 | 9/2019 | Klimanskaya et al. | |
| 2020/0113938 A1 | 4/2020 | Malcuit et al. | |
| 2020/0405767 A1 | 12/2020 | Gay et al. | |
| 2021/0060062 A9 | 3/2021 | Malcuit et al. | |
| 2021/0102164 A1 | 4/2021 | Klimanskaya | |
| 2021/0308187 A1 | 10/2021 | Klimanskaya et al. | |
| 2022/0049217 A1 | 2/2022 | Malcuit et al. | |

FOREIGN PATENT DOCUMENTS

| | | | |
|---|---|---|---|
| JP | 2010-500878 A | 1/2010 | |
| JP | 2010-524457 A | 7/2010 | |
| WO | WO 1999/045094 | 9/1999 | |
| WO | WO 01/51616 A2 | 7/2001 | |
| WO | WO 02/062201 A2 | 8/2002 | |
| WO | WO 2005/001889 A2 | 1/2005 | |
| WO | WO 2006/052646 A2 | 5/2006 | |
| WO | WO 2006080952 A2 * | 8/2006 | A61K 35/12 |
| WO | WO 2007085210 A2 * | 8/2007 | C12N 5/06 |
| WO | WO 2008/020675 A1 | 2/2008 | |
| WO | WO 2008/129554 A1 | 10/2008 | |
| WO | WO 2009/050657 | 4/2009 | |
| WO | WO 2009/051671 A1 | 4/2009 | |
| WO | WO 2011/063005 A2 | 5/2011 | |
| WO | WO 2012/012803 A2 | 1/2012 | |

OTHER PUBLICATIONS

International Search Report and Written Opinion for Application No. PCT/US2011/045232 dated Sep. 3, 2012.
International Preliminary Report on Patentability for Application No. PCT/US2011/045232 dated Jan. 31, 2013.
Extended European Search Report dated Nov. 4, 2013 in connection with application No. EP 11810518.8.
Afshari et al., Integrin activation or alpha 9 expression allows retinal pigmented epithelial cell adhesion on Bruch's membrane in wet age-related macular degeneration. Brain. Feb. 2010;133(Pt 2):448-64. doi:10.1093/brain/awp319.
Amit et al., Feeder layer- and serum-free culture of human embryonic stem cells. Biol Reprod. Mar. 2004;70(3):837-45. Epub Nov. 19, 2003.
Carpenter et al., Properties of four human embryonic stem cell lines maintained in a feeder-free culture system. Dev Dyn. Feb. 2004;229(2):243-58.
Emre et al., A Comparative Analysis of Human Embryonic Stem Cells Cultured in a Variety of Media Conditions. Jan. 1, 2008. 8 Pages. http://www.millipore.com/publications.nsf/a73664f9f981af8c852569b9005b4eee/73159860d3320b8a85257501006111a0/$FILE/an1237en00.pdf [last accessed Dec. 10, 2013].
Faustino et al., Automatic Embryonic Stem Cells Detection and Counting Method in Fluorescence Microscopy Images. Monografias em Ciência da Computação. Feb. 1, 2009; p. 1-22.
Haupt et al., Automated selection and collection of pluripotent stem cell colonies using the CellCelector™: Automated collection of hESC colonies. Nature Methods. Jun. 2009; 6(6):iii-iv. http://www.nature.com/nmeth/journal/v6/n6/pdf/nmeth.f.252.pdf [last accessed Dec. 10, 2013].
Holgate et al., Immunogold-silver staining: new method of immunostaining with enhanced sensitivity. J Histochem Cytochem. Jul. 1983;31(7):938-44.
Idelson, Directed differentiation of human embryonic stem cells into functional retinal pigment epithelium cells. Cell Stem Cell. Oct. 2, 2009;5(4):396-408. doi: 10.1016/j.stem.2009.07.002.
Klimanskaya et al., "Derivation and comparative assessment of retinal pigment epithelium from human embryonic stem cells using transcriptomics." Cloning and Stem Cells 6:3, 217-245 2004.
Lu et al., Long-term safety and function of RPE from human embryonic stem cells in preclinical models of macular degeneration. Stem Cells. Sep. 2009;27(9):2126-35. doi: 10.1002/stem.149.
Qu et al., Alternative Routes toward High Quality CdSe Nanocrystals. Nano Lett. Jun. 13, 2001;1(6):333-7. Abstract Only.
Rosler et al., Long-term culture of human embryonic stem cells in feeder-free conditions. Dev Dyn. Feb. 2004;229(2):259-74.
Sheridan et al., Expansion of Human Embryonic Stem Cells by Membrane Based Co-Culture. Jan. 1, 2007. Poster. 1 Page. http://www.millipore.com/publications.nsf/a7366419f981af8c852569b9005b4eee/b08ebcd4e43a4a25852575050063cd4c/$FILE/ps1230en00.pdf [last accessed Dec. 10, 2013].
Wang et al., Transplantation of reprogrammed embryonic stem cells improves visual function in a mouse model for retinitis pigmentosa. Transplantation. Apr. 27, 2010;89(8):911-9. doi: 10.1097/TP.0b013e3181d45a61.
Xu et al., Feeder-free growth of undifferentiated human embryonic stem cells. Nat Biotechnol. Oct. 2001;19(10):971-4. Abstract Only.
PCT/US2011/045232, Mar. 30, 2012, Invitation to Pay Additional Fees.
PCT/US2011/045232, Sep. 3, 2012, International Search Report and Written Opinion.
PCT/US2011/045232, Jan. 31, 2013, International Preliminary Report on Patentability.
EP 11810518.8, Nov. 4, 2013, Extended European Search Report.
Hayashi et al., Integrins regulate mouse embryonic stem cell self-renewal. Stem Cells. Dec. 2007;25(12):3005-15. Epub Aug. 23, 2007.
Karlsson et al., Human embryonic stem cell-derived mesenchymal progenitors—potential in regenerative medicine. Stem Cell Res. Jul. 2009;3(1):39-50. doi: 10.1016/j.scr.2009.05.002. Epub May 19, 2009.
Levenberg et al., Differentiation of human embryonic stem cells on three-dimensional polymer scaffolds. Proc Natl Acad Sci U S A. Oct. 28, 2003;100(22):12741-6. Epub Oct. 15, 2003.
Ma et al., Cell-extracellular matrix interactions regulate neural differentiation of human embryonic stem cells. BMC Dev Biol. Sep. 22, 2008;8:90. doi: 10.1186/1471-213X-8-90.
Uemura et al., Matrigel supports survival and neuronal differentiation of grafted embryonic stem cell-derived neural precursor cells. J Neurosci Res. Feb. 15, 2010;88(3):542-51. doi: 10.1002/jnr.22223.

(56) References Cited

OTHER PUBLICATIONS

Zhou et al., Embryoid bodies formation and differentiation from mouse embryonic stem cells in collagen/Matrigel scaffolds. J Genet Genomics. Jul. 2010;37(7):451-60. doi: 10.1016/S1673-8527(09)60064-3.
Extended European Search Report for Application No. 21163768.1, dated Aug. 11, 2021.
Kuroda et al., Highly sensitive in vitro methods for detection of residual undifferentiated cells in retinal pigment epithelial cells derived from human iPS cells. PLoS One. 2012;7(5):e37342. doi: 10.1371/journal.pone.0037342. Epub May 17, 2012.
U.S. Appl. No. 16/113,717, filed Aug. 27, 2018, Malcuit et al.

* cited by examiner

METHODS FOR DETECTION OF RARE SUBPOPULATIONS OF CELLS AND HIGHLY PURIFIED COMPOSITIONS OF CELLS

RELATED APPLICATION DISCLOSURE

This patent application is a national stage of International Patent Application No. PCT/US2011/045232, which claims the benefit of U.S. Provisional Application No. 61/367,038, filed Jul. 23, 2010 and U.S. Provisional Application No. 61/414,770, filed Nov. 17, 2010, each of which is incorporated by reference herein in its entirety.

BACKGROUND

Therapeutic use of stem cells has a profound potential to revolutionize medical treatment. Researchers have long hoped to use embryonic stem cells and other pluripotent cell types as a source of cells for therapeutic transplantation. For example, embryonic stem cells may be differentiated into retinal pigment epithelium cells and transplanted into patients for the prevention or treatment of retinal disease, as disclosed in U.S. Pat. Nos. 7,795,025, 7,794,704, and 7,736,896, U.S. Ser. No. 12/682,712, U.S. Provisional Applications 60/998,668, 60/998,766, 61/009,911, 61/009,908, and 61/262,002, WO/2009/051671, and WO 2011/063005, each of which is incorporated by reference herein in its entirety.

However, the self-renewal capability and plasticity of stem cells—the very attributes that confer such therapeutic promise—also lead to safety concerns. A dramatic illustration of the potential dangers of using stem cells without adequate safety testing was the recent case of a "stem cell tourist" who reportedly received stem cell injections into her kidneys at a private clinic in Thailand (a treatment that was apparently untested and had not been approved by any regulatory agency). The patient did not receive any evident therapeutic benefit from the treatment but instead developed masses at the sites of injection, necessitating removal of the kidney (Thirabanjasak et al., "Angiomyeloproliferative Lesions Following Autologous Stem Cell Therapy," J Am Soc Nephrol. 2010 Jun. 17). The authors of this study concluded that the masses arose from the transplanted stem cells. This incident was widely reported in the popular press as a sobering reminder that "sick people should not gamble with their safety, and money, by turning to stem-cell tourism peddled by unscrupulous operators" (Coghlan, "Death revives warnings about rogue stem cell clinics," The New Scientist, 17 Jun. 2010).

Even in a treatment regimen using differentiated cell types derived from ES cells, there is concern that presence of a few residual ES cells could give rise to a tumor or teratoma. Some assurance of safety can come from administering the cell preparation to an animal (e.g., an immune compromised animal). However, animal testing alone may be considered insufficient because a human ES cell may be more prone to produce a teratoma in a human host than in the animal model.

One complementary approach to address these potential safety concerns is genetically engineering stem cells to express an inducible "suicide gene." The hope of these methods is that the stem cells and their progeny can be selectively killed in the event of unregulated growth (see, e.g., Schuldiner et al., "Selective ablation of human embryonic stem cells expressing a 'suicide' gene," Stem Cells, 2003; 21(3):257-65). However, depending on the disease involved and location and amount of stem cell-derived tissue, inducing death of the transplanted cells might cause great harm to a patient. Moreover, in the case of patient-specific cell therapies, use of this type of safety mechanism would require potentially very labor-intensive genetic engineering of patient-specific cells, along with testing each patient-specific cell line for safety, efficacy, and absence of undesired genetic modifications. Even though inducible suicide genes could provide treatment options once a tumor or teratoma begins to arise, it is clearly preferable to avoid tumor or teratoma formation entirely. Additionally, the cells could become resistant to induction of the suicide gene, for example by mutation or loss of the suicide gene, rendering the suicide gene ineffective and allowing the cells to remain potentially harmful. Thus, methods of directly detecting stem cells in a cell population are also desired to provide assurance that undifferentiated stem cells are at most present at a very low concentration or preferably entirely absent.

Conventional methods of detecting stem cells have limited sensitivity which may not provide sufficient assurance of the absence of stem cells. For methods utilizing bulk cell extracts (such as RT-PCR and Western blotting), sensitivity can be inherently limited by background expression of stem cell genes in non-stem cells. For example, if a stem cell gene is expressed at 1000-fold lower concentrations in non-stem cells, a bulk cell extract having a stem cell concentration below 1 in 1000 cells will have a less than 2-fold increase in that gene product, which is below the noise threshold for many conventional detection methods. If a therapeutic regimen involves administering 500,000 cells, such a method would be unable to detect as many as 500 residual stem cells in the cell preparation. This number of stem cells would likely be considered to be unsafe due to the potential for teratoma formation. Thus, these methods are most useful when the desired sensitivity of detection is no greater than the fold-difference in stem cell gene expression between stem cells and other cells in the population. Due to this insensitivity, such methods would likely be considered inadequate to assure patient safety.

Another convention method of detecting stem cells, flow cytometry, can have somewhat greater sensitivity than RT-PCR for detection of stem cells because individual cells are considered rather than bulk extracts. However, preparation of cells for flow cytometry involves steps that result in loss of cells, such as cell permeabilization, washing, and sieving cells to ensure a single cell suspension. Due to this cell loss, there is concern whether the subpopulation of cells that reach the flow cytometer are truly representative of the initial population of cells. For example, because stem cells may have a tendency be relatively "sticky" compared to other cell types, they may be preferentially lost at the cell sieving stage. Moreover, due to their small size, small clumps of stem cells may pass through a sieve together and be miscounted as a single event in the flow cytometer, leading to undercounting of stem cells in the preparation. Furthermore, with flow cytometry assays, gating of the cell population is typically required to exclude cell debris, cell aggregates, and non-specific background "noise". Even if ungated cells are evaluated, the interpretation of the results (as far as where to "draw a line" for positive/negative cells) may rely on an operator's subjective opinion, and while large quantities of contaminating cells in a population can be easily detected by flow cytometry, small numbers of cells would almost certainly fall into the "noise" category even though they may be sufficiently numerous to present potential safety concerns. Thus, due to the potential to lose or fail to fully count stem cells, flow cytometry methods may also have insufficient sensitivity to assure patient safety.

Thus, there is a need in the art for highly sensitive methods of detecting the presence of undifferentiated cells in a cell composition and for stem cell-derived compositions that are verified to be free of undifferentiated stem cells. Preferred methods are sufficiently sensitive to detect stem cells even in concentrations as low as 1 per 100,000 cells or lower, and moreover permit testing of every cell in a population without loss of a substantial fraction of cells during assay preparation.

SUMMARY

This disclosure provides assay methods for sensitive detection of cells of a target type within a larger population of cells of other types. In a preferred embodiment the target cells will comprise rare cells, i.e., cells which are present in very minute amounts in a cell population, preferably which cell population is to be used for cell therapy. In a particularly preferred embodiment these rare cells will comprise cells which if administered to a subject could cause an adverse reaction or disease. Specific examples include virally infected (e.g., HIV, hepatitis, et al.) cells, other diseased or aberrant cells (such as cancerous, precancerous and cancer stem cells), certain immune cells such as T lymphocytes, and the like which if administered to a recipient, could result in infection, disease, or other adverse reaction such as an adverse immune reaction (e.g., GVHD), or result in the proliferation of undesired cells. For example, the subject methods may be used to confirm that a donor cell containing population, such as bone marrow or pancreatic cells derived from an autologous or heterologous donor, which is to be used in cell therapy or transplant is devoid of cells that may cause cancer, viral infection, or an adverse immune reaction. In a preferred exemplified embodiment examples are provided using these methods to test for the presence of residual pluripotent cells in a population of cells to be used for transplantation therapy. Experiments in which defined numbers of ES cells were added to the cell population demonstrate sufficient sensitivity to detect as few as 5 ES cells out of a population of 600,000 cells, thus showing the capability to detect target cells as rare as 0.0008% of the total cell population. Using an exemplary embodiment of these methods, a trained operator can examine on the order of between one and ten million cells per hour. Because arbitrarily large numbers of cells can be examined, the method has the potential to have unlimited sensitivity.

In one exemplary embodiment, the present disclosure provides a method of detecting the presence of target cells in a cell population, comprising:

(a) providing a cell population;

(b) applying a first stain and a second stain to said cell population, wherein said first stain detects a first marker that is indicative of target cells and said second stain detects a second marker that is indicative of target cells, and wherein cells that are positive for said first stain are detectable under visible light and cells that are positive for said second stain are detectable under ultraviolet light;

(c) microscopically observing cells of said cell population under visible light to detect cells that are positive for said first marker;

(e) microscopically observing said cells that are positive for said first marker under ultraviolet light and determining whether a cell is positive for said first marker and said second marker; and (f) identifying a cell that is positive for said first marker and said second marker as a target cell.

The first stain may be observable under visible light and under ultraviolet light.

The first marker may be alkaline phosphatase.

The first stain may comprise an antibody directly or indirectly coupled to a colored reagent or an enzyme capable of producing a colored reagent.

The colored reagent may comprise gold particles, silver particles, or latex particles.

The first stain may comprise an antibody directly or indirectly coupled to gold particles and said method may further comprise forming a silver precipitate on said gold particles.

The first marker may be selected from the group consisting of: alkaline phosphatase, Oct-4, Nanog, Stage-specific embryonic antigen-3 (SSEA-3), Stage-specific embryonic antigen-4 (SSEA-4), TRA-1-60, TRA-1-81, TRA-2-49/6E, Sox2, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (hTERT), SALL4, E-CADHERIN, Cluster designation 30 (CD30), Cripto (TDGF-1), GCTM-2, Genesis, Germ cell nuclear factor, and Stem cell factor (SCF or c-Kit ligand).

The first stain may comprise a first enzyme selected from the group consisting of: alkaline phosphatase, beta galactosidase, and peroxidase.

The peroxidase may be horseradish peroxidase.

The first enzyme may be expressed by target cells.

The first enzyme may be directly or indirectly coupled to a primary or secondary antibody.

The first stain may comprise alkaline phosphatase.

The first stain may further comprise an alkaline phosphatase substrate selected from the group consisting of: napthol AS-BI phosphate; 5-bromo-4-chloro-3-indolyl phosphate (BCIP) and Nitro Blue Tetrazolium (NBT); BCIP reagent and INTX reagent; naphthol AS-BI and fast red violet LB; tetrazolium salts; diazo compounds; VECTOR® Red; VECTOR® Blue; VECTOR® Black; and p-Nitrophenylphosphate (pNPP).

The first stain may comprise peroxidase.

The first stain may further comprise a peroxidase substrate selected from the group consisting of: 3,3',5,5'-Tetramethylbenzidine (TMB); 3,3'-Diaminobenzidine (DAB); 3-Amino-9-EthylCarbazole (AEC); 4-Chloro-1-naphthol; 2,2'-azino-bis(3-ethylbenzthiazoline-6-sulphonic acid) (ABTS); 2,3,5-Triphenyltetrazolium chloride; 2-Chloro-5,5-dimethyl-1,3-cyclohexanedione; 3,3',5,5'-Tetramethylbenzidine; 3,3'-Diaminobenzidine tetrahydrochloride; 3-Nitrotetrazolium blue chloride; 4-Aminophthalhydrazide; 4-Chloro-1-naphthol; 4-Chloro-7-nitrobenzofurazan; 5-Aminosalicylic acid; Dicarboxidine dihydrochloride; Guaiacol; Hydrogen peroxide-Urea adduct; Iodonitrotetrazolium chloride; Luminol; MTT Formazan; N-(4-Aminobutyl)-N-ethylisoluminol; N-(6-Aminohexyl)-N-ethylisoluminol; Nitrotetrazolium Blue chloride; Pyrogallol; Tetranitroblue tetrazolium chloride; Tetrazolium Blue Chloride indicator; Tetrazolium Violet; o-Dianisidine; o-Dianisidine dihydrochloride; o-Phenylenediamine dihydrochloride; o-Phenylenediamine free base; and trans-5-Phenyl-4-pentenyl hydroperoxide.

The first stain may comprise beta galactosidase.

The first stain may further comprise a beta galactosidase substrate selected from the group consisting of: 1-Methyl-3-indolyl-β-D-galactopyranoside; 2-Nitrophenyl β-D-galactopyranoside; 4-Methylumbelliferyl β-D-galactopyranoside; 4-Nitrophenyl β-D-galactopyranoside; 5-Bromo-3-indolyl β-D-galactopyranoside; 5-Bromo-4-chloro-3-indolyl β-D-galactopyranoside; 5-Bromo-6-chloro-3-indolyl-β-D-galactopyranoside; 6-Bromo-2-naphthyl β-D-galactopyranoside; 6-Chloro-3-indolyl-β-D-galactopyranoside; Fluorescein di(β-D-galactopyranoside); and Resorufin β-D-galactopyranoside.

The target cell may be an embryonic stem cell and said second marker may be selected from the group consisting of: alkaline phosphatase, Oct-4, Nanog, Stage-specific embryonic antigen-3 (SSEA-3), Stage-specific embryonic antigen-4 (SSEA-4), TRA-1-60, TRA-1-81, TRA-2-49/6E, Sox2, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (hTERT), SALL4, E-CADHERIN, Cluster designation 30 (CD30), Cripto (TDGF-1), GCTM-2, Genesis, Germ cell nuclear factor, and Stem cell factor (SCF or c-Kit ligand).

The second stain may comprise a primary antibody, which may comprise a fluorescent label.

The second stain may further comprise a secondary antibody, which may comprise a fluorescent label.

The fluorescent label may be selected from the group consisting of: ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 594, ALEXA FLUOR® 610, ALEXA FLUOR® 633, ALEXA FLUOR® 635, ALEXA FLUOR® 647, ALEXA FLUOR® 660, ALEXA FLUOR® 680, ALEXA FLUOR® 700, ALEXA FLUOR® 750 and ALEXA FLUOR® 790, fluorescein isothiocyanate (FITC), TEXAS RED® (sulforhodamine 101 acid chloride), SYBR® Green, DYLIGHT® Fluors, green fluorescent protein (GFP), TRIT (tetramethyl rhodamine isothiol), NBD (7-nitroben-2-oxa-1,3-diazole), TEXAS RED® (sulforhodamine 101 acid chloride) dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, TET (6-carboxy-2',4,7,7'-tetrachlorofluorescein), HEX 6-carboxy-2',4,4',5',7,7-hexachlorofluorescein), Joe {6-carboxy-4',5'-dichloro-2',7'-dimethoxyfluorescein} 5-carboxy-2',4',5', 7'-tetrachlorofluorescein, 5-carboxyfluorescein, 5-carboxy rhodamine, Tamra (tetramethylrhodamine), 6-carboxyrhodamine, Rox (carboxy-X-rhodamine), R6G (Rhodamine 6G), phthalocyanines, azomethines, cyanines (e.g. Cy3, Cy3.5, Cy5), xanthines, succinylfluoresciens, N, N-diethyl-4-(5'-azobenzotriazolyl)-phenylamine, aminoacridine, and quantum dots.

The cell population may comprise cells of a species selected from the group consisting of: antelopes, bovines, camels, cats, chevrotains (mouse deer), chimpanzee, cow, deer, dog, giraffes, goat, guinea pig, hamster, hippopotamuses, horse, human, mouse, non-human primate, ovine, peccaries, pig, pronghorn, rabbit, rat, rhesus macaque, rhinoceroses, sheep, tapirs, and ungulates.

The method may further comprise determining the approximate number of cells in the cell population.

At least 90% of the cells in said cell population may be examined under visible light to detect cells that are positive for said first marker, and each cell that is positive for said first marker may be examined under ultraviolet light to determine whether that cell is positive for said second marker.

The cell population may contain any number of cells, depending on the intended use. For example, a cell population may contain at least $10^5$ cells, at least $10^6$ cells, at least $10^7$ cells, at least $10^8$ cells, at least $10^9$ cells, at least $10^{10}$ cells, or between $10^5$ and $10^{10}$ cells.

The first marker and second marker may be embryonic stem cell markers.

The population of cells may be produced by in vivo or in vitro differentiation of embryonic stem cells.

The target cell may be an embryonic stem cell or induced pluripotent (iPS) cell.

The cell population may further comprise cells differentiated from an embryonic stem cell or iPS cell.

The cells differentiated from an embryonic stem cell or iPS cell may be RPE cells. For example, the RPE cells may be produced by any of the methods disclosed in U.S. Pat. Nos. 7,795,025, 7,794,704, and 7,736,896, U.S. Ser. No. 12/682,712, WO/2009/051671, and WO 2011/063005, each of which is incorporated by reference herein in its entirety.

The target cell may be selected from specific types of cells including by way of example: adipocyte; bone marrow fibroblast; cardiomyocyte; chondrocyte; differentiated RBC and WBC lineages; endothelial bone marrow fibroblasts; ectoderm; ectoderm progenitor; embryoid body (EB); embryonal carcinoma (EC); embryonic stem (ES); endoderm; endothelial; hematopoietic cells; hematopoietic stem cell (HSC), satellite, endothelial progenitor; hepatocyte; keratinocyte; mesenchymal; mesenchymal stem cell (MSC); mesoderm; MSC progenitor; myoblast; myocyte; neural progenitor; neural stem cell; neuron; oligodendrocyte; osteoblast; pancreatic epithelium; pancreatic islet; pancreatic progenitor; skeletal myocyte; smooth muscle; stromal (mesenchymal) precursor cells; and white blood cell (WBC). The first marker and the second marker may be markers associated with said target cell as listed in Table 1. In addition the target cell may comprise a cell involved in a specific disease, e.g., a cancerous or precancerous cell or a cancer stem cell which is desirably eliminated from a cell population potentially for transplant or cell therapy such as bone marrow. Alternatively the target cell may comprise an adult stem cell that gives rise to cells of a specific lineage.

The method may further comprise prior to step (a) culturing the cell population under conditions that favor maintenance cells of the target cell type, and the target cell may be an embryonic stem cell or induced pluripotent (iPS) cell, and the culture conditions may comprise embryonic stem cell media and/or the presence of mouse embryonic fibroblast feeder cells.

The method may further comprise plating a second cell population comprising the target cell type and analyzing said second cell population by the same method as said cell population of step (a), thereby establishing the limit of detection of said method. Only cells of said target cell type are added to said second population, or the second cell population may comprise a mixture of a first group of cells and a second group of cells, wherein the first group of cells is of the same type as the target cell type. The second group of cells may have essentially the same constituency as said cell population of step (a). The ratio of the number of cells in said first group of cells and said second group of cells may be selected from the group consisting of: 1:10; 1:100; 1:1,000; 1:10,000; 1:100,000; 1:1,000,000; 1:10,000,000; 1:100,000,000; 1:1,000,000,000; between 1:10 and 1:100; between 1:10 and 1:1,000; between 1:10 and 1:10,000; between 1:10 and 1:100,000; between 1:10 and 1:1,000,000; between 1:10 and 1:10,000,000; between 1:10 and 1:100, 000,000; between 1:10 and 1:1,000,000,000; between 1:100 and 1:1,000; between 1:100 and 1:10,000; between 1:100 and 1:100,000; between 1:100 and 1:1,000,000; between 1:100 and 1:10,000,000; between 1:100 and 1:100,000,000; between 1:100 and 1:1,000,000,000; between 1:1,000 and 1:10,000; between 1:1,000 and 1:100,000; between 1:1,000 and 1:1,000,000; between 1:1,000 and 1:10,000,000; between 1:1,000 and 1:100,000,000; between 1:1,000 and 1:1,000,000,000; between 1:10,000 and 1:100,000; between 1:10,000 and 1:1,000,000; between 1:10,000 and 1:10,000,000; between 1:10,000 and 1:100,000,000; between 1:10,000 and 1:1,000,000,000; between 1:100,000 and 1:1,000.000; between 1:100,000 and 1:10,000,000; between 1:100,000 and 1:100,000,000; between 1:100,000 and 1:1,000,000.000; between 1:1,000.000 and 1:10,000,000; between 1:1,000.000 and 1:100,000,000; between 1:1,000,000 and 1:1,000,000,000; between 1:10,000,000 and 1:100,000,000; between 1:10,000,000 and 1:1,000,000,000; and between 1:100,000,000 and 1:1,000,000,000.

The target cell may be selected from a virally infected cell, cancerous or precancerous cell, cancer stem cell, and an immune cell.

The cell population putatively containing the target cell may comprise bone marrow, blood cells, or pancreatic cells.

The cell population putatively containing the target cell may have previously been treated by cell sorting, irradiation, chemotherapy or another means to remove the target cell.

Another exemplary embodiment provides a composition comprising somatic cells derived from stem cells that may be essentially free of said stem cells.

Another exemplary embodiment provides a composition comprising cells and an indicator that indicates the number or fraction of target cells (such as stem cells) present, wherein the value of said indicator may be determined by applying the methods described herein to a cell population representative of the cells in said composition. The composition may comprise RPE cells, which may be differentiated from pluripotent stem cells, such as embryonic stem cells, iPS cells, blastomeres, inner mass cells, or oocytes which may be parthenogenetically activated. These pluripotent stem cells may be recombinant or genetically engineered (e.g., engineered to express a desired therapeutic protein or to eliminate the expression of a gene involved in a genetic deficiency such as macular degeneration.) The RPE cells may be formulated and used to treat retinal degenerative diseases. Additionally, pluripotent stem cell-derived RPE cells can be used in screening assays to identify agents that modulate RPE cell survival (in vitro and/or in vivo), to study RPE cell maturation, or to identify agents that modulate RPE cell maturation. Agents identified using such screening assays may be used in vitro or in vivo and may provide additional therapeutics that can be used alone or in combination with RPE cells to treat retinal degenerative diseases. In one embodiment, composition may comprise a substantially purified preparation of human RPE cells differentiated from human pluripotent stem cells, wherein the RPE cells express, at the mRNA and protein level, RPE-65, Bestrophin, PEDF, CRALBP, Otx2, and MITF, and wherein the cells substantially lack expression of Oct-4, NANOG, and Rex-1. In another embodiment, the RPE cells comprise differentiated RPE cells and mature differentiated RPE cells, and wherein at least the mature differentiated RPE cells further express, at the mRNA and protein level, PAX2, pax-6, and tyrosinase. In another embodiment, the RPE cells are differentiated from human ES cells or human iPS cells.

The composition may comprise at least $10^5$ cells, at least $10^6$ cells, at least $10^7$ cells, at least $10^8$ cells, at least $10^9$ cells, at least $10^{10}$ cells, or between 10 and $10^{10}$ cells.

The composition may comprise cryopreserved cells. In one embodiment, the composition may comprise a cryopreserved preparation comprising at least about $10^4$ human RPE cells, wherein the preparation is a substantially purified preparation of human RPE cells derived from human pluripotent stem cells, and wherein the RPE cells express RPE-65, Bestrophin, PEDF, CRALBP, Otx2, and MITF. In another embodiment, at least about 85% of the RPE cells retain viability following thawing. For example, the RPE cells may be cryopreserved by a method comprising: (a) culturing RPE cells, (b) harvesting said RPE cells, (c) centrifuging said RPE cells, (d) resuspending said RPE cells in 10% DMSO/90% FBS solution; and (e) freezing said RPE cells.

Another exemplary embodiment provides a method of detecting the presence of human embryonic stem cells in a cell population, comprising:

(a) providing a cell population;

(b) applying a first stain and a second stain to said cell population, wherein said first stain detects alkaline phosphatase and said second stain detects a marker that is indicative of embryonic stem cells, and wherein cells that are positive for said first stain are detectable under visible and ultraviolet light, and cells that are positive for said second stain are detectable under ultraviolet light;

(c) microscopically observing the cells of said cell population under visible light to detect cells that are positive for said first marker;

(e) microscopically observing said cells that are positive for said first marker under ultraviolet light and determining whether a cell is positive for said first marker and said second marker; and (f) identifying a cell that is positive for said first marker and said second marker as an embryonic stem cell.

The cell population may comprise RPE cells differentiated from pluripotent cells by the methods described in U.S. Pat. Nos. 7,795,025, 7,794,704, and 7,736,896, U.S. Ser. No. 12/682,712, U.S. Provisional Applications 60/998,668, 60/998,766, 61/009,911, 61/009,908, and 61/262,002, WO/2009/051671, and WO 2011/063005, each of which is incorporated by reference herein in its entirety.

In one embodiment, the target cells are embryonic stem cells, induced pluripotent stem (iPS) cells, adult stem cells, hematopoietic cells, fetal stem cells, mesenchymal stem cells, postpartum stem cells, multipotent stem cells, or embryonic germ cells. In another embodiment, the pluripotent stem cells may be mammalian pluripotent stem cells. In still another embodiment, the pluripotent stem cells may be human pluripotent stem cells including but not limited to human embryonic stem (hES) cells, human induced pluripotent stem (iPS) cells, human adult stem cells, human hematopoietic stem cells, human fetal stem cells, human mesenchymal stem cells, human postpartum stem cells, human multipotent stem cells, or human embryonic germ cells. In another embodiment, the pluripotent stem cells may be a hES cell line listed in the European Human Embryonic Stem Cell Registry—hESCreg. In another embodiment, the hES cell line may be a blastomere-derived hES cell line such as MA09 or another cell line derived by the methods described in U.S. Pat. No. 7,893,315 or 7,838,727, each of which is incorporated by reference herein in its entirety.

In one embodiment, the invention provides for the use of a pharmaceutical preparation of RPE cells in the manufacture of a medicament for the treatment of retinal degeneration.

In one embodiment, the invention provides a method of treating retinal degeneration comprising administering an effective amount of RPE cells described herein. In another embodiment, the retinal degeneration is due to choroideremia, diabetic retinopathy, age-related macular degeneration, retinal detachment, retinitis pigmentosa, or Stargardt's Disease.

In one embodiment, the preparation is transplanted in a suspension, matrix, gel, colloid, scaffold, or substrate. In another embodiment, the preparation is administered by injection into the subretinal space of the eye.

In a further embodiment, the effective amount is at least about 20,000-200,000 RPE cells. In another embodiment, the effective amount is at least about 20,000, 50,000, 75,000, 100,000, 125,000, 150,000, 175,000, 180,000, 185,000, 190,000, or 200,000 RPE cells.

In one embodiment, the method further comprising monitoring the efficacy of the method by measuring electroretinogram responses, optomotor acuity threshold, or luminance threshold in the subject.

In one embodiment, the preparation is substantially free of ES cell, viral, bacterial, or fungal contamination. In another embodiment, the RPE cells are functional RPE cells capable of integrating into the retina upon transplantation. In a further embodiment, the RPE cells improve visual acuity following transplantation.

The present invention provides methods for the treatment of eye disorders. In particular, these methods involve the use of RPE cells to treat or ameliorate the symptoms of eye disorders, particularly eye disorders caused or exacerbated, in whole or in part, by damage to or breakdown of the endogenous RPE layer (e.g., retinal degeneration).

In one embodiment, the RPE cells described herein are substantially free of genetic mutations that may lead to retinal degeneration.

In one embodiment, the RPE cells may be transplanted with a biocompatible polymer such as polylactic acid, poly (lactic-co-glycolic acid), 50:50 PDLGA, 85:15 PDLGA, and INION GTR® biodegradable membrane (mixture of biocompatible polymers).

In another embodiment, the RPE cells adhere to Bruch's membrane after transplantation, establish polarity, and integrate into the receipt's tissue.

In one embodiment, the RPE cells may improve visual acuity after transplantation. In another embodiment, the RPE cells may substantially improve visual acuity after transplantation.

In one embodiment, the RPE cells lack substantial expression of embryonic stem cell markers including but not limited to Oct-4, NANOG, Rex-1, alkaline phosphatase, Sox2, TDGF-1, DPPA-2, and DPPA-4. In another embodiment, the RPE cells express RPE cell markers including but not limited to RPE65, CRALBP, PEDF, Bestrophin, MITF, Otx2, PAX2, Pax-6, and tyrosinase. In a further embodiment, the RPE cells express at least one gene, wherein expression of the at least one gene is increased in the RPE cells relative to expression in human ES cells. In one embodiment, the RPE cells show increased alpha integrin subunit expression. In another embodiment, the alpha integrin subunit is alpha 1, 2, 3, 4, 5, 6, or 9. In yet another embodiment, the expression is mRNA expression, protein expression, or both mRNA and protein expression.

The present invention provides for a method of providing a RPE preparation to a clinical site comprising (a) thawing vials of cryopreserved RPE cells, (b) resuspending the RPE cells in media, (c) centrifuging the RPE cells, (d) resuspending the RPE cells in media, (e) aliquoting the RPE cells into vials, and (f) transferring to the clinical site. In one embodiment, the resuspension and centrifugation steps may be repeated at least 1, 2, 3, 4, or 5 times. In another embodiment, the RPE product is transported to the clinical site within at least about 1, 2, 3, 4, 5, 6, 7, 8, 9, or 10 hours of completion of step (e). In a further embodiment, the vials may be labeled.

The present invention also provides a method for a providing RPE cell preparation for sale comprising (a) producing RPE cells and (b) preparing said RPE cell preparations for transfer to a customer. In one embodiment, the method may comprise cryopreserving the RPE cells. In another embodiment, the method comprises offering said RPE cell preparations for sale. In a further embodiment, the method comprises advertising the RPE cell preparations.

The invention contemplates any combination of the aspects and embodiments described above or below. For example, preparations of RPE cells comprising any combination of differentiated RPE cells and mature RPE cells can be used in the treatment of any of the conditions described herein. Similarly, methods described herein for producing RPE cells using human embryonic stem cells as a starting material may be similarly performed using any human pluripotent stem as a starting material.

DETAILED DESCRIPTION

Figure 1:
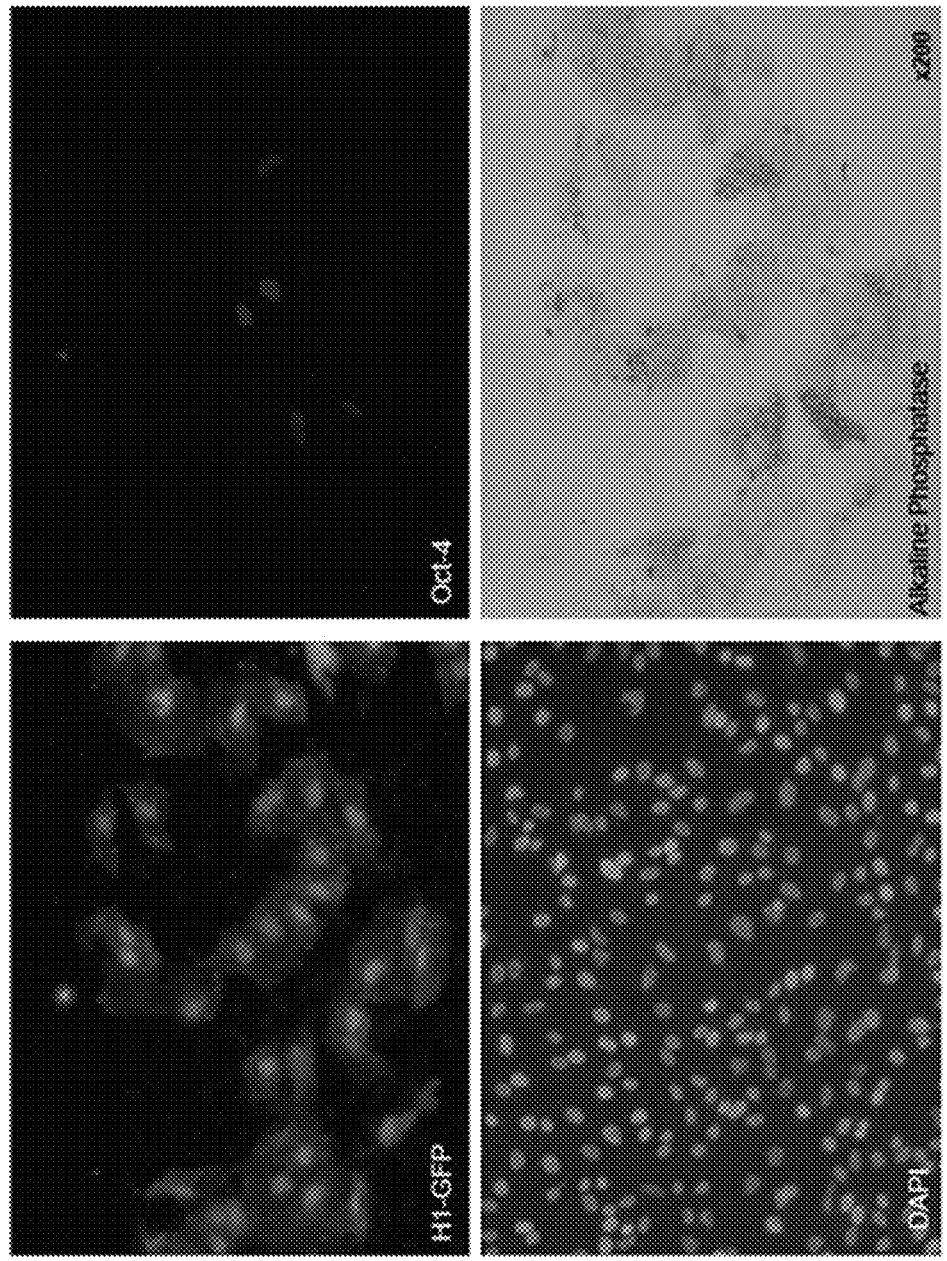
FIG. 1 is a representative micrograph showing detection of hES cells (Oct-4 positive and Alkaline Phosphatase positive) among differentiated cells. GFP expression confirms hES cell identity.

Conventional methods of detecting stem cells have limited sensitivity due to background expression of stem cell genes in non-stem cells and due to cell loss during sample preparation. The presently disclosure provides methods that can overcome these limitations and provide a highly sensitive method of detecting rare cell types in a cell population. Using these methods, an operator can examine on the order of between one and ten million stained cells per hour and detect individual cells of the target cell type in the cell population. Exemplary embodiments may be performed in an automated or semi-automated fashion which may further improve throughput. For example, when differentiated cells are produced from ES cells, it is desirable to determine whether any residual ES cells remain in the cell population, and a given lot of cells may be discarded if the proportion of ES cells exceeds some preset threshold. Several million representative cells can be examined from each lot of differentiated cells with expenditure of just a few hours of labor, providing greatly increased assurance of the absence of residual ES cells.

Because arbitrarily large numbers of cells can be examined, embodiments of the present methods have potentially unlimited sensitivity.

In an exemplary embodiment, cells are plated at high density but most preferably in no greater density than a monolayer (to simplify microscopic observation of the cells), which may be on top of a monolayer of feeder cells, and then stained for the presence of two or more characteristic markers of the target cell type, including a first marker which is detectable under visible light and a second marker which is detectable under ultraviolet light. The plated cells are then microscopically observed under visible light to detect cells expressing the first marker. Starting from one corner of the plated cells, the operator (or an automated system) scans across the entire plate and back in overlapping tracks, thus ensuring that each cell is examined. Because visible light is used, the unstained cells are visible and the focal plane can be adjusted as needed to ensure that the cells remain in focus as the plated cells are moved through the field of view. Use of visible light also prevents photobleaching that can occur under ultraviolet light. Scanning under visible light can be performed with relatively low magnification, which increases the number of cells that are observed in each microscopic field and increases throughput. Cells that are positive for the first marker are then examined under ultraviolet light to determine whether those cells also express the second marker. The selection of markers may be based on their known expression in pluripotent cells: for example, alkaline phosphatase (which may be used with ES cells as the marker used to "scan" the whole plate in visual light) is known to stay in hES cells longer than the other marker when they begin to differentiate. Thus if a cell is positive for the alkaline phosphatase, it can be either positive or negative for the second marker, and therefore, cells positive for the first and second marker are considered an hES cell. Preferably (as with AP and Oct-4 for hES cells) the first marker stains the target cells robustly (even though it may stain other cells as well) to avoid missing the chance to observe cells that may be positive for the second marker but have low or undetectable expression of the first marker. Typically positive cells are photographed so that comparison of photographs can avoid double-counting of cells that are observed in overlapping fields. The total number of plated cells is determined by counting all cells in each of one or more representative microscopic fields and dividing the number of cells counted by the fraction of the total plated area that was counted. Finally, the number of target cells detected is expressed as a proportion of the total number of cells examined.

These markers are chosen to distinguish target cells from the other cell types in the population. For example, if the target cells are hES cells and the other cell type in the population is human RPE cells then the first marker may be alkaline phosphatase and the second marker may be Oct-4. Other exemplary hES cell markers that may be used with these methods include: Nanog, Stage-specific embryonic antigen-3 (SSEA-3), Stage-specific embryonic antigen-4 (SSEA-4), TRA-1-60, TRA-1-81, TRA-2-49/6E, Sox2, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (hTERT), SALL4, E-CADHERIN, Cluster designation 30 (CD30), Cripto (TDGF-1), GCTM-2, Genesis, Germ cell nuclear factor, and Stem cell factor (SCF or c-Kit ligand). The present methods utilize at least two markers and may utilize, three, four, five, six, etc. markers which may provide further confirmation of whether a cell is of a target type.

In an additional exemplary embodiment, the target cell is a cancer stem cell and is detected by staining for one or more of the markers disclosed in one of the following U.S. published patent applications: 20100169990, 20090004205, 20080194022, 20080178305, 20080175870, 20080064049, 20070297983, 20070259969, 20070231325, 20070212737, 20070190647, 20060073125, 20060051325, 20040037815, and 20020119565, each of which is hereby incorporated by reference in its entirety.

Preferably the cells are plated under conditions that favor the maintenance of the target cell type. By plating under such conditions, the target cell type is more likely to be retained in the culture and the sensitivity of the method should be improved. For example, if the target cells are hES cells, the cells may be plated under conditions known to maintain hES cell in the pluripotent state. Exemplary culture conditions include plating on feeder cells, which may be mitotically inactivated by pre-treatment with irradiation or mitomycin C or other methods known in the art, or in media conditioned by feeder cells. Numerous suitable feeder cell types are known in the art including primary fibroblast cultures such as murine embryonic fibroblast (MEF), human adult skin fibroblasts, STO cells, and others. Culture conditions for feeder-free maintenance of ES cells are also known in the art and may include matrigel, laminin, adrenocorticotropic hormone, conditioned media, or any combination thereof. Exemplary ES cell culture media, including feeder-free culture media, are described in Carpenter et al., Dev Dyn. 2004 February; 229(2):243-58; Xu et al., Nat. Biotechnol. 2001 October; 19(10):971-4; Rosler et al., Dev Dyn. 2004 February; 229(2):259-74; and Amit et al., Biol Reprod. 2004 March; 70(3):837-45; WO01/51616; U.S. Pat. No. 6,800,480; US PGPub. No. 2009/0275128; US PGPub. No. 2008/0064099; and US PGPub. No. 2007/0160974, each of which is hereby incorporated by reference in its entirety.

Preferably, the method is validated to determine its sensitivity, for example by "spiking experiments" in which defined numbers of cells of a target cell type are added to a population, which is then assayed using the subject methods to detect cells of the target cell type. Use of populations containing defined numbers of target cells permits determination of the minimum number of target cells that must be present or the limit of detection of the assay, e.g., the minimum percentage of the population that must, on average, be of the target cell type before target cells are detected by the assay. The limit of detection may be expressed as a ratio or fraction that indicates the minimum proportion of cells of the target cell type that can be detected in the assay (e.g., 5 in 600,000 cells or 0.0008%).

The method may include a step of determining a correction factor that can be used to correct the sensitivity or limit of detection of the assay. For example, the target cells may be lost during culturing prior to performing the assay (e.g., target cells may differentiate into other cell types). Defined numbers of cells of the target type may be plated under the same conditions as in the spiking experiments, but in the absence of the other type of cells in the population (though if feeder cells are part of the culture conditions then they may be present). For example, if feeder cells of a different species than the target cells are present, the cells may be stained with a species-specific antibody that specifically identifies cells of the target cells' species, which would detect cells that have lost the specific markers of target cells.

After this culturing, the culture can be examined to determine the fraction of target cells that retained the expression of the target cell markers used in the assay, thereby determining a "correction factor" that establishes the relationship between the number of cells plated and the number that retain the phenotypes used for detection. For example, if it is determined that 50% of the target cells lose expression of the assayed target cell markers under these conditions, then the effective number of target cells is (e.g., used in calculating the limit of detection in spiking experiments) is reduced accordingly. Thus, if it is shown in "spiking" experiments that the assay can detect as few as ten added target cells per million cells in the population, but that 50% of target cells lose the detected phenotype during culturing, then the corrected limit of detection of the assay may be computed to be five cells in ten million to reflect the number of target cells that actually remain present in the population.

Additionally, the method preferably employs sample preparations that maximize the number of target cells that remain present in the population and retain expression of the target cell markers used for their detection. An additional exemplary embodiment provides a method of identifying a culture condition that preserves expression of a selected marker by target cells, comprising plating target cells under varying culture conditions, identifying the fraction of target cells that retain expression of one or more markers characteristic of target cells under each culture condition, and identifying the culture conditions that retains a greater fraction as a culture condition that preserves expression of a selected marker by target cells. For example, the present disclosure demonstrates that for detecting hES cells, the retention of hES cell markers (and therefore the sensitivity of the assay) is greatly improved by using hES cell culture conditions (culture on MEFs in hES cell culture media) rather than RPE cell culture conditions (absence of MEFs and a medium in which hES cells differentiate).

The markers may be detected using at least one stain that is detectable under visible light and another marker that is detectable under ultraviolet light. Markers detectable under visible light may be detectable based on an enzymatic activity. Exemplary enzymes that can produce colored products detectable under visible light include alkaline phosphatase, peroxidases (including horseradish peroxidase), and β-galactosidases. These enzymes may be expressed by target cells, or may be coupled to a molecule that binds to a target cells (such as a primary or secondary antibody).

One marker that is detectable under visible light that may be used in embodiments of the present disclosure is alkaline phosphatase, which may be stained based on its enzymatic activity. The alkaline phosphatase may be endogenously expressed, coupled to an antibody, or both. Numerous substrates can be used for alkaline phosphatase staining to produce a product detectable under visible light, including: napthol AS-BI phosphate as substrate and fast red violet dye as the colorimetric read-out (e.g., using the STEMGENT® Alkaline Phosphatase (AP) Staining Kit II); Bromo-Chloro-Indolylphosphate (BCIP) and Nitro Blue Tetrazolium (NBT/Thiazoiyl Blue/Nitro BT) (e.g., Alkaline Phosphatase Blue Microwell Substrate (SIGMA-ALDRICH®)); BCIP reagent and INTX reagent (SIGMA-ALDRICH®); naphthol AS-BI and fast red violet LB (e.g. Leukocyte Alkaline Phosphatase kit (SIGMA-ALDRICH®); substrates which form precipitates are based on either reduction of tetrazolium salts or the production of colored diazo compounds (e.g. VECTOR® Red, VECTOR® Blue, VECTOR® Black, p-Nitrophenylphosphate, BCIP/NBT AP Substrate Kit, and 5-bromo-4-chloro-3-indolyl phosphate/nitroblue tetrazolium).

Optionally an alkaline phosphatase inhibitor, such as Levamisole ((S)-6-phenyl-2, 3, 5, 6-tetrahydroimidazo [2,1-b][1, 3]thiazole) or a heat treatment, may be used to inhibit undesired background alkaline phosphatase activity.

Another marker that is detectable under visible light that may be used in embodiments of the present disclosure is peroxidase, such as horseradish peroxidase (HRP), which may be stained based on its enzymatic activity. Peroxidase may be endogenously expressed, coupled to an antibody, or both. Peroxidase can catalyze the conversion of chromogenic substrates into colored molecules. Exemplary Peroxidase substrates include 3,3',5,5'-Tetramethylbenzidine (TMB); 3,3'-Diaminobenzidine (DAB); 3-Amino-9-Ethyl-Carbazole (AEC); 4-Chloro-1-naphthol; 2,2'-azino-bis(3-ethylbenzthiazoline-6-sulphonic acid) (ABTS); 2,3,5-Triphenyltetrazolium chloride; 2-Chloro-5,5-dimethyl-1,3-cyclohexanedione; 3,3',5,5'-Tetramethylbenzidine; 3,3'-Diaminobenzidine tetrahydrochloride; 3-Nitrotetrazolium blue chloride; 4-Aminophthalhydrazide; 4-Chloro-1-naphthol; 4-Chloro-7-nitrobenzofurazan; 5-Aminosalicylic acid; Dicarboxidine dihydrochloride; Guaiacol; Hydrogen peroxide-Urea adduct; Iodonitrotetrazolium chloride; Luminol; MTT Formazan; N-(4-Aminobutyl)-N-ethylisoluminol; N-(6-Aminohexyl)-N-ethylisoluminol; Nitrotetrazolium Blue chloride; Pyrogallol; Tetranitroblue tetrazolium chloride; Tetrazolium Blue Chloride indicator; Tetrazolium Violet; o-Dianisidine; o-Dianisidine dihydrochloride; o-Phenylenediamine dihydrochloride; o-Phenylenediamine free base; and trans-5-Phenyl-4-pentenyl hydroperoxide.

Another marker that is detectable under visible light that may be used in embodiments of the present disclosure is β-galactosidase, which may be stained based on its enzymatic activity. β-galactosidase may be endogenously expressed, coupled to an antibody, or both. β-galactosidase can catalyze the conversion of chromogenic substrates into colored molecules. Exemplary β-galactosidase substrates include: 1-Methyl-3-indolyl-β-D-galactopyranoside; 2-Nitrophenyl β-D-galactopyranoside; 4-Methylumbelliferyl β-D-galactopyranoside; 4-Nitrophenyl β-D-galactopyranoside; 5-Bromo-3-indolyl β-D-galactopyranoside; 5-Bromo-4-chloro-3-indolyl β-D-galactopyranoside; 5-Bromo-6-chloro-3-indolyl-β-D-galactopyranoside; 6-Bromo-2-naphthyl β-D-galactopyranoside; 6-Chloro-3-indolyl-β-D-galactopyranoside; Fluorescein di(β-D-galactopyranoside); and Resorufin β-D-galactopyranoside.

When antibodies are used as a component of a stain, a marker can be directly or indirectly coupled to the antibody. Examples of indirect coupling include avidin/biotin coupling, coupling via a secondary antibody, and combinations thereof. For example, cells may be stained with a primary antibody that binds a target-specific antigen, and a secondary antibody that binds the primary antibody or a molecule coupled to the primary antibody can be coupled to a detectable marker. Use of indirect coupling can improve signal to noise ratio, for example by reducing background binding and/or providing signal amplification.

Other stains detectable under visible light include particles including gold, silver, or latex. For example, particles may be directly or indirectly coupled to primary or secondary antibodies or otherwise bound to target cells. Optionally, staining may be further enhanced using immunogold-silver staining, in which cells are stained with an antibody coupled to colloidal gold, and the gold particles are revealed using a silver precipitation reaction method (Holgate et al., J Histochem Cytochem. 1983 July; 31(7):938-44).

Exemplary embodiments of the present method utilize antibodies coupled to a fluorescent molecule, such as ethidium bromide, SYBR® Green, fluorescein isothiocyanate (FITC), DYLIGHT® Fluors, green fluorescent protein (GFP), TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloiO-2',7'-dimethoxy fluorescein, TET (6-carboxy-2',4,7,7'-tetrachlorofluorescein), HEX (6-carboxy-2',4,4',5',7,7'-hexachlorofluorescein), Joe (6-carboxy-4',5'-dichloro-2',7'-dimethox fluorescein) 5-carboxy-2',4',5',7'-tetrachlorofluorescein, 5-carboxyfluorescein, 5-carboxy rhodamine, Tamra (tetramethylrhodamine), 6-carboxyrhodamine, Rox (carboxy-X-rhodamine), R6G (Rhodamine 6G), phthalocyanines, azomethines, cyanines (e.g. Cy3, Cy3.5, Cy5), xanthines, succinylfluoresceins, N, N-diethyl-4-(5'-azobenzouiazolyl)-phenylamine and aminoacridine. Other exemplary fluorescent molecules include quantum dots, which are described in the patent literature [see, for example, U.S. Pat. Nos. 6,207,299, 6,322,901, 6,576,291, 6,649, 138 (surface modification methods in which mixed hydrophobic/hydrophilic polymer transfer agents are bound to the surface of the quantum dots), U.S. Pat. Nos. 6,682,596, 6,815,064 (for alloyed or mixed shells), each of which patents is incorporated by reference herein)], and in the technical literature [such as "Alternative Routes toward High Quality CdSe Nanocrystals," (Qu et al., Nano Lett., 1 (6):333-337 (2001)]. Quantum dots having various surface chemistries and fluorescence characteristics are commercially available from INVITROGEN® Corporation, Eugene, Greg., EVIDENT TECHNOLOGIES™ (Troy, N.Y.), and Quantum Dot Corporation (Hayward, Calif.), amongst others. Quantum dot" also includes alloyed quantum dots, such as ZnSSe, ZnSeTe, ZnSTe, CdSSe, CdSeTe, ScSTe, HgSSe, HgSeTe, HgSTe, ZnCdS, ZnCdSe, ZnCdTe, Znl lgS, ZnHgSe, ZnHgTe, CdHgS, CdHgSe, CdHgTe, ZnCdSSe, ZoHgSSe, ZnCdSeTe, ZnHgSeTe, CdHgSSe, CdHgSeTe, InGaAs, GaAlAs, and InGaN. Alloyed quantum dots and methods for making the same are disclosed, for example, in US Application Publication No. 2005/00121 82 and PCT Publication WO 2005/001889.

The present disclosure provides exemplary embodiments illustrating highly sensitive detection human embryonic stem cells in a differentiated RPE cell population, but can readily be adapted to detect other cell types or with other species than human. For example, these methods may be used with other cell types including other stem cell types, cancer cells, feeder cells, xenogeneic cells, or other any other cell type that expresses characteristic markers. Similarly, these methods may be used with human, non-human primates, antelopes, bovines, camels, cats, chevrotains (mouse deer), chimpanzee, cow, deer, dog, giraffes, goat, guinea pig, hamster, hippopotamuses, horse, human, mouse, non-human primate, ovine, peccaries, pig, pronghorn, rabbit, rat, rhesus macaque, rhinoceroses, sheep, tapirs, and ungulates, or any other mammalian or non-mammalian cell type.

Target cells (such as stem cells) may be identified by expression of one or more stem cell markers. It may be desirable to test for expression of one or more target cell markers (e.g., two markers, three markers, four markers, etc.) to provide further assurance that a cell expressing a target cell marker is in fact a target cell. For example, a "cocktail" of antibodies to different markers may be each coupled (whether directly or indirectly) to the same label or to different labels. As an example, a cocktail of antibodies to different markers may each contain a binding motif that binds the same label (e.g., each may contain an Fc of the same species that is recognized by the same secondary antibody, or each may be biotinylated and specifically bound by the same avidin-coupled label). Optionally, two or more different antibodies or cocktails of antibodies may be utilized. Preferably the cells are stained using at least two labels that can be distinguished from one another, thereby permitting identification of cells that express at least two different markers of the target cell types. Cells may also be stained using at least three, four, five, or more different labels that can be distinguished from one another, thereby permitting detection of cells that express greater numbers of markers of the target cell type. Optionally, a cell may be identified as a cell of the target type if it expresses a preselected number of markers or certain preselected combinations of markers.

Additionally, it is not necessary that the marker(s) of the target cell type be unique to the target cells, as long as they permit distinction of the target cells from other cells in the population. For example, alkaline phosphatase may be used as a suitable marker for detecting hES cells within a population of RPE, even though other cell types also express alkaline phosphatase, because alkaline phosphatase is not normally expressed by RPE.

Exemplary embryonic stem cell markers include alkaline phosphatase, Oct-4, Nanog, Stage-specific embryonic antigen-3 (SSEA-3), Stage-specific embryonic antigen-4 (SSEA-4), TRA-1-60, TRA-1-81, TRA-2-49/6E, Sox2, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (hTERT), SALL4, E-CADHERIN, Cluster designation 30 (CD30), Cripto (TDGF-1), GCTM-2, Genesis, Germ cell nuclear factor, and Stem cell factor (SCF or c-Kit ligand).

For some exemplary cell types, cells may only be considered positive for a given marker if that marker exhibits a characteristic localization or pattern within the cell. For instance, a cell may be considered "positive" if a cytoskeletal marker is present in the cytoskeleton and "negative" if there is some diffuse cytoplasmic staining. In such a case, cells may be cultured under suitable conditions (e.g., as adherent cultures) to establish the characteristic localization or pattern within the cell. Suitable culture conditions and time for cytoskeleton assembly (or other processes to establish subcellular organization) that may be necessary for robust detection of a given marker are readily determined by those of ordinary skill in the art. Additionally, markers may readily be chosen which decrease or eliminate the need for adherent culture as a precondition to robust staining. For example, non-adherent cell populations may be stained after Cytospin-like procedure (in which cells may lose their normal morphology while being "squashed" onto slides by centrifugal force); suitable markers for use under such circumstances are well known or readily identified.

In addition to the foregoing stem cell markers, the presently disclosed methods may be used with other cell types. Markers for other exemplary cell populations or target cell types that can be used in accord with embodiments of the presently disclosed method are listed in Table 1 below.

TABLE 1

Exemplary cell types and markers indicative of those cell types.

| Marker Name | Cell Type | Significance |
| --- | --- | --- |
| Blood Vessel | | |
| Fetal liver kinase-1 (Flk1) | Endothelial | Cell-surface receptor protein that identifies endothelial cell progenitor; marker of cell-cell contacts |
| Smooth muscle cell-specific myosin heavy chain | Smooth muscle | Identifies smooth muscle cells in the wall of blood vessels |
| Vascular endothelial cell cadherin | Smooth muscle | Identifies smooth muscle cells in the wall of blood vessels |
| Bone | | |
| Bone-specific alkaline phosphatase (BAP) | Osteoblast | Enzyme expressed in osteoblast; activity indicates bone formation |
| Hydroxyapatite | Osteoblast | Minerlized bone matrix that provides structural integrity; marker of bone formation |
| Osteocalcin (OC) | Osteoblast | Mineral-binding protein uniquely synthesized by osteoblast; marker of bone formation |
| Bone Marrow and Blood | | |
| Bone morphogenetic protein receptor (BMPR) | Mesenchymal stem and progenitor cells | Important for the differentiation of committed mesenchymal cell types from mesenchymal stem and progenitor cells; BMPR identifies early mesenchymal lineages (stem and progenitor cells) |
| CD4 and CD8 | White blood cell (WBC) | Cell-surface protein markers specific for mature T lymphocyte (WBC subtype) |
| CD34 | Hematopoietic stem cell (HSC), satellite, endothelial progenitor | Cell-surface protein on bone marrow cell, indicative of a HSC and endothelial progenitor; CD34 also identifies muscle satellite, a muscle stem cell |
| $CD34^+Sca1^+ Lin^-$ profile | Mesencyhmal stem cell (MSC) | Identifies MSCs, which can differentiate into adipocyte, osteocyte, chondrocyte, and myocyte |
| CD38 | Absent on HSC Present on WBC lineages | Cell-surface molecule that identifies WBC lineages. Selection of $CD34^+/CD38^-$ cells allows for purification of HSC populations |
| CD44 | Mesenchymal | A type of cell-adhesion molecule used to identify specific types of mesenchymal cells |
| c-Kit | HSC, MSC | Cell-surface receptor on BM cell types that identifies HSC and MSC; binding by fetal calf serum (FCS) enhances proliferation of ES cells, HSCs, MSCs, and hematopoietic progenitor cells |
| Colony-forming unit (CFU) | HSC, MSC progenitor | CFU assay detects the ability of a single stem cell or progenitor cell to give rise to one or more cell lineages, such as red blood cell (RBC) and/or white blood cell (WBC) lineages |
| Fibroblast colony-forming unit (CFU-F) | Bone marrow fibroblast | An individual bone marrow cell that has given rise to a colony of multipotent fibroblastic cells; such identified cells are precursors of differentiated mesenchymal lineages |
| Hoechst dye | Absent on HSC | Fluorescent dye that binds DNA; HSC extrudes the dye and stains lightly compared with other cell types |
| Leukocyte common antigen (CD45) | WBC | Cell-surface protein on WBC progenitor |
| Lineage surface antigen (Lin) | HSC, MSC Differentiated RBC and WBC lineages | Thirteen to 14 different cell-surface proteins that are markers of mature blood cell lineages; detection of Lin-negative cells assists in the purification of HSC and hematopoietic progenitor populations |
| Mac-1 | WBC | Cell-surface protein specific for mature granulocyte and macrophage (WBC subtypes) |
| Muc-18 (CD146) | Bone marrow fibroblasts, endothelial | Cell-surface protein (immunoglobulin superfamily) found on bone marrow fibroblasts, which may be important in hematopoiesis; a subpopulation of Muc-18+ cells are mesenchymal precursors |
| Stem cell antigen (Sca-1) | HSC, MSC | Cell-surface protein on bone marrow (BM) cell, indicative of HSC and MSC Bone Marrow and Blood cont. |

TABLE 1-continued

Exemplary cell types and markers indicative of those cell types.

| Marker Name | Cell Type | Significance |
| --- | --- | --- |
| Stro-1 antigen | Stromal (mesenchymal) precursor cells, hematopoietic cells | Cell-surface glycoprotein on subsets of bone marrow stromal (mesenchymal) cells; selection of Stro-1+ cells assists in isolating mesenchymal precursor cells, which are multipotent cells that give rise to adipocytes, osteocytes, smooth myocytes, fibroblasts, chondrocytes, and blood cells |
| Thy-1 | HSC, MSC | Cell-surface protein; negative or low detection is suggestive of HSC |
| Cartilage | | |
| Collagen types II and IV | Chondrocyte | Structural proteins produced specifically by chondrocyte |
| Keratin | Keratinocyte | Principal protein of skin; identifies differentiated keratinocyte |
| Sulfated proteoglycan | Chondrocyte | Molecule found in connective tissues; synthesized by chondrocyte |
| Fat | | |
| Adipocyte lipid-binding protein (ALBP) | Adipocyte | Lipid-binding protein located specifically in adipocyte |
| Fatty acid transporter (FAT) | Adipocyte | Transport molecule located specifically in adipocyte |
| Adipocyte lipid-binding protein (ALBP) | Adipocyte | Lipid-binding protein located specifically in adipocyte |
| General | | |
| Y chromosome | Male cells | Male-specific chromosome used in labeling and detecting donor cells in female transplant recipients |
| Karyotype | Most cell types | Analysis of chromosome structure and number in a cell |
| Liver | | |
| Albumin | Hepatocyte | Principal protein produced by the liver; indicates functioning of maturing and folly differentiated hepatocytes |
| B-1 integrin | Hepatocyte | Cell-adhesion molecule important in cell-cell interactions; marker expressed during development of liver |
| Nervous System | | |
| CD133 | Neural stem cell, HSC | Cell-surface protein that identifies neural stem cells, which give rise to neurons and glial cells |
| Glial fibrillary acidic protein (GFAP) | Astrocyte | Protein specifically produced by astrocyte |
| Microtubule-associated protein-2 (MAP-2) | Neuron | Dendrite-specific MAP; protein found specifically in dendritic branching of neuron |
| Myelin basic protein (MPB) | Oligodendrocyte | Protein produced by mature oligodendrocytes; located in the myelin sheath surrounding neuronal structures |
| Nestin | Neural progenitor | Intermediate filament structural protein expressed in primitive neural tissue |
| Neural tubulin | Neuron | Important structural protein for neuron; identifies differentiated neuron |
| Neurofilament (NF) | Neuron | Important structural protein for neuron; identifies differentiated neuron |
| Neurosphere | Embryoid body (EB), ES | Cluster of primitive neural cells in culture of differentiating ES cells; indicates presence of early neurons and glia |
| Noggin | Neuron | A neuron-specific gene expressed during the development of neurons |
| O4 | Oligodendrocyte | Cell-surface marker on immature, developing oligodendrocyte |
| O1 | Oligodendrocyte | Cell-surface marker that characterizes mature oligodendrocyte |

TABLE 1-continued

Exemplary cell types and markers indicative of those cell types.

| Marker Name | Cell Type | Significance |
| --- | --- | --- |
| Synaptophysin | Neuron | Neuronal protein located in synapses; indicates connections between neurons |
| Tau | Neuron | Type of MAP; helps maintain structure of the axon Pancreas |
| Cytokeratin 19 (CK19) | Pancreatic epithelium | CK19 identifies specific pancreatic epithelial cells that are progenitors for islet cells and ductal cells |
| Glucagon | Pancreatic islet | Expressed by alpha-islet cell of pancreas |
| Insulin | Pancreatic islet | Expressed by beta-islet cell of pancreas Pancreas |
| Insulin-promoting factor-1 (PDX-1) | Pancreatic islet | Transcription factor expressed by beta-islet cell of pancreas |
| Nestin | Pancreatic progenitor | Structural filament protein indicative of progenitor cell lines including pancreatic |
| Pancreatic polypeptide | Pancreatic islet | Expressed by gamma-islet cell of pancreas |
| Somatostatin | Pancreatic islet | Expressed by delta-islet cell of pancreas |
| Pluripotent Stem Cells | | |
| Alkaline phosphatase | Embryonic stem (ES), embryonal carcinoma (EC) | Elevated expression of this enzyme is associated with undifferentiated pluripotent stem cell (PSC) |
| Alpha-fetoprotein (AFP) | Endoderm | Protein expressed during development of primitive endoderm; reflects endodermal differentiation Pluripotent Stem Cells |
| Bone morphogenetic protein-4 | Mesoderm | Growth and differentiation factor expressed during early mesoderm formation and differentiation |
| Brachyury | Mesoderm | Transcription factor important in the earliest phases of mesoderm formation and differentiation; used as the earliest indicator of mesoderm formation |
| Cluster designation 30 (CD30) | ES, EC | Surface receptor molecule found specifically on PSC |
| Cripto (TDGF-1) | ES, cardiomyocyte | Gene for growth factor expressed by ES cells, primitive ectoderm, and developing cardiomyocyte |
| GATA-4 gene | Endoderm | Expression increases as ES differentiates into endoderm |
| GCTM-2 | ES, EC | Antibody to a specific extracellular-matrix molecule that is synthesized by undifferentiated PSCs |
| Genesis | ES, EC | Transcription factor uniquely expressed by ES cells either in or during the undifferentiated state of PSCs |
| Germ cell nuclear factor | ES, EC | Transcription factor expressed by PSCs |
| Hepatocyte nuclear factor-4 (HNF-4) | Endoderm | Transcription factor expressed early in endoderm formation |
| Nestin | Ectoderm, neural and pancreatic progenitor | Intermediate filaments within cells; characteristic of primitive neuroectoderm formation |
| Neuronal cell-adhesion molecule (N-CAM) | Ectoderm | Cell-surface molecule that promotes cell-cell interaction; indicates primitive neuroectoderm formation |
| Oct-4/POU5F1 | ES, EC | Transcription factor unique to PSCs; essential for establishment and maintenance of undifferentiated PSCs |
| Pax6 | Ectoderm | Transcription factor expressed as ES cell differentiates into neuroepithelium |
| Stage-specific embryonic antigen-3 (SSEA-3) | ES, EC | Glycoprotein specifically expressed in early embryonic development and by undifferentiated PSCs |
| Stage-specific embryonic antigen-4 (SSEA-4) | ES, EC | Glycoprotein specifically expressed in early embryonic development and by undifferentiated PSCs |
| Stem cell factor (SCF or c-Kit ligand) | ES, EC, HSC, MSC | Membrane protein that enhances proliferation of ES and EC cells, hematopoietic stem cell (HSCs), and mesenchymal stem cells (MSCs); binds the receptor c-Kit |
| Telomerase | ES, EC | An enzyme uniquely associated with immortal cell lines; useful for identifying undifferentiated PSCs |
| TRA-1-60 | ES, EC | Antibody to a specific extracellular matrix molecule is synthesized by undifferentiated PSCs |

TABLE 1-continued

Exemplary cell types and markers indicative of those cell types.

| Marker Name | Cell Type | Significance |
| --- | --- | --- |
| TRA-1-81 | ES, EC | Antibody to a specific extracellular matrix molecule normally synthesized by undifferentiated PSCs |
| Vimentin | Ectoderm, neural and pancreatic progenitor | Intermediate filaments within cells; characteristic of primitive neuroectoderm formation |
| | Skeletal Muscle/Cardiac/Smooth Muscle | |
| MyoD and Pax7 | Myoblast, myocyte | Transcription factors that direct differentiation of myoblasts into mature myocytes |
| Myogenin and MR4 | Skeletal myocyte | Secondary transcription factors required for differentiation of myoblasts from muscle stem cells |
| Myosin heavy chain | Cardiomyocyte | A component of structural and contractile protein found in cardiomyocyte |
| Myosin light chain | Skeletal myocyte | A component of structural and contractile protein found in skeletal myocyte |

The RPE cells may express RPE cell markers. For example, the expression level of the RPE cell genes RPE65, PAX2, PAX6, and tyrosinase, bestrophin, PEDF, CRALBP, Otx2, and MITF may be equivalent to that in naturally occurring RPE cells. The level of maturity of the RPE cells may assessed by expression of at least one of PAX2, PAX6, and tyrosinase, or their respective expression levels.

In contrast, the RPE cells may not express ES cell markers. For example, the expression levels of the ES cell genes Oct-4, NANOG, and/or Rex-1 may be about 100-1000 fold lower in RPE cells than in ES cells. For example, the RPE cells may substantially lack expression of ES cell markers including but not limited to octamer-binding transcription factor 4 (Oct-4, a.k.a., POU5F1), stage specific embryonic antigens (SSEA)-3 and SSEA-4, tumor rejection antigen (TRA)-1-60, TRA-1-80, alkaline phosphatase, NANOG, and Rex-1. Thus, in comparison to ES cells, RPE cells are substantially lack expression of Oct-4, NANOG, and/or Rex-1.

Preparations of RPE Cells

The present invention provides preparations of RPE cells and an indicator that indicates the number or fraction of pluripotent cells present, wherein the value of said indicator may be determined by applying the methods described herein to a cell population representative of the cells in said preparation. The invention described herein provides RPE cells, substantially purified populations of RPE cells, pharmaceutical preparations comprising RPE cells, and cryopreserved preparations of the RPE cells. The RPE cells described herein may be substantially free of at least one protein, molecule, or other impurity that is found in its natural environment (e.g., "isolated".) The RPE cells may be mammalian, including, human RPE cells. The invention also provides human RPE cells, a substantially purified population of human RPE cells, pharmaceutical preparations comprising human RPE cells, and cryopreserved preparations of the human RPE cells. The preparation may be a preparation comprising human embryonic stem cell-derived RPE cells, human iPS cell-derived RPE cells, and substantially purified (with respect to non-RPE cells) preparations comprising differentiated ES-derived RPE cells.

The RPE cell populations may include differentiated RPE cells of varying levels of maturity, or may be substantially pure with respect to differentiated RPE cells of a particular level of maturity. The RPE cells may be a substantially purified preparation comprising RPE cells of varying levels of maturity/pigmentation. For example, the substantially purified culture of RPE cells may contain both differentiated RPE cells and mature differentiated RPE cells. Amongst the mature RPE cells, the level of pigment may vary. However, the mature RPE cells may be distinguished visually from the RPE cells based on the increased level of pigmentation and the more columnar shape. The substantially purified preparation of RPE cells comprises RPE cells of differing levels of maturity (e.g., differentiated RPE cells and mature differentiated RPE cells). In such instances, there may be variability across the preparation with respect to expression of markers indicative of pigmentation. The pigmentation of the RPE cells in the cell culture may be homogeneous. Further, the pigmentation of the RPE cells in the cell culture may be heterogeneous, and the culture of RPE cells may comprise both differentiated RPE cells and mature RPE cells. Preparations comprising RPE cells include preparations that are substantially pure, with respect to non-RPE cell types, but which contain a mixture of differentiated RPE cells and mature differentiated RPE cells. Preparations comprising RPE cells also include preparations that are substantially pure both respect to non-RPE cell types and with respect to RPE cells of other levels of maturity.

The percentage of mature differentiated RPE cells in the culture may be reduced by decreasing the density of the culture. Thus, the methods described herein may further comprise subculturing a population of mature RPE cells to produce a culture containing a smaller percentage of mature RPE cells. The number of RPE cells in the preparation includes differentiated RPE cells, regardless of level of maturity and regardless of the relative percentages of differentiated RPE cells and mature differentiated RPE cells. The number of RPE cells in the preparation refers to the number of either differentiated RPE cells or mature RPE cells. The preparation may comprise at least about 75%, 80%, 85%, 90%, 91%, 92%, 93%, 94%, 95%, 96%, 97%, 98%, 99%, or 100% differentiated RPE cells. The preparation may comprise at least about 75%, 80%, 85%, 90%, 91%, 92%, 93%, 94%, 95%, 96%, 97%, 98%, 99%, or 100% mature RPE cells. The RPE cell preparation may comprise a mixed population of differentiated RPE cells and mature RPE cells.

The invention provides a cell culture comprising human RPE cells which are pigmented and express at least one gene that is not expressed in a cell that is not a human RPE. For example, although such RPE cells may have substantially the same expression of RPE65, PEDF, CRALBP, and bestrophin as a natural human RPE cell. The RPE cells may vary, depending on level of maturity, with respect to expression of one or more of PAX2, Pax-6, MITF, and/or tyrosinase. Note that changes in pigmentation post-differentiation also correlate with changes in PAX2 expression. Mature RPE cells may be distinguished from RPE cells by the level of pigmentation, level of expression of PAX2, Pax-6, and/or tyrosinase. For example, mature RPE cells may have a higher level of pigmentation or a higher level of expression of PAX2, Pax-6, and/or tyrosinase compared to RPE cells.

The preparations may be substantially purified, with respect to non-RPE cells, comprising at least about 75%, 80%, 85%, 90%, 91%, 92%, 93%, 94%, 95%, 96%, 97%, 98%, 99%, or 100% RPE cells. The RPE cell preparation may be essentially free of non-RPE cells or consist of RPE cells. For example, the substantially purified preparation of RPE cells may comprise less than about 25%, 20%, 15%, 10%, 9%, 8%, 7%, 6%, 5%, 4%, 3%, 2%, or 1% non-RPE cell type. For example, the RPE cell preparation may comprise less than about 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% non-RPE cells.

The RPE cell preparations may be substantially pure, both with respect to non-RPE cells and with respect to RPE cells of other levels of maturity. The preparations may be substantially purified, with respect to non-RPE cells, and enriched for mature RPE cells. For example, in RPE cell preparations enriched for mature RPE cells, at least about 30%, 40%, 45%, 50%, 55%, 60%, 65%, 70%, 75%, 80%, 85%, 90%, 91%, 92%, 93%, 94%, 95%, 96%, 97%, 98%, 99%, 99%, or 100% of the RPE cells are mature RPE cells. The preparations may be substantially purified, with respect to non-RPE cells, and enriched for differentiated RPE cells rather than mature RPE cells. For example, at least about 30%, 40%, 45%, 50%, 55%, 60%, 65%, 70%, 75%, 80%, 85%, 90%, 91%, 92%, 93%, 94%, 95%, 96%, 97%, 98%, 99%, or 100% of the RPE cells may be differentiated RPE cells rather than mature RPE cells.

The RPE cell preparations may comprise at least about $1\times10^3$, $2\times10^3$, $3\times10^3$, $4\times10^3$, $5\times10^3$, $6\times10^3$, $7\times10^3$, $8\times10^3$, $9\times10^3$, $10\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^{11}$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ RPE cells. The RPE cell preparations may comprise at least about 5,000-10,000, 50,000-100,000, 100,000-200,000, 200,000-500,000, 300,000-500,000, or 400,000-500,000 RPE cells. The RPE cell preparation may comprise at least about 20,000-50,000 RPE cells. Also, the RPE cell preparation may comprise at least about 5,000, 10,000, 20,000, 30,000, 40,000, 50,000, 60,000, 70,000, 75,000, 80,000, 100,000, or 500,000 RPE cells.

The RPE cell preparations may comprise at least about $1\times10^3$, $2\times10^3$, $3\times10^3$, $4\times10^3$, $5\times10^3$, $6\times10^3$, $7\times10^3$, $8\times10^3$, $9\times10^3$, $10\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^{11}$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ RPE cells/mL. The RPE cell preparations may comprise at least about 5,000-10,000, 50,000-100,000, 100,000-200,000, 200,000-500,000, 300,000-500,000, or 400,000-500,000 RPE cells/mL. The RPE cell preparation may comprise at least about 20,000-50,000 RPE cells/mL. Also, the RPE cell preparation may comprise at least about 5,000, 10,000, 20,000, 30,000, 40,000, 50,000, 60,000, 75,000, 80,000, 100,000, or 500,000 RPE cells/mL.

The preparations described herein may be substantially free of bacterial, viral, or fungal contamination or infection, including but not limited to the presence of HIV-1, HIV-2, HBV, HCV, CMV, HTLV-1, HTLV-2, parvovirus B19, Epstein-Barr virus, or herpesvirus 6. The preparations described herein may be substantially free of mycoplasma contamination or infection.

The RPE cells described herein may also act as functional RPE cells after transplantation where the RPE cells form a monolayer between the neurosensory retina and the choroid in the patient receiving the transplanted cells. The RPE cells may also supply nutrients to adjacent photoreceptors and dispose of shed photoreceptor outer segments by phagocytosis. Additionally, the RPE cells described herein may have undergone less senescence than cells derived from eye donors (e.g., the RPE cells are "younger" than those of eye donors). This allows the RPE cell described herein to have a longer useful lifespan than cells derived from eye donors.

The preparations comprising RPE cells may be prepared in accordance with Good Manufacturing Practices (GMP) (e.g., the preparations are GMP-compliant) and/or current Good Tissue Practices (GTP) (e.g., the preparations may be GTP-compliant.)

RPE Cell Cultures

The present invention also provides substantially purified cultures of RPE cells, including human RPE cells and an indicator that indicates the number or fraction of pluripotent cells present, wherein the value of said indicator may be determined by applying the methods described herein to a cell population representative of the cells in said cultures. The RPE cultures described herein may comprise at least about 1,000; 2,000; 3,000; 4,000; 5,000; 6,000; 7,000; 8,000; or 9,000 RPE cells. The culture may comprise at least about $1\times10^4$, $2\times10^4$, $3\times10^4$, $4\times10^4$, $5\times10^5$, $6\times10^4$, $7\times10^4$, $8\times10^4$, $9\times10^4$, $1\times10^5$, $2\times10^5$, $3\times10^6$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^89$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ RPE cells.

The RPE cells may be further cultured to produce a culture of mature RPE cells. The RPE cells may be matured, and the RPE cells may be further cultured in, for example MDBK-MM medium until the desired level of maturation is obtained. This may be determined by monitoring the increase in pigmentation level during maturation. As an alternative to MDBK-MM medium, a functionally equivalent or similar medium, may be used. Regardless of the particular medium used to mature the RPE cells, the medium may optionally be supplemented with a growth factor or agent. Both RPE cells and mature RPE cells are differentiated RPE cells. However, mature RPE cells are characterized by increased level of pigment in comparison to differentiated RPE cells. The level of maturity and pigmentation may be modulated by increasing or decreasing the density of the culture of differentiated RPE cells. Thus, a culture of RPE cells may be further cultured to produce mature RPE cells. Alternatively, the density of a culture containing mature RPE cells may be decreased to decrease the percentage of mature differentiated RPE cells and increase the percentage of differentiated RPE cells.

The RPE cells may be identified by comparing the messenger RNA transcripts of such cells with cells derived in vivo. An aliquot of cells is taken at various intervals during the differentiation of embryonic stem cells to RPE cells and assayed for the expression of any of the markers described above. These characteristic distinguish differentiated RPE cells.

The RPE cell culture may be a substantially purified culture comprising at least about 30%, 35%, 40%, or 45%, 50%, 55%, 60%, 65%, 70%, 75%, 80%, 85%, 90%, 91%, 92%, 93%, 94%, 95%, 96%, 97%, 98%, 99%, or 100% differentiated RPE cells. The substantially purified culture may comprise at least about 30%, 35%, 40%, or 45%, 50%, 55%, 60%, 65%, 70%, 75%, 80%, 85%, 90%, 91%, 92%, 93%, 94%, 95%, 96%, 97%, 98%, 99%, or 100% mature differentiated RPE cells.

The RPE cell cultures may be prepared in accordance with Good Manufacturing Practices (GMP) (e.g., the cultures are GMP-compliant) and/or current Good Tissue Practices (GTP) (e.g., the cultures may be GTP-compliant.)

Cryopreserved Preparations of RPE Cells

RPE cells may be frozen for storage. For example, portion of an RPE cell population may be analyzed using the methods described herein to detect the presence of any residual hES cells in the population, and the remainder of the population frozen for storage, thereby permitting determination of the approximate concentration of hES cells in the cell population. The frozen RPE cells may be associated with an indicator that indicates the number or concentration of hES cells detected in the population or otherwise indicates the result of the assay, e.g., an indicator that indicates that the cells have "passed" the test for hES cells contamination because the detected number or concentration of hES cells below an established release threshold, indicating that the cells are considered suitable for use.

The RPE cells may be stored by any appropriate method known in the art (e.g., cryogenically frozen) and may be frozen at any temperature appropriate for storage of the cells. For example, the cells may be frozen at about −20° C., −80° C., −120° C., −130° C., −135° C., −140° C., 150° C., −160° C., −170° C., −180° C., −190° C., −196° C., at any other temperature appropriate for storage of cells. Cryogenically frozen cells may be stored in appropriate containers and prepared for storage to reduce risk of cell damage and maximize the likelihood that the cells will survive thawing. RPE cells may be cryopreserved immediately following differentiation, following in vitro maturation, or after some period of time in culture. The RPE cells may also be maintained at room temperature, or refrigerated at, for example, about 4° C.

Similarly provided are methods of cryopreserving RPE cells. The RPE cells may be harvested, washed in buffer or media, counted, concentrated (via centrifugation), formulated in freezing media (e.g., 90% FBS/10% DMSO), or any combination of these steps. For example, the RPE cells may be seeded in several culture vessels and serially expanded. As the RPE cells are harvested and maintained in FBS at about 4° C. while several flasks of RPE cells are combined into a single lot. The RPE cells may be also washed with saline solution (e.g., DPBS) at least 1, 2, 3, 4, or 5 times.

Further, the RPE cells may be cryopreserved after dystrophin is organized at the cell membrane and PAX6 expression is low. In addition, the vials may be labeled, with a primary and/or secondary label. The information on the label may include the type of cell (e.g., hRPE cells), the lot number and date, the number of cells (e.g., $1\times10^6$ cells/mL), the expiration date (e.g., recommended date by which the vial should be used), manufacture information (e.g., name and address), warnings, and the storage means (e.g., storage in liquid nitrogen).

Cryopreserved RPE cell preparations described herein may comprise at least about 50,000-100,000 RPE cells. The cryopreserved RPE cell preparations may also comprise at least about 20,000-500,000 RPE cells. Also, the cryopreserved RPE cell preparations may comprise at least about 5,000, 10,000, 20,000, 30,000, 40,000, 50,000, 60,000, 75,000, 80,000, or 100,000 RPE cells. The cryopreserved RPE cell preparations may comprise at least about 1,000, 2,000, 3,000, 4,000, 5,000, 10,000, 20,000, 30,000, 40,000, 50,000, 60,000, 75,000, 80,000, 100,000, or 500,000 RPE cells. The cryopreserved RPE cell preparations may comprise at least about 1,000, 2,000, 3,000, 4,000, 5,000, 6,000, 7,000, 8,000, 9,000, $1\times10^4$, $2\times10^4$, $3\times10^4$, $4\times10^4$, $5\times10^5$, $6\times10^4$, $7\times10^4$, $8\times10^4$, $9\times10^4$, $1\times10^5$, $2\times10^5$, $3\times10^6$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^89$, $1\times10^9$, $2\times10^9$, $3\times10^9$, $4\times10^9$, $5\times10^9$, $6\times10^9$, $7\times10^9$, $8\times10^9$, $9\times10^9$, RPE cells. The RPE cells of the cryopreserved RPE cell preparations may be mammalian RPE cells, including human RPE cells.

Further, the cryopreserved RPE cell preparations described herein may comprise at least about 50,000-100,000 RPE cells/mL. The cryopreserved RPE cell preparations may also comprise at least about 20,000-500,000 RPE cells/mL. Also, the cryopreserved RPE cell preparations may comprise at least about 5,000, 10,000, 20,000, 30,000, 40,000, 50,000, 60,000, 75,000, 80,000, and 100,000 RPE cells/mL. The cryopreserved RPE cell preparations may comprise at least about 1,000, 2,000, 3,000, 4,000, 5,000, 10,000, 20,000, 30,000, 40,000, 50,000, 60,000, 75,000, 80,000, 100,000, or 500,000 RPE cells/mL. The cryopreserved RPE cell preparations may comprise at least about 1,000, 2,000, 3,000, 4,000, 5,000, 6,000, 7,000, 8,000, 9,000, $1\times10^4$, $2\times10^4$, $3\times10^4$, $4\times10^4$, $5\times10^5$, $6\times10^4$, $7\times10^4$, $8\times10^4$, $9\times10^4$, $1\times10^5$, $2\times10^5$, $3\times10^6$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^89$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ RPE cells/mL. The RPE cells of the cryopreserved RPE cell preparations may be mammalian RPE cells, including human RPE cells.

The RPE cells of the invention may be recovered from storage following cryopreservation. The RPE cells recovered from cryopreservation also maintain their viability and differentiation status. For example, at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the RPE cells may retain viability and differentiation following cryopreservation. Further, the RPE cells of the invention may be cryopreserved and maintain their viability after being stored for at least about 1, 2, 3, 4, 5, 6, or 7 days. The RPE cells of the invention may also be cryopreserved and maintain their viability after being stored for at least about 1, 2, 3, 4, 5, 6, 7, 8, 9, 10, 11, or 12 months. The RPE cells of the invention may be cryopreserved and maintain their viability after being stored for at least about 1, 2, 3, 4, 5, 6, or 7 years. For example, the RPE cells of the invention may be cryopreserved for at least about 4 years and show at least about 80% viability. The cryopreservation preparation comprising RPE cells may be substantially free of DMSO.

Methods of Producing RPE Cells

Cell populations analyzed by the subject methods may be produced from pluripotent stem cells. Cell types that may be produced include, but are not limited to, RPE cells, RPE progenitor cells, iris pigmented epithelial (IPE) cells, and other vision associated neural cells, such as internuncial neurons (e.g., "relay" neurons of the inner nuclear layer (INL)) and amacrine cells. Additionally, retinal cells, rods, cones, and corneal cells may be produced. Cells providing the vasculature of the eye may also be produced by the methods described herein.

Without being bound to a particular theory, the inventors found that the methods described herein may act through FGF, EGF, WNT4, TGF-beta, and/or oxidative stress to signal MAP-Kinase and potential C-Jun terminal Kinase pathways to induce the expression of the Paired-box 6 (PAX6) transcription factor. PAX6 acts synergistically with PAX2 to terminally differentiate mature RPE via the coordination of MITF and Otx2 to transcribe RPE-specific genes such as Tyrosinase (Tyr), and downstream targets such as RPE-65, Bestrophin, CRALBP, and PEDF. See WO 2009/051671, FIG. 1.

The RPE cells described herein may be differentiated from pluripotent stem cells, such as human embryonic stem cells, and may be molecularly distinct from embryonic stem cells, adult-derived RPE cells, and fetal-derived RPE cells. For example, the manufacturing process steps described herein may impart distinctive structural and functional characteristics to the final RPE cell product such that these cells closely resemble native RPE cells and are distinct from fetal derived RPE cells or RPE cell lines (e.g., APRE19).

An exemplary method for producing a RPE cell comprises: (a) providing pluripotent stem cells; (b) culturing the pluripotent stem cells as embryoid bodies in nutrient rich, low protein medium, wherein the medium optionally comprises serum free B-27 supplement; (c) culturing the embryoid bodies as an adherent culture in nutrient rich, low protein medium, wherein the medium optionally comprises serum free B-27 supplement; (d) culturing the adherent culture of cells of (c) in nutrient rich, low protein medium, wherein the medium does not comprise serum free B-27 supplement; (e) culturing the cells of (d) in medium capable of supporting growth of high-density somatic cell culture, whereby RPE cells appear in the culture of cells; (f) dissociating cells or clumps of cells from the culture of (e), preferably mechanically or chemically (e.g., using a protease or other enzyme, or another dissociation medium); (g) selecting the RPE cells from the culture and transferring the RPE cells to a separate culture containing medium supplemented with a growth factor to produce an enriched culture of RPE cells; and (g) propagating the enriched culture of RPE cells to produce a RPE cell. These method steps may be performed at least once to produce a substantially purified culture of RPE cells. Further, these method steps may be repeated at least 1, 2, 3, 4, 5, 6, 7, 8, 9, 10 or more times to produce more RPE cells.

Additionally, the invention also provides a method for producing a mature retinal pigment epithelial (RPE) cell comprising: (a) providing pluripotent stem cells; (b) culturing the pluripotent stem cells as embryoid bodies in nutrient rich, low protein medium, wherein the medium optionally comprises serum free B-27 supplement; (c) culturing the embryoid bodies as an adherent culture in nutrient rich, low protein medium, wherein the medium optionally comprises serum free B-27 supplement; (d) culturing the adherent culture of cells of step (c) in nutrient rich, low protein medium, wherein the medium does not comprise serum free B-27 supplement; (e) culturing the cells of (d) in medium capable of supporting growth of high-density somatic cell culture, whereby RPE cells appear in the culture of cells; (f) dissociating cells or clumps of cells from the culture of (e), preferably mechanically or chemically (e.g., using a protease or other enzyme, or another dissociation medium); (g) selecting the RPE cells from the culture and transferring the RPE cells to a separate culture containing medium supplemented with a growth factor to produce an enriched culture of RPE cells; (h) propagating the enriched culture of RPE cells; and (i) culturing the enriched culture of RPE cells to produce a mature RPE cell. These method steps may be performed at least once to produce a substantially purified culture of mature RPE cells. Further, these method steps may be repeated at least 1, 2, 3, 4, 5, 6, 7, 8, 9, 10 or more times to produce more mature RPE cells.

For any of the articulated steps, the cells may be cultured for at least about 1-10 weeks. For example, the cells may be cultured for at least about 3-6 weeks. For any of the articulated steps, the cells may be cultured for between about 1 days and 50 days, for example, for at least about 1-3, 3-4, 7, 4-9, 7-10, 7-12, 8-11, 9-12, 7-14, 14-21, and 3-45 days. The cells may be cultured for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days. The cells may be cultured for about 1, 2, 3, 4, 5, 6, 7, 8, 9, 10, 11, 12, 13, 14, 15, 16, 17, 18, 19, 20, 21, 22, 23, or 24 hours. For example, the cells may be cultured for 2-4 and 3-6 hours. For each of the above articulated method steps, the cells may be cultured for the same period of time at each step or for differing periods of time at one or more of the steps. Additionally, any of the above articulated method steps may be repeated to produce more RPE cells (e.g., scaled up to produce large numbers of RPE cells).

In the methods described herein, the RPE cells may begin to differentiate from amongst cells in the adherent culture of EBs. RPE cells may be visually recognized based on their cobblestone morphology and the initial appearance of pigmentation. As RPE cells continue to differentiate, clusters of RPE cells may be observed.

Mechanical or enzymatic methods may be used to select RPE cells from amongst clusters of non-RPE cells in a culture of embryoid body, or to facilitate sub-culture of adherent cells. Exemplary mechanical methods include, but are not limited to, titration with a pipette or cutting with a pulled needle. Exemplary enzymatic methods include, but are not limited to, any enzymes appropriate for disassociating cells (e.g., trypsin (e.g., Trypsin/EDTA), collagenase (e.g., collagenase B, collagenase IV), dispase, papain, mixture of collagenase and dispase, a mixture of collagenase and trypsin). A non-enzymatic solution may be used to disassociate the cells, such as a high EDTA-containing solution e.g., Hanks-based cell disassociation buffer.

The RPE cells may be differentiated from the embryoid bodies. Isolating RPE cells from the EBs allows for the expansion of the RPE cells in an enriched culture in vitro. For human cells, RPE cells may be obtained form EBs grown for less than 90 days. Further, RPE cells may arise in human EBs grown for at least about 7-14 days, 14-28 days, 28-45 days, or 45-90 days. The medium used to culture pluripotent stem cells, embryoid bodies, and RPE cells may be removed and/or replaced with the same or different media at any interval. For example, the medium may be removed and/or replaced after at least about 0-7 days, 7-10 days, 10-14 days, 14-28 days, or 28-90 days. Further, the medium may be replaced at least daily, every other day, or at least every 3 days.

To enrich for RPE cells and to establish substantially purified cultures of RPE cells, RPE cells may be dissociated from each other and from non-RPE cells using mechanical and/or chemical (including enzymatic) methods. A suspension of RPE cells may then be transferred to fresh medium and a fresh culture vessel to provide an enriched population of RPE cells.

RPE cells may be selected from the dissociated cells and cultured separately to produce a substantially purified culture of RPE cells. RPE cells are selected based on characteristics associated with RPE cells. For example, RPE cells can be recognized by cobblestone cellular morphology and pigmentation. In addition, there are several known markers of the RPE, including cellular retinaldehyde-binding protein (CRALBP), a cytoplasmic protein that is also found in apical microvilli; RPE65, a cytoplasmic protein involved in retinoid metabolism; bestrophin, the product of the Best vitelliform macular dystrophy gene (VMD2), and pigment epithelium derived factor (PEDF), a 48 kD secreted protein with angiostatic properties. The messenger RNA transcripts of these markers may be assayed using PCR (e.g., RT-PCR) or Northern blots. Also, the protein levels of these markers may be assaying using immunoblot technology or Western blots.

The RPE cells may also be selected based on cell function, such as by phagocytosis of shed rod and cone outer segments (or phagocytosis of another substrate, such as polystyrene beads), absorption of stray light, vitamin A metabolism, regeneration of retinoids, and tissue repair. Evaluation may also be performed by testing in vivo function after RPE cell implantation into a suitable host animal (such as a human or non-human animal suffering from a naturally occurring or induced condition of retinal degeneration), e.g., using behavioral tests, fluorescent angiography, histology, tight junctions conductivity, or evaluation using electron microscopy.

The enriched cultures of RPE cells may be cultured in appropriate medium, for example, EGM-2 medium. This, or a functionally equivalent or similar medium, may be supplemented with a growth factor or agent (e.g., bFGF, heparin, hydrocortisone, vascular endothelial growth factor, recombinant insulin-like growth factor, ascorbic acid, or human epidermal growth factor). The RPE cells may be phenotypically stable over a long period of time in culture (e.g., >6 weeks).

Pluripotent Stem Cells

The methods described herein may use differentiated cells (such as RPE cells) produced from pluripotent stem cells. Suitable pluripotent stem cells include but are not limited to embryonic stem cells, embryo-derived stem cells, and induced pluripotent stem cells, regardless of the method by which the pluripotent stem cells are derived. Pluripotent stem cells may be generated using, for example, methods known in the art. Exemplary pluripotent stem cells include embryonic stem cells derived from the inner cell mass (ICM) of blastocyst stage embryos, as well as embryonic stem cells derived from one or more blastomeres of a cleavage stage or morula stage embryo (optionally without destroying the remainder of the embryo). Such embryonic stem cells may be generated from embryonic material produced by fertilization or by asexual means, including somatic cell nuclear transfer (SCNT), parthenogenesis, cellular reprogramming, and androgenesis. Further, suitable pluripotent stem cells include but are not limited to human embryonic stem cells, human embryo-derived stem cells, and human induced pluripotent stem cells, regardless of the method by which the pluripotent stem cells are derived.

The pluripotent stem cells (e.g., hES cells) may be cultured as a suspension culture to produce embryoid bodies (EBs). The embryoid bodies may be cultured in suspension for about 7-14 days. However, in certain embodiments, the EBs may be cultured in suspension for fewer than 7 days (less than 7, 6, 5, 4, 3, 2, or less than 1 day) or greater than 14 days. The EBs may be cultured in medium supplemented with B-27 supplement.

After culturing the EBs in suspension culture, the EBs may be transferred to produce an adherent culture. For example, the EBs may be plated onto gelatin coated plates in medium. When cultured as an adherent culture, the EBs may be cultured in the same type of media as when grown in suspension. The media may not supplemented with B-27 supplement when the cells are cultured as an adherent culture. Also, the medium is supplemented with B-27 initially (e.g., for less than or equal to about 7 days), but then subsequently cultured in the absence of B-27 for the remainder of the period as an adherent culture. The EBs may be cultured as an adherent culture for at least about 14-28. However, in certain embodiments, the EBs may be cultured as an adherent culture for fewer than about 14 days (less than 14, 13, 12, 11, 10, 9, 8, 7, 6, 5, 4, 3, 2, or less than 1 day) or greater than about 28 days.

Human Embryonic Stem Cells

Human embryonic stem (hES) cells may be used as a pluripotent stem cell in the methods described herein. Human embryonic stem cells (hES) include progeny of the inner cell mass (ICM) of a blastocyst or cells derived from another source, and may remain pluripotent virtually indefinitely. The hES cells may be derived from one or more blastomeres of an early cleavage stage embryo, optionally without destroying or without harming the embryo. The hES cells may be produced using nuclear transfer. The hES cells may also be induced pluripotent cells (iPS cells) which are described in further detail below. Also, cryopreserved hES cells may be used. The hES cells may be cultured in any way known in the art, such as in the presence or absence of feeder cells. For example, the hES cells may be cultured in MDBK-GM, hESC Medium, INVITROGEN® Stem Cell Media, OptiPro SFM, VP-SFM, EGM-2, or MDBK-MM. See Stem Cell Information (Culture of Human Embryonic Stem Cells (hESC)) [NIH website, 2010]. The hES cells may be used and maintained in accordance with GMP standards.

When grown in culture on a feeder layer in defined conditions hES cells maintain a specific morphology, forming flat colonies comprised of small, tightly packed cells with a high ratio of nucleus to cytoplasm, clear boundaries between the cells, and sharp, refractile colony borders. hES cells express a set of molecular markers, such as Octamer binding protein 4 (Oct-4, a.k.a., Pou5f1), stage specific embryonic antigens (SSEA)-3 and SSEA-4, tumor rejection antigen (TRA)-1-60, TRA-1-80, alkaline phosphatase, NANOG, and Rex-1. Similar to the cells of the ICM that differentiate into predetermined lineages, hES cells in culture may be induced to differentiate. For example, hES cells may be differentiated into human RPE under the defined conditions described herein.

Human embryonic stem cells that may be used include, but are not limited to, MA01, MA04, MA09, ACT-4, MA03, H1, H7, H9, and H14. Additional exemplary cell lines include NED1, NED2, NED3, NED4, and NED5. See also NIH Human Embryonic Stem Cell Registry. An exemplary human embryonic stem cell line that may be used is MA09 cells. The isolation and preparation of MA09 cells was previously described in Klimanskaya, et al. (2006) "Human Embryonic Stem Cell lines Derived from Single Blastomeres." *Nature* 444: 481-485.

The hES cells may be initially co-cultivated with murine embryonic feeder cells (MEF) cells. The MEF cells may be mitotically inactivated by exposure to mitomycin C prior to seeding hES cells in co-culture, and thus the MEFs do not propagate in culture. Additionally, hES cell cultures may be examined microscopically and colonies containing non-hES cell morphology may be picked and discarded, e.g., using a stem cell cutting tool, by laser ablation, or other means. Typically, after the point of harvest of the hES cells for seeding for embryoid body formation no additional MEF cells are used in the process. The time between MEF removal and RPE cells described herein harvest may be a minimum of at least one, two, three, four, or five passages and at least about 5, 10, 20, 30, 40, 50, 60, 70, 80, 90, or 100 days in MEF-free cell culture. The time between MEF removal and harvesting the RPE cells may also be a minimum of at least about 3 passages and at least about 80-90 days in MEF-free cell culture. Due to the methods of production described herein, the RPE cell cultures and preparations described herein may be substantially free of mouse embryo fibroblasts (MEF) and human embryonic stem cells (hES).

Induced Pluripotent Stem Cells (iPS Cells)

Further exemplary pluripotent stem cells include induced pluripotent stem cells (iPS cells) generated by reprogramming a somatic cell by expressing or inducing expression of a combination of factors ("reprogramming factors"). iPS cells may be generated using fetal, postnatal, newborn, juvenile, or adult somatic cells. iPS cells may be obtained from a cell bank. Alternatively, iPS cells may be newly generated by methods known in the art prior to commencing differentiation to RPE cells or another cell type. The making of iPS cells may be an initial step in the production of differentiated cells. iPS cells may be specifically generated using material from a particular patient or matched donor with the goal of generating tissue-matched RPE cells. iPS cells can be produced from cells that are not substantially immunogenic in an intended recipient, e.g., produced from autologous cells or from cells histocompatible to an intended recipient.

The induced pluripotent stem cell may be produced by expressing or inducing the expression of one or more reprogramming factors in a somatic cell. The somatic cell is a fibroblast, such as a dermal fibroblast, synovial fibroblast, or lung fibroblast, or a non-fibroblastic somatic cell. The somatic cell is reprogrammed by expressing at least 1, 2, 3, 4, 5. The reprogramming factors may be selected from Oct 3/4, Sox2, NANOG, Lin28, c-Myc, and Klf4. Expression of the reprogramming factors may be induced by contacting the somatic cells with at least one agent, such as a small organic molecule agents, that induce expression of reprogramming factors.

The somatic cell may also be reprogrammed using a combinatorial approach wherein the reprogramming factor is expressed (e.g., using a viral vector, plasmid, and the like) and the expression of the reprogramming factor is induced (e.g., using a small organic molecule.) For example, reprogramming factors may be expressed in the somatic cell by infection using a viral vector, such as a retroviral vector or a lentiviral vector. Also, reprogramming factors may be expressed in the somatic cell using a non-integrative vector, such as an episomal plasmid. When reprogramming factors are expressed using non-integrative vectors, the factors may be expressed in the cells using electroporation, transfection, or transformation of the somatic cells with the vectors. For example, in mouse cells, expression of four factors (Oct3/4, Sox2, c-myc, and Klf4) using integrative viral vectors is sufficient to reprogram a somatic cell. In human cells, expression of four factors (Oct3/4, Sox2, NANOG, and Lin28) using integrative viral vectors is sufficient to reprogram a somatic cell.

Once the reprogramming factors are expressed in the cells, the cells may be cultured. Over time, cells with ES characteristics appear in the culture dish. The cells may be chosen and subcultured based on, for example, ES morphology, or based on expression of a selectable or detectable marker. The cells may be cultured to produce a culture of cells that resemble ES cells—these are putative iPS cells.

To confirm the pluripotency of the iPS cells, the cells may be tested in one or more assays of pluripotency. For example, the cells may be tested for expression of ES cell markers; the cells may be evaluated for ability to produce teratomas when transplanted into SCID mice; the cells may be evaluated for ability to differentiate to produce cell types of all three germ layers. Once a pluripotent iPS cell is obtained it may be used to produce RPE cells.

Engineering MHC Genes in Human Embryonic Stem Cells to Obtain Reduced-Complexity Differentiated Cells Human embryonic stem (hES) cells may be derived from a library of human embryonic stem cells. The library of human embryonic stem cells may comprise stem cells, each of which is hemizygous, homozygous, or nullizygous for at least one MHC allele present in a human population, wherein each member of said library of stem cells is hemizygous, homozygous, or nullizygous for a different set of MHC alleles relative to the remaining members of the library. The library of human embryonic stem cells may comprise stem cells that are hemizygous, homozygous, or nullizygous for all MHC alleles present in a human population. In the context of this invention, stem cells that are homozygous for one or more histocompatibility antigen genes include cells that are nullizygous for one or more (and in some embodiments, all) such genes. Nullizygous for a genetic locus means that the gene is null at that locus (i.e., both alleles of that gene are deleted or inactive.)

A hES cell may comprise modifications to one of the alleles of sister chromosomes in the cell's MHC complex. A variety of methods for generating gene modifications, such as gene targeting, may be used to modify the genes in the MHC complex. Further, the modified alleles of the MHC complex in the cells may be subsequently engineered to be homozygous so that identical alleles are present on sister chromosomes. Methods such as loss of heterozygosity (LOH) may be utilized to engineer cells to have homozygous alleles in the MHC complex. For example, one or more genes in a set of MHC genes from a parental allele can be targeted to generate hemizygous cells. The other set of MHC genes can be removed by gene targeting or LOH to make a null line. This null line can be used further as the embryonic cell line in which to drop arrays of the HLA genes, or individual genes, to make a hemizygous or homozygous bank with an otherwise uniform genetic background. Stem cells that are nullizygous for all MHC genes may be produced by standard methods known in the art, such as, for example, gene targeting and/or loss of heterozygosity (LOH). See, for example, United States Patent Application Publications 2004/0091936, 2003/0217374 and 2003/0232430, and U.S. Provisional Patent Application No. 60/729,173.

Accordingly, the present invention relates to methods of obtaining differentiated cells (such as RPE cells), including a library of differentiated cells having reduced MHC complexity. Differentiated cells with reduced MHC complexity may be used to increase the supply of available cells for therapeutic applications as it may eliminate the difficulties associated with patient matching. Such cells may be derived from stem cells that are engineered to be hemizygous or homozygous for genes of the MHC complex.

The invention also provides a library of differentiated cells (such as RPE cells and/or RPE lineage cells), wherein several lines of ES cells are selected and differentiated into the differentiated cells. These differentiated cells may be used for a patient in need of a cell-based therapy. The invention also provides a library of differentiated cells, each of which is hemizygous, homozygous, or nullizygous for at least one MHC allele present in a human population, wherein each member of said library of differentiated cells is hemizygous, homozygous, or nullizygous for a different set of MHC alleles relative to the remaining members of the library. The invention provides a library of human differentiated cells that are hemizygous, homozygous, or nullizygous for all MHC alleles present in a human population.

Culture Medium

Any medium that is capable of supporting high-density cultures may be used in the methods described herein, such as medium for viral, bacterial, or eukaryotic cell culture. For example, the medium may be high nutrient, protein-free medium or high nutrient, low protein medium. Further, the medium also may include nutrient components such as albumin, B-27® supplement, ethanolamine, fetuin, glutamine, insulin, peptone, purified lipoprotein material, sodium selenite, transferrin, vitamin A, vitamin C, or vitamin E. For example, nutrient rich, low protein medium may be any medium which supports the growth of cells in culture and has a low protein content. For example, nutrient rich, low protein media includes but is not limited to EX-CELL® MDBK-GM, OPTIPRO™ SFM, VP-SFM, DMEM, RPM1 Media 1640, IDMEM, MEM, F-12 nutrient mixture, F-10 nutrient mixture EGM-2, DMEM/F-12 media, media 1999, or EX-CELL® MDBK-MM. See also Table 2. Further, the nutrient rich, low protein medium may be a medium that does not support the growth or maintenance of embryonic stem cells.

When low protein medium is used, the medium may contain at least about 20%, 19%, 18%, 17%, 16%, 15%, 14%, 13%, 12%, 11%, 10%, 9%, 8%, 7%, 6%, 5%, 4%, 3%, 2.5%, 2%, 1.5%, 1%, 0.75%, 0.5%, 0.25%, 0.20%, 0.10%, 0.05%, 0.02%, 0.016%, 0.015%, or 0.010% animal-derived protein (e.g., 10% FBS). Note that reference to the percentage of protein present in low protein medium refers to the medium alone and does not account for protein present in, for example, B-27® supplement. Thus, it is understood that when cells are cultured in low protein medium and B-27® supplement, the percentage of protein present in the medium may be higher.

The low protein or protein free medium are supplemented with serum free B-27® supplement. Nutrient components of B-27® supplement may comprise biotin, L-carnitine, corticosterone, ethanolamine, D+-galactose, reduced glutathione, linoleic acid, linolenic acid, progesterone, putrescine, rednyl acetate, selenium, triodo-1-thyronine (T3), DL-alpha-iocopherol (vitamin E), DL-alpha-tocopherol acetate, bovine serum albumin, catalase, insulin, superoxide dismutase, and transferrin. When cells are cultured in protein free medium supplemented with B-27®, protein free refers to the medium prior to addition of B-27®.

Growth factors, agents, and other supplements described herein may be used alone or in combination with other factors, agents, or supplements for inclusion in media. Factors, agents, and supplements may be added to the media immediately, or any time during or after cell culture.

The medium may also contain supplements such as heparin, hydrocortisone, ascorbic acid, serum (e.g., fetal bovine serum), or a growth matrix (e.g., extracellular matrix from bovine corneal epithelium, MATRIGEL® (basement membrane matrix), or gelatin), fibronectin, proteolytic fragments of fibronectin, laminin, thrombospondin, aggrecan, and syndezan.

The culture media may be supplemented with one or more factors or agents.

Growth factors that may be used include, for example, EGF, FGF, VEGF, and recombinant insulin-like growth factor. Growth factors that may be used in the present invention also include 6Ckine (recombinant), activin A, α-interferon, alpha-interferon, amphiregulin, angiogenin, β-endothelial cell growth factor, beta cellulin, β-interferon, brain derived neurotrophic factor, cardiotrophin-1, ciliary neurotrophic factor, cytokine-induced neutrophil chemoattractant-1, endothelial cell growth supplement, eotaxin, epidermal growth factor, epithelial neutrophil activating peptide-78, erythropoietin, estrogen receptor-α, estrogen receptor-β, fibroblast growth factor (acidic/basic, heparin stabilized, recombinant), FLT-3/FLK-2 ligand (FLT-3 ligand), gamma-interferon, glial cell line-derived neurotrophic factor, Gly-His-Lys, granulocyte colony-stimulating factor, granulocyte macrophage colony-stimulating factor, GRO-alpha/MGSA, GRO-B, GRO-gamma, HCC-1, heparin-binding epidermal growth factor like growth factor, hepatocyte growth factor, heregulin-alpha (EGF domain), insulin growth factor binding protein-1, insulin-like growth factor binding protein-1/IGF-1 complex, insulin-like growth factor, insulin-like growth factor II, 2.5S nerve growth factor (NGF), 7S-NGF, macrophage inflammatory protein-1β, macrophage inflammatory protein-2, macrophage inflammatory protein-3 α, macrophage inflammatory protein-3β, monocyte chemotactic protein-1, monocyte chemotactic protein-2, monocyte chemotactic protein-3, neurotrophin-3, neurotrophin-4, NGF-β (human or rat recombinant), oncostatin M (human or mouse recombinant), pituitary extract, placenta growth factor, platelet-derived endothelial cell growth factor, platelet-derived growth factor, pleiotrophin, rantes, stem cell factor, stromal cell-derived factor 1B/pre-B cell growth stimulating factor, thrombopoietin, transforming growth factor alpha, transforming growth factor-β1, transforming growth factor-β2, transforming growth factor-β3, transforming growth-factor-β5, tumor necrosis factor (α and β), and vascular endothelial growth factor.

Agents that may be used according to the present invention include cytokines such as interferon-α, interferon-α A/D, interferon-β, interferon-γ, interferon-γ-inducible protein-10, interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-15, interleukin-17, keratinocyte growth factor, leptin, leukemia inhibitory factor, macrophage colony-stimulating factor, and macrophage inflammatory protein-1 α.

The culture media may be supplemented with hormones and hormone antagonists, including but not limited to 17B-estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagon, gonadotropin, hydrocortisone, insulin, insulin-like growth factor binding protein, L-3,3',5'-triiodothyronine, L-3,3',5'-triiodothyronine, leptin, leutinizing hormone, L-thyroxine, melatonin, MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxine-binding globulin, and vasopressin. The culture media may be supplemented with antibodies to various factors including but not limited to anti-low density lipoprotein receptor antibody, anti-progesterone receptor, internal antibody, anti-alpha interferon receptor chain 2 antibody, anti-c-c chemokine receptor 1 antibody, anti-CD 118 antibody, anti-CD 119 antibody, anti-colony stimulating factor-1 antibody, anti-CSF-1 receptor/c-fins antibody, anti-epidermal growth factor (AB-3) antibody, anti-epidermal growth factor receptor antibody, anti-epidermal growth factor receptor, phospho-specific antibody, anti-epidermal growth factor (AB-1) antibody, anti-erythropoietin receptor antibody, anti-estrogen receptor antibody, anti-estrogen receptor, C-terminal antibody, anti-estrogen receptor-B antibody, anti-fibroblast growth factor receptor antibody, anti-fibroblast growth factor, basic antibody, anti-gamma-interferon receptor chain antibody, anti-gamma-interferon human recombinant antibody, anti-GFR alpha-1 C-terminal antibody, anti-GFR alpha-2 C-terminal antibody, anti-granulocyte colony-stimulating factor (AB-1) antibody, anti-granulocyte colony-stimulating factor receptor antibody, anti-insulin receptor antibody, anti-insulin-like growth factor-1 receptor antibody, anti-interleukin-6 human recombinant antibody, anti-interleukin-1 human recombinant antibody, anti-interleukin-2 human recombinant antibody, anti-leptin mouse recombinant antibody, anti-nerve growth factor receptor antibody, anti-p60, chicken antibody, anti-parathyroid hormone-like protein antibody, anti-platelet-derived growth factor receptor antibody, anti-platelet-derived growth factor receptor-B antibody, anti-platelet-derived growth factor-alpha antibody, anti-progesterone receptor antibody, anti-retinoic acid receptor-alpha antibody, anti-thyroid hormone nuclear receptor antibody, anti-thyroid hormone nuclear receptor-alpha 1/Bi antibody, anti-transfesferin receptor/CD71 antibody, anti-transforming growth factor-alpha antibody, anti-transforming growth factor-B3 antibody, anti-rumor necrosis factor-alpha antibody, and anti-vascular endothelial growth factor antibody.

Exemplary growth media suitable for use in the methods described herein are listed in Table 2.

TABLE 2

Growth Media Formulations.

| NAME OF MEDIUM | FORMULATION |
| --- | --- |
| MEF Growth (MEF-GM) | 500 mL of IMDM |
| | 55 mL FBS |
| hES Growth (hES- GM) | 200 mL KNOCKOUT ® D-MEM |
| | 30 mL KNOCKOUT ® Serum Replacement |
| | 2 mL GLUTAMAX ®-I |
| | 2 mL NEAA |
| | 200 μL 2-mercaptoethanol |
| | 10 ng/mL bFGF |
| | 10 ng/mL LIF |
| EB Growth (EB-GM) | 1 L EX-CELL ® MDBK-GM |
| | 16.5 mL GLUTAMAX ®-I |
| | or |
| | 1 L OPTIPRO™-SFM |
| | 20 mL GLUTAMAX ®-I |
| EB Formation (EB-FM) | 1 L EX-CELL ® MDBK-GM |
| | 16.5 mL GLUTAMAX ®-I |
| | 20 mL B-27® Supplement |
| | or |
| | 1 L OPTIPRO™-SFM |
| | 20 mL GLUTAMAX ®-I |
| | 20 mL B-27® Supplement |
| RPE Maintenance (RPE-MM) | 1 L EX-CELL ® MDBK-MM |
| | 20 mL GLUTAMAX ®-I |
| | or |
| | 1 L VP-SFM |
| | 20 mL GLUTAMAX ®-I |
| RPE Growth (RPE-GM) | 500 mL EBM ®-2 (cell culture basal media for endothelial cells) |
| | 10 mL FBS |
| | 0.2 mL hydrocortisone |
| | 2.0 mL rhFGF-B |
| | 0.5 mL R3-IGF-1 |
| | 0.5 mL ascorbic Acid |
| | 0.5 mL rhEGF |
| | 0.5 mL heparin |
| | 0.5 mL VEGF |

Retinal Pigment Epithelium (RPE)

The retinal pigment epithelium (RPE) is the pigmented cell layer outside the neurosensory retina between the underlying choroid (the layer of blood vessels behind the retina) and overlying retinal visual cells (e.g., photoreceptors—rods and cones). The RPE is critical to the function and health of photoreceptors and the retina. The RPE maintains photoreceptor function by recycling photopigments, delivering, metabolizing, and storing vitamin A, phagocytosing rod photoreceptor outer segments, transporting iron and small molecules between the retina and choroid, maintaining Bruch's membrane and absorbing stray light to allow better image resolution. Engelmann and Valtink (2004) "RPE Cell Cultivation." *Graefe's Archive for Clinical and Experimental Ophthalmology* 242(1): 65-67; See also Irina Klimanskaya, *Retinal Pigment Epithelium Derived From Embryonic Stem Cells, in* STEM CELL ANTHOLOGY 335-346 (Bruce Carlson ed., 2009).

Mature RPE is characterized by its cobblestone cellular morphology of black pigmented cells and RPE cell markers including cellular retinaldehyde-binding protein (CRALBP), a 36-kD cytoplasmic retinaldehyde-binding protein that is also found in apical microvilli (Eisenfeld, et al. (1985) *Experimental Research* 41(3): 299-304); RPE65, a 65 kD cytoplasmic protein involved in retinoid metabolism (Ma, et al. (2001) *Invest Opthalmol Vis Sci.* 42(7): 1429-35; Redmond (2009) *Exp Eye Res.* 88(5): 846-847); bestrophin, a membrane localized 68 kD product of the Best vitelliform macular dystrophy gene (VMD2) (Marmorstein, et al. (2000) *PNAS* 97(23): 12758-12763), and pigment epithelium derived factor (PEDF), a 48-kD secreted protein with angiostatic properties (Karakousis, et al. (2001) *Molecular Vision* 7: 154-163; Jablonski, et al. (2000) *The Journal of Neuroscience* 20(19): 7149-7157).

Diseases of the Retina

Degeneration of the RPE can cause retinal detachment, retinal dysplasia, or retinal atrophy that is associated with a number of vision-altering ailments that result in photoreceptor damage and blindness, such as choroideremia, diabetic retinopathy, macular degeneration (including age-related macular degeneration), retinitis pigmentosa, and Stargardt's Disease (fundus flavimaculatus). WO 2009/051671.

Choroideremia. Choroideremia is an X-linked recessive retinal degenerative disease that leads to the degeneration of the choriocapillaris, the retinal pigment epithelium, and the photoreceptor of the eye caused by mutations in the CHM gene, which encodes the Rab escort protein-1 (REP-1). Genetics Home Reference (U.S. National Library of Medicine) [Oct. 17, 2010].

Diabetic Retinopathy. Diabetic retinopathy is the most common diabetic eye disease and a leading cause of blindness in the United States. Diabetic retinopathy is caused by changes in the blood vessels of the retina. Generally, diabetic retinopathy may only be controlled or slowed with surgery but not treated, and the patient usually continues to suffer from vision problems. Therefore, there exists a need for improved diabetic retinopathy therapies. "Diabetic Retinopathy" (MayoClinic.org) [Feb. 11, 2010].

Macular Degeneration. Age-related macular degeneration (AMD) is the most common reason for legal blindness in the United States and Europe. Atrophy of the submacular RPE and the development of choroidal neovascularizations (CNV) results secondarily in loss of central visual acuity. Early signs of AMD are deposits (druses) between retinal pigment epithelium and Bruch's membrane. Central geographic atrophy ("dry AMD") results from atrophy to the retinal pigment epithelial layer below the retina, which causes vision loss through loss of photoreceptors (rods and cones) in the central part of the eye. Neovascular or exudative AMD ("wet AMD") causes vision loss due to abnormal blood vessel growth (choroidal neovascularization) in the choriocapillaris, through Bruch's membrane, ultimately leading to blood and protein leakage below the macula. Bleeding, leaking, and scarring from these blood vessels eventually cause irreversible damage to the photoreceptors and rapid vision loss if left untreated. Current treatments for macular degeneration include anti-angiogenic therapy with ranibizumab (LUCENTIS®) or bevacizumab (AVASTIN®), photocoagulation (laser surgery), photodynamic therapy with verteporfin (VISUDYNE®), and submacular hemorrhage displacement surgery. "Macular Degeneration." (MayoClinic.org) [October 2010]. However, the goal of these therapies is to stem further vision loss and, unfortunately, existing damage cannot be reversed. Therefore, a great need exists for the treatment of macular degeneration.

Retinitis Pigmentosa (RP). Retinitis pigmentosa (RP) is a group of inherited diseases that damage the photoreceptors (e.g., rods and cones) in the retina affecting approximately 1.5 million people worldwide. For example, autosomal recessive RP is caused by mutations in cis retinaldehyde binding protein or RPE65. The progression of RP is slow and varies from patient to patient. Patients with RP all suffer some vision loss, with night blindness as a typical early symptom followed by tunnel vision, and some may lose all sight. "Retinitis Pigmentosa." *American Optometric Association* (October 2010). Although treatment with vitamin A and lutein has shown some promise in slowing the progress of RP, no effective treatment is available.

Retinal Detachment. Retinal detachment, including rhegmatogenous retinal detachment, exudative, serous, or secondary retinal detachment, and tractional retinal detachment, is a disorder of the eye in which the retina peels away from its underlying layer of support tissue, which can lead to vision loss and blindness. See Ghazi and Green (2002) *Eye* 16: 411-421; Facts About Retinal Detachment [NEI Health Information](October 2010). A need exists for a treatment for retinal detachment.

Stargardt's Disease (fundus flavimaculatus). Stargardt's Disease (fundus flavimaculatus) is a type of macular degeneration, including both an autosomal recessive and a dominant form, that causes a progressive loss of central vision of both eyes. See Gass and Hummer (1999) *Retina* 19(4): 297-301 and Aaberg (1986) *Tr. Am. Ophth. Soc.* LXXXIV: 453-487. Currently, there are no treatments available for Stargardt's Disease.

RPE Cells in Medicine

Given the importance of the RPE in maintaining visual and retinal health, the RPE and methodologies for producing RPE cells in vitro are of considerable interest. See Lund, et al. (2001) *Progress in Retinal and Eye Research* 20(4): 415-449. For example, a study reported in Gouras, et al. (2002) *Investigative Ophthalmology & Visual Science* 43(10): 3307-311 describes the transplantation of RPE cells from normal mice into transgenic RPE65$^{-/-}$ mice (a mouse model of retinal degeneration). Gouras discloses that the transplantation of healthy RPE cells slowed the retinal degeneration in the RPE65$^{-/-}$ mice but after 3.7 weeks, its salubrious effect began to diminish. Treumer, et al. (2007) *Br J Opthalmol* 91: 349-353 describes the successfully transplantation of autologous RPE-choroid sheet after removal of a subfoveal choroidal neovascularization (CNV) in patients with age related macular degeneration (AMD), but this procedure only resulted in a moderate increase in mean visual acuity.

Moreover, RPE cells have been suggested as a possible therapy for treating Parkinson's disease, a chronic degenerative disease of the brain. The disease is caused by degeneration of specialized neuronal cells in the region of the basal ganglia. The death of dopaminergic neurons results in reduced synthesis of dopamine, an important neurotransmitter, in patients with Parkinson's disease. Ming and Le (2007) *Chinese Medical Journal* 120(5): 416-420 suggests the transplantation of RPE cells from eye donors into the striatum of Parkinson's patients to supply beneficial neurotrophic and anti-inflammatory cytokines to treat Parkinson's' disease.

However, RPE cells sourced from human donors has several intractable problems. First is the shortage of eye donors, and the current need is beyond what could be met by donated eye tissue. Second, the RPE cells from human donors may be contaminated with pathogens and may have genetic defects. Third, donated RPE cells are derived from cadavers, which may not be of sufficient quality as to be useful in transplantation. For example, cadaver-sourced RPE may have age-associated defects including being close to senesce. Additionally, RPE cells derived from fetal tissue have shown a very low proliferative potential. Further, cadaver-sourced RPE cells vary widely from batch to batch and must be characterized for safety before transplantation. See, e.g., Irina Klimanskaya, *Retinal Pigment Epithelium Derived From Embryonic Stem Cells, in* STEM CELL ANTHOLOGY 335-346 (Bruce Carlson ed., 2009). Sourcing RPE cells from human donors also may incur donor consent problems and regulatory obstacles, complicating the harvesting and use of RPE cells for therapy. In AMD patients and elderly patients also suffer from degeneration of the Bruch's membrane, complicating RPE cell transplantation. See Gullapalli, et al. (2005) *Exp Eye Res.* 80(2): 235-48.

Therapeutic use of autologous RPE cells (obtained from a patient's "good" eye) has also been attempted in limited trials but has proven unsatisfactory. Autologous cells are fundamentally limited because the autologous cells carry the same genetic propensities that may have lead to the development of AMD. See, e.g., Binder, et al. (2007) *Progress in Retinal and Eye Research* 26(5): 516-554. Additionally, autologous RPE cells have limited proliferative capacity (particularly because AMD most frequently develops in older patients) which limits their utility in therapeutic applications (e.g., the RPE cells may not transplant well and are less likely to last long enough for more complete recovery of vision).

Embryonic Stem Cells Derived RPE Cells (hESC-RPE Cells)

Human embryonic stem cells (hES) are considered a promising source of replacement RPE cells for clinical use. See Idelson, et al. (2009) *Cell Stem Cell* 5: 396-408. However, numerous problems continue to plague their use as therapeutics, including the risk of teratoma formation and the need for powerful immunosuppressive drugs to overcome the problems with immune rejection. For example, Wang, et al. (2010) *Transplantation* describes a study where mouse embryonic stem cells were differentiated into RPE cells and then transplanted into a mouse model of retinitis pigmentosa ($Rpe65^{rd12}/Rpe^{rd12}$ C57BL6 mice). Although the $Rpe65^{rd12}/Rpe^{rd12}$ mice receiving the RPE cell transplants did show significant visual recovery during a 7-month period, this was complicated by retinal detachments and tumors.

Further, the transition from basic research to clinical application is precluded by the need to adhere to guidelines set forth by the U.S. Food and Drug Administration, collectively referred to as current Good Manufacturing Practices (GMP) and current Good Tissue Practices (GTP). In the context of clinical manufacturing of a cell therapy product, such as hES cell-derived RPE, GTP governs donor consent, traceability, and infectious disease screening, whereas the GMP is relevant to the facility, processes, testing, and practices to produce a consistently safe and effective product for human use. Lu, et al. Stem Cells 27: 2126-2135 (2009). Thus, there exists a need for a systematic, directed manner for the production of large numbers of RPE cells suitable for use in transplantation therapies.

Patents and applications owned by the assignee of the present applications have disclosed methods of producing RPE cells through differentiation of embryonic stem cells in U.S. Pat. Nos. 7,795,025, 7,794,704, and 7,736,896, U.S. Ser. No. 12/682,712, as well as PCT Application no. PCT/US10/57056, filed Nov. 17, 2010 (now published as WO 2011/063005) and entitled "Methods of Producing Human RPE Cells and Pharmaceutical Preparations of Human RPE Cells", and U.S. Provisional Patent Application No. 61/262,002, filed Nov. 17, 2009, each of which is hereby incorporated by reference in its entirety.

Therapeutic Methods

The RPE cells and pharmaceutically preparations comprising RPE cells produced by the methods described herein may be used for cell-based treatments. The invention provides methods for treating a condition involving retinal degeneration comprising administering an effective amount of a pharmaceutical preparation comprising RPE cells, wherein the RPE cells are derived from pluripotent stem cells in vitro. Conditions involving retinal degeneration include, for example, choroideremia, diabetic retinopathy, retinal atrophy, retinal detachment, retinal dysplasia, and retinitis pigmentosa. The RPE cells described herein may also be used in methods for treating macular degeneration including but are not limited to age related macular degeneration (dry or wet), North Carolina macular dystrophy, Sorsby's fundus dystrophy, Stargardt's disease, pattern dystrophy, Best disease, malattia leventinese. Doyne's honeycomb choroiditis, dominant drusen, and radial drusen. The RPE cells described herein may also be used in methods of treating Parkinson's disease (PD).

A common feature of cell transplantation is low graft survival, for example, in many cell transplantation studies there tends to be a loss of cells immediately following transplantation (e.g., within the first week). This loss of cells does not appear to be due to rejection of the transplanted cells but rather an inability of a certain percentage of the cells to be retained at the transplant site. This lack of cell retention is most likely due to a number of factors such as the failure of the cells to attach to an underlying structure, a lack of sufficient nutrients, or physical stresses at the transplant site. Following this initial drop-off of cell number, the cell survival at various time after transplantation can vary considerably from study to study. Thus, although some studies show a steady decline in numbers, other show results where the grafted cells can reach a stable number. However, an important factor in considering the success of a transplantation is the percentage of recipients with surviving grafts following cell transplant.

In contrast with previous preparations, the RPE cells in the pharmaceutical preparations described herein may survive long term following transplantation. For example, the RPE cells may survive at least about 1, 2, 3, 4, 5, 6, 7, 8, 9, or 10 days. Additionally, the RPE cells may survive at least about 1, 2, 3, 4, 5, 6, 7, 8, 9, or 10 weeks; at least about 1, 2, 3, 4, 5, 6, 7, 8, 9, or 10 months; or at least about 1, 2, 3, 4, 5, 6, 7, 8, 9, or 10 years. Further, the RPE cells may survive throughout the lifespan of the receipt of the transplant. Additionally, at least 10, 20, 30, 40, 50, 60, 70, 80, 90, 95, 96, 97, 98, 99, or 100% of the receipts of RPE cells described herein may show survival of the transplanted RPE cells. Further, the RPE cells described herein may successfully incorporate into the RPE layer in the transplantation receipt, forming a semi-continuous line of cells and retain expression of key RPE molecular markers (e.g., RPE65 and bestrophin). The RPE cells described herein may also attach to the Bruch's membrane, forming a stable RPE layer in the transplantation receipt. Also, the RPE cells described herein are substantially free of ES cells and the transplantation receipts does not show abnormal growth or tumor formation at the transplantation site.

The methods of treating a patient suffering from a condition associated with retinal degeneration may comprise administering a composition of the invention locally (e.g., by intraocular injection or insertion of a matrix comprising the pharmaceutical preparation of the invention). Intraocular administration of pharmaceutical preparation of the invention include, for example, delivery into the vitreous body, transcorneally, sub-conjunctival, juxtascleral, posterior scleral, and sub-tenon portions of the eye. See, for example, U.S. Pat. Nos. 7,794,704; 7,795,025; 6,943,145; and 6,943,153.

The invention also provides a method of administering human RPE cells that have been derived from reduced-complexity embryonic stem cells to a patient. This method may comprise: (a) identifying a patient that needs treatment involving administering human RPE cells to him or her; (b) identifying MHC proteins expressed on the surface of the patient's cells; (c) providing a library of human RPE cells of reduced MHC complexity made by the method for producing RPE cells of the present invention; (d) selecting the RPE cells from the library that match this patient's MHC proteins on his or her cells; (e) administering any of the cells from step (d) to said patient. This method may be performed in a regional center, such as, for example, a hospital, a clinic, a physician's office, and other health care facilities. Further, the RPE cells selected as a match for the patient, if stored in small cell numbers, may be expanded prior to patient treatment.

The RPE cells may be cultured under conditions to increase the expression of alpha integrin subunits 1-6 or 9 as compared to uncultured RPE cells or other RPE cell preparations prior to transplantation. The RPE cells described herein may be cultured to elevate the expression level of alpha integrin subunits 1, 2, 3, 4, 5, 6, or 9. The RPE cells described herein may be cultured under conditions that promote the expression of alpha integrin subunits 1-6. For example, the RPE cells may be cultured with integrin-activating agents including but not limited to manganese and the activating monoclonal antibody (mAb) TS2/16. See Afshari, et al. Brain (2010) 133(2): 448-464.

The particular treatment regimen, route of administration, and adjuvant therapy may be tailored based on the particular condition, the severity of the condition, and the patient's overall health. Administration of the pharmaceutical preparations comprising RPE cells may be effective to reduce the severity of the symptoms and/or to prevent further degeneration in the patient's condition. For example, administration of a pharmaceutical preparation comprising RPE cells may improve the patient's visual acuity. Additionally, in certain embodiments, administration of the RPE cells may be effective to fully restore any vision loss or other symptoms. Further, the RPE cell administration may treat the symptoms of injuries to the endogenous RPE layer.

Pharmaceutical Preparations of RPE Cells

The RPE cells may be formulated with a pharmaceutically acceptable carrier. For example, RPE cells may be administered alone or as a component of a pharmaceutical formulation. The subject compounds may be formulated for administration in any convenient way for use in medicine. Pharmaceutical preparations suitable for administration may comprise the RPE cells, in combination with one or more pharmaceutically acceptable sterile isotonic aqueous or non-aqueous solutions (e.g., balanced salt solution (BSS)), dispersions, suspensions or emulsions, or sterile powders which may be reconstituted into sterile injectable solutions or dispersions just prior to use, which may contain antioxidants, buffers, bacteriostats, solutes or suspending or thickening agents.

When administered, the pharmaceutical preparations for use in this invention may be in a pyrogen-free, physiologically acceptable form. The preparation comprising RPE cells used in the methods described herein may be transplanted in a suspension, gel, colloid, slurry, or mixture. Further, the preparation may desirably be encapsulated or injected in a viscous form into the vitreous humor for delivery to the site of retinal or choroidal damage. Also, at the time of injection, cryopreserved RPE cells may be may be resuspended with commercially available balanced salt solution to achieve the desired osmolality and concentration for administration by subretinal injection.

The RPE cells of the invention may be delivered in a pharmaceutically acceptable ophthalmic formulation by intraocular injection. When administering the formulation by intravitreal injection, for example, the solution may be concentrated so that minimized volumes may be delivered. Concentrations for injections may be at any amount that is effective and non-toxic, depending upon the factors described herein. The pharmaceutical preparations of RPE cells for treatment of a patient may be formulated at doses of at least about $10^4$ cells/mL. The RPE cell preparations for treatment of a patient are formulated at doses of at least about $10^3$, $10^4$, $10^5$, $10^6$, $10^7$, $10^8$, $10^9$, or $10^{10}$ RPE cells/mL. For example, the RPE cells may be formulated in a pharmaceutically acceptable carrier or excipient.

The pharmaceutical preparations of RPE cells described herein may comprise at least about 1,000; 2,000; 3,000; 4,000; 5,000; 6,000; 7,000; 8,000; or 9,000 RPE cells. The pharmaceutical preparations of RPE cells may comprise at least about $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ RPE cells. The pharmaceutical preparations of RPE cells may comprise at least about $1\times10^2$-$1\times10^3$, $1\times10^2$-$1\times10^4$, $1\times10^4$-$1\times10^5$, or $1\times10^3$-$1\times10^6$ RPE cells. The pharmaceutical preparations of RPE cells may comprise at least about 10,000, 20,000, 25,000, 50,000, 75,000, 100,000, 125,000, 150,000, 175,000, 180,000, 185,000, 190,000, or 200,000 RPE cells. For example, the pharmaceutical preparation of RPE cells may comprise at least about 20,000-200,000 RPE cells in a volume at least about 50-200 µL. Further, the pharmaceutical preparation of RPE cells may comprise at least about 180,000 RPE cells in a volume at least about 150 µL.

RPE cells may be formulated for delivery in a pharmaceutically acceptable ophthalmic vehicle, such that the preparation is maintained in contact with the ocular surface for a sufficient time period to allow the cells to penetrate the affected regions of the eye, as for example, the anterior chamber, posterior chamber, vitreous body, aqueous humor, vitreous humor, cornea, iris/ciliary, lens, choroid, retina, sclera, suprachoroidal space, conjunctiva, subconjunctival space, episcleral space, intracorneal space, epicorneal space, pars plana, surgically-induced avascular regions, or the macula.

The volume of preparation administered according to the methods described herein may dependent on factors such as the mode of administration, number of RPE cells, age and weight of the patient, and type and severity of the disease being treated. If administered by injection, the volume of a pharmaceutical preparations of RPE cells of the invention may be from at least about 1, 1.5, 2, 2.5, 3, 4, or 5 mL. The volume may be at least about 1-2 mL. For example, if administered by injection, the volume of a pharmaceutical preparations of RPE cells of the invention may be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 100, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 µL (microliters). For example, the volume of a preparation of the invention may be from at least about 10-50, 20-50, 25-50, or 1-200 µL. The volume of a preparation of the invention may be at least about 10, 20, 30, 40, 50, 100, 110, 120, 130, 140, 150, 160, 170, 180, 190, or 200 µL.

For example, the preparation may comprise at least about $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, or $9 \times 10^4$ RPE cells per µL. The preparation may comprise 2000 RPE cells per µL, for example, 100,000 RPE cells per 50 µL or 180,000 RPE cells per 90 µL.

The method of treating retinal degeneration may further comprise administration of an immunosuppressant. Immunosuppressants that may be used include but are not limited to anti-lymphocyte globulin (ALG) polyclonal antibody, anti-thymocyte globulin (ATG) polyclonal antibody, azathioprine, BASILIXIMAB® (anti-IL-2Rα receptor antibody), cyclosporin (cyclosporin A), DACLIZUMAB® (anti-IL-2Rα receptor antibody), everolimus, mycophenolic acid, RITUXIMAB® (anti-CD20 antibody), sirolimus, and tacrolimus. The immunosuppressants may be dosed at least about 1, 2, 4, 5, 6, 7, 8, 9, or 10 mg/kg. When immunosuppressants are used, they may be administered systemically or locally, and they may be administered prior to, concomitantly with, or following administration of the RPE cells. Immunosuppressive therapy continues for weeks, months, years, or indefinitely following administration of RPE cells. For example, the patient may be administered 5 mg/kg cyclosporin for 6 weeks following administration of the RPE cells.

The method of treatment of retinal degeneration may comprise the administration of a single dose of RPE cells. Also, the methods of treatment described herein may comprise a course of therapy where RPE cells are administered multiple times over some period. Exemplary courses of treatment may comprise weekly, biweekly, monthly, quarterly, biannually, or yearly treatments. Alternatively, treatment may proceed in phases whereby multiple doses are required initially (e.g., daily doses for the first week), and subsequently fewer and less frequent doses are needed.

If administered by intraocular injection, the RPE cells may be delivered one or more times periodically throughout the life of a patient. For example, the RPE cells may be delivered once per year, once every 6-12 months, once every 3-6 months, once every 1-3 months, or once every 1-4 weeks. Alternatively, more frequent administration may be desirable for certain conditions or disorders. If administered by an implant or device, the RPE cells may be administered one time, or one or more times periodically throughout the lifetime of the patient, as necessary for the particular patient and disorder or condition being treated. Similarly contemplated is a therapeutic regimen that changes over time. For example, more frequent treatment may be needed at the outset (e.g., daily or weekly treatment). Over time, as the patient's condition improves, less frequent treatment or even no further treatment may be needed.

The methods described herein may further comprises the step of monitoring the efficacy of treatment or prevention by measuring electroretinogram responses, optomotor acuity threshold, or luminance threshold in the subject. The method may also comprise monitoring the efficacy of treatment or prevention by monitoring immunogenicity of the cells or migration of the cells in the eye.

The RPE cells may be used in the manufacture of a medicament to treat retinal degeneration. The invention also encompasses the use of the preparation comprising RPE cells in the treatment of blindness. For example, the preparations comprising human RPE cells may used to treat retinal degeneration associated with a number of vision-altering ailments that result in photoreceptor damage and blindness, such as, diabetic retinopathy, macular degeneration (including age-related macular degeneration, e.g., wet age-related macular degeneration and dry age-related macular degeneration), retinitis pigmentosa, and Stargardt's Disease (fundus flavimaculatus). The preparation may comprise at least about 5,000-500,000 RPE cells (e.g., 100,00 RPE cells) which may be administered to the retina to treat retinal degeneration associated with a number of vision-altering ailments that result in photoreceptor damage and blindness, such as, diabetic retinopathy, macular degeneration (including age-related macular degeneration), retinitis pigmentosa, and Stargardt's Disease (fundus flavimaculatus).

The RPE cells provided herein may be human RPE cells. Note, however, that the human cells may be used in human patients, as well as in animal models or animal patients. For example, the human cells may be tested in mouse, rat, cat, dog, or non-human primate models of retinal degeneration. Additionally, the human cells may be used therapeutically to treat animals in need thereof, such as in veterinary medicine.

Modes of Administration

The pharmaceutical preparation may be formulated in a pharmaceutically acceptable carrier according to the route of administration. For example, the preparation may be formulated to be administered to the subretinal space of the eye.

The preparation comprising RPE cells may be administered to one eye or both eyes in the same patient. The administration to both eyes may be sequential or simultaneous. For example, the preparation comprising RPE cells may be formulated as a suspension, solution, slurry, gel, or colloid.

RPE cells of the invention may be administered locally by injection (e.g., intravitreal injection), or as part of a device or implant (e.g., an implant). For example, the preparation may be administered by injection into the subretinal space of the eye. Also, the preparation may be administered transcorneally. For example, the cells of the present invention may be transplanted into the subretinal space by using vitrectomy surgery. Additionally, at the time of injection, RPE cells may be may be resuspended with commercially available balanced salt solution to achieve the desired osmolality and concentration for administration by subretinal injection.

Depending on the method of administration, the RPE cells may be added to buffered and electrolyte balanced aqueous solutions, buffered and electrolyte balanced aqueous solutions with a lubricating polymer, mineral oil or petrolatum-based ointment, other oils, liposomes, cyclodextrins, sustained release polymers or gels.

Matrices for Use with RPE Cells

The methods described herein may comprise a step of administering RPE cells of the invention as an implant or device. In certain embodiments, the device is bioerodible implant for treating a medical condition of the eye comprising an active agent dispersed within a biodegradable polymer matrix, wherein at least about 75% of the particles of the active agent have a diameter of less than about 10 µm. The bioerodible implant is sized for implantation in an ocular region. The ocular region may be any one or more of the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina. The biodegradable polymer may be, for example, a poly(lactic-co-glycolic)acid (PLGA) copolymer, biodegradable poly(DL-lactic-co-glycolic acid) films, or PLLA/PLGA polymer substrates. The ratio of lactic to glycolic acid monomers in the polymer is about 25/75, 40/60, 50/50, 60/40, 75/25 weight percentage, more preferably about 50/50. The PLGA copolymer may be about 20, 30, 40, 50, 60, 70, 80 to about 90 percent by weight of the bioerodible implant. The PLGA copolymer may be from about 30 to about 50 percent by weight, preferably about 40 percent by weight of the bioerodible implant. The RPE cells may be transplanted in conjunction with a biocompatible polymer such as polylactic acid, poly(lactic-co-glycolic acid), 50:50 PDLGA, 85:15 PDLGA, and INION GTR® biodegradable membrane (mixture of biocompatible polymers). See U.S. Pat. Nos. 6,331,313; 7,462,471; and 7,625,582. See also Hutala, et al. (2007) "In vitro biocompatibility of degradable biopolymers in cell line cultures from various ocular tissues: Direct contact studies." *Journal of Biomedical Materials Research* 83A(2): 407-413; Lu, et al. (1998) *J Biomater Sci Polym Ed* 9: 1187-205; and Tomita, et al. (2005) *Stem Cells* 23: 1579-88.

Screening Assays

The invention provides a method for screening to identify agents that modulate RPE cell maturity. For example, RPE cells differentiated from human ES cells may be used to screen for agents that promote RPE maturation. Identified agents may be used, alone or in combination with RPE cells, as part of a treatment regimen. Alternatively, identified agents may be used as part of a culture method to improve the survival of RPE cells differentiated in vitro.

The RPE cells may be used a research tool in settings such as a pharmaceutical, chemical, or biotechnology company, a hospital, or an academic or research institution. Such uses include the use of RPE cells differentiated from embryonic stem cells in screening assays to identify, for example, agents that may be used to promote RPE survival in vitro or in vivo, or that may be used to promote RPE maturation. Identified agents may be studied in vitro or in animal models to evaluate, for example, their potential use alone or in combination with RPE cells.

The invention provides a method for identifying agents that promote RPE maturation comprising providing a RPE cell, contacting said RPE cell with an agent, assessing said RPE cell for signs of maturity, and then identifying an agent that promotes RPE maturation when said agent causes RPE cell to show signs of maturity. The signs of maturity may be pigmentation level, gene expression levels, and morphology as discussed herein.

Commercial Applications and Methods

Certain aspects of the present invention pertain to the production of RPE cells to reach commercial quantities. The RPE cells may be produced on a large scale, stored if necessary, and supplied to hospitals, clinicians or other healthcare facilities.

Accordingly certain aspects of the present invention relate to methods of production, storage, and distribution of RPE cells produced by the methods disclosed herein. Following RPE production, RPE cells may be harvested, purified, and optionally stored prior to a patient's treatment. RPE cells may optionally be patient specific or specifically selected based on HLA or other immunologic profile. For example, once a patient presents with an indication such as, for example, diabetic retinopathy, macular degeneration (including age-related macular degeneration), retinitis pigmentosa, retinal atrophy, retinal detachment, retinal dysplasia, and Stargardt's Disease (fundus flavimaculatus), RPE cells may be ordered and provided in a timely manner. Accordingly, the present invention relates to methods of producing RPE cells to attain cells on a commercial scale, cell preparations comprising RPE cells derived from said methods, as well as methods of providing (i.e., producing, optionally storing, and selling) RPE cells to hospitals and clinicians. The production of differentiated RPE cells or mature differentiated RPE cells may be scaled up for commercial use.

The present invention also provides for methods of conducting a pharmaceutical business comprising establishing a distribution system for distributing the preparation for sale or may include establishing a sales group for marketing the pharmaceutical preparation.

The present invention provides methods of supplying RPE cells to hospitals, healthcare centers, and clinicians, whereby RPE cells produced by the methods disclosed herein are stored, ordered on demand by a hospital, healthcare center, or clinician, and administered to a patient in need of RPE cell therapy. A hospital, healthcare center, or clinician orders RPE cells based on patient specific data, RPE cells are produced according to the patient's specifications and subsequently supplied to the hospital or clinician placing the order. For example, after a particular RPE cell preparation is chosen to be suitable for a patient, it is thereafter expanded to reach appropriate quantities for patient treatment.

Further aspects of the invention relate to a library of RPE cells that can provide matched cells to potential patient recipients. Accordingly, the invention provides a method of conducting a pharmaceutical business, comprising the step of providing RPE cell preparations that are homozygous for at least one histocompatibility antigen, wherein cells are chosen from a bank of such cells comprising a library of RPE cells that may be expanded by the methods disclosed herein, wherein each RPE cell preparation is hemizygous or homozygous for at least one MHC allele present in the human population, and wherein said bank of RPE cells comprises cells that are each hemizygous or homozygous for a different set of MHC alleles relative to the other members in the bank of cells. As mentioned above, gene targeting or loss of heterozygosity may be used to generate the hemizygous or homozygous MHC allele stem cells used to derive the RPE cells.

The present invention also includes methods of obtaining human ES cells from a patient and then generating and expanding RPE cells derived from the ES cells. These RPE cells may be stored. In addition, these RPE cells may be used to treat the patient from which the ES were obtained or a relative of that patient.

The present disclosure demonstrates that human RPE cells may be reliably differentiated and expanded from human ES cells under well-defined and reproducible conditions—representing an inexhaustible source of cells for patients with retinal degenerative disorders. The concentration of these cells would not be limited by availability, but rather could be titrated to the precise clinical requirements of the individual. Repeated infusion or transplantation of the same cell population over the lifetime of the patient would also be possible if deemed necessary by the physician. Furthermore, the ability to create banks of matching or reduced-complexity HLA hES lines from which RPE cells could be produced could potentially reduce or eliminate the need for immunosuppressive drugs and/or immunomodulatory protocols altogether.

Unless defined otherwise, all technical and scientific terms used herein have the same meaning as those commonly understood by one of ordinary skill in the art to which this invention belongs. Although methods and materials similar or equivalent to those described herein can be used in the invention or testing of the present invention, suitable methods and materials are described below. The materials, methods and examples are illustrative only, and are not intended to be limiting.

In order to further define the invention, the following terms and definitions are provided herein.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Throughout this specification, the word "comprise" or variations such as "comprises" or "comprising" will be understood to imply the inclusion of a stated integer or groups of integers but not the exclusion of any other integer or group of integers.

"Effective amount," as used herein, refers broadly to the amount of a compound or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and preexisting conditions, of the patient to be treated. The term "effective amount" is synonymous with "therapeutically effective amount" for purposes of this invention.

"Embryo" or "embryonic," as used herein refers broadly to a developing cell mass that has not implanted into the uterine membrane of a maternal host. An "embryonic cell" is a cell isolated from or contained in an embryo. This also includes blastomeres, obtained as early as the two-cell stage, and aggregated blastomeres.

"Embryonic stem cells" (ES cells), as used herein, refers broadly to cells derived from the inner cell mass of blastocysts or morulae that have been serially passaged as cell lines. The ES cells may be derived from fertilization of an egg cell with sperm or DNA, nuclear transfer, parthenogenesis, or by means to generate ES cells with homozygosity in the HLA region. ES cells may also refer to cells derived from a zygote, blastomeres, or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce a cell. Embryonic stem cells, regardless of their source or the particular method used to produce them, can be identified based on the: (i) ability to differentiate into cells of all three germ layers, (ii) expression of at least Oct-4 and alkaline phosphatase, and (iii) ability to produce teratomas when transplanted into immunocompromised animals. The term also includes cells isolated from one or more blastomeres of an embryo, preferably without destroying the remainder of the embryo. The term also includes cells produced by somatic cell nuclear transfer, even when non-embryonic cells are used in the process. ES cells may be derived from fertilization of an egg cell with sperm or DNA, nuclear transfer, parthenogenesis, or by means to generate ES cells with homozygosity in the HLA region. ES cells are also cells derived from a zygote, blastomeres, or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce a cell. Human embryonic stem cells of the present invention may include, but are not limited to, MA01, MA09, ACT-4, No. 3, H1, H7, H9, H14 and ACT30 embryonic stem cells. In certain embodiments, human ES cells used to produce RPE cells are derived and maintained in accordance with GMP standards.

"Embryo-derived cells" (EDC), as used herein, refers broadly to morula-derived cells, blastocyst-derived cells including those of the inner cell mass, embryonic shield, or epiblast, or other pluripotent stem cells of the early embryo, including primitive endoderm, ectoderm, and mesoderm and their derivatives. "EDC" also including blastomeres and cell masses from aggregated single blastomeres or embryos from varying stages of development, but excludes human embryonic stem cells that have been passaged as cell lines.

"Macular degeneration," as used herein, refers broadly to diseases characterized by a progressive loss of central vision associated with abnormalities of Bruch's membrane, the neural retina, and the retinal pigment epithelium. Macular degeneration diseases include but are not limited to age-related macular degeneration, North Carolina macular dystrophy, Sorsby's fundus dystrophy, Stargardt's disease, pattern dystrophy, Best disease, malattia leventinese, Doyne's honeycomb choroiditis, dominant drusen, and radial drusen.

"Pluripotent stem cell," as used herein, refers broadly to a cell capable of prolonged or virtually indefinite proliferation in vitro while retaining their undifferentiated state, exhibiting a stable (preferably normal) karyotype, and having the capacity to differentiate into all three germ layers (i.e., ectoderm, mesoderm and endoderm) under the appropriate conditions.

"Pluripotent embryonic stem cells," as used herein, refers broadly cells that: (a) are capable of inducing teratomas when transplanted in immunodeficient (SCID) mice; (b) are capable of differentiating to cell types of all three germ layers (e.g., ectodermal, mesodermal, and endodermal cell types); and (c) express at least one molecular embryonic stem cell markers (e.g., express Oct-4, alkaline phosphatase, SSEA 3 surface antigen, SSEA 4 surface antigen, NANOG, TRA 1 60, TRA 1 81, SOX2, REX1). Exemplary pluripotent stem cells can be generated using, for example, methods known in the art. Exemplary pluripotent stem cells include embryonic stem cells derived from the ICM of blastocyst stage embryos, as well as embryonic stem cells derived from one or more blastomeres of a cleavage stage or morula stage embryo (optionally without destroying the remainder of the embryo). Such embryonic stem cells can be generated from embryonic material produced by fertilization or by asexual means, including somatic cell nuclear transfer (SCNT), parthenogenesis, and androgenesis. Further exemplary pluripotent stem cells include induced pluripotent stem cells (iPS cells) generated by reprogramming a somatic cell by expressing or inducing expression of a combination of factors (herein referred to as reprogramming factors). iPS cells can be generated using fetal, postnatal, newborn, juvenile, or adult somatic cells. In certain embodiments, factors that can be used to reprogram somatic cells to pluripotent stem cells include, for example, a combination of Oct4 (sometimes referred to as Oct 3/4), Sox2, c-Myc, and Klf4. In other embodiments, factors that can be used to reprogram somatic cells to pluripotent stem cells include, for example, a combination of Oct-4, Sox2, Nanog, and Lin28. In other embodiments, somatic cells are reprogrammed by expressing at least 2 reprogramming factors, at least three reprogramming factors, or four reprogramming factors. In other embodiments, additional reprogramming factors are identified and used alone or in combination with one or more known reprogramming factors to reprogram a somatic cell to a pluripotent stem cell. iPS cells typically can be identified by expression of the same markers as embryonic stem cells, though a particular iPS cell line may vary in its expression profile.

"RPE cell," "differentiated RPE cell," "ES-derived RPE cell," and as used herein, may be used interchangeably throughout to refer broadly to an RPE cell differentiated from a pluripotent stem cell using a method of the invention. The term is used generically to refer to differentiated RPE cells, regardless of the level of maturity of the cells, and thus may encompass RPE cells of various levels of maturity. RPE cells can be visually recognized by their cobblestone morphology and the initial appearance of pigment. RPE cells can also be identified molecularly based on substantial lack of expression of embryonic stem cell markers such as Oct-4 and NANOG, as well as based on the expression of RPE markers such as RPE-65, PEDF, CRALBP, and bestrophin. Thus, unless otherwise specified, RPE cells, as used herein, refers to RPE cells differentiated in vitro from pluripotent stem cells.

"Mature RPE cell" and "mature differentiated RPE cell," as used herein, may be used interchangeably throughout to refer broadly to changes that occur following initial differentiating of RPE cells. Specifically, although RPE cells can be recognized, in part, based on initial appearance of pigment, after differentiation mature RPE cells can be recognized based on enhanced pigmentation.

"Pigmented," as used herein refers broadly to any level of pigmentation, for example, the pigmentation that initial occurs when RPE cells differentiate from ES cells. Pigmentation may vary with cell density and the maturity of the differentiated RPE cells. The pigmentation of a RPE cell may be the same as an average RPE cell after terminal differentiation of the RPE cell. The pigmentation of a RPE cell may be more pigmented than the average RPE cell after terminal differentiation of the RPE cell. The pigmentation of a RPE cell may be less pigmented than the average RPE cell after terminal differentiation.

"Signs" of disease, as used herein, refers broadly to any abnormality indicative of disease, discoverable on examination of the patient; an objective indication of disease, in contrast to a symptom, which is a subjective indication of disease.

"Symptoms" of disease as used herein, refers broadly to any morbid phenomenon or departure from the normal in structure, function, or sensation, experienced by the patient and indicative of disease.

"Therapy," "therapeutic," "treating," or "treatment", as used herein, refers broadly to treating a disease, arresting or reducing the development of the disease or its clinical symptoms, and/or relieving the disease, causing regression of the disease or its clinical symptoms. Therapy encompasses prophylaxis, prevention, treatment, cure, remedy, reduction, alleviation, and/or providing relief from a disease, signs, and/or symptoms of a disease. Therapy encompasses an alleviation of signs and/or symptoms in patients with ongoing disease signs and/or symptoms (e.g., blindness, retinal deterioration.) Therapy also encompasses "prophylaxis" and "prevention". Prophylaxis includes preventing disease occurring subsequent to treatment of a disease in a patient or reducing the incidence or severity of the disease in a patient. The term "reduced", for purpose of therapy, refers broadly to the clinical significant reduction in signs and/or symptoms. Therapy includes treating relapses or recurrent signs and/or symptoms (e.g., retinal degeneration, loss of vision.) Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., blindness, retinal degeneration).

The present invention will now be more fully described with reference to the following examples, which are illustrative only and should not be considered as limiting the invention described above.

EXAMPLES

The invention now being generally described, it will be more readily understood by reference to the following examples, which are included merely for purposes of illustration of certain aspects and embodiments of the present invention, and are not intended to limit the invention.

Example 1

In pre-clinical animal studies, we have looked for the presence of teratoma/tumors that might developed from hES cells, if they were present in human retinal pigment epithelium (hRPE) cell products. When animals were injected with 100% hES cells, teratomas were detected (microscopically) within four weeks. However, no tumors were detected when hRPE cells were spiked with 1% or fewer hES cells. The maximum permitted fraction of hES cells in the product is at least an order of magnitude less than the concentration of hES, that will lead to teratomas in mice, i.e., less than 0.1%. Ideally, it would be desirable to accurately measure the concentration of hES cells even at much lower values than this, or preferably to be able to indicate that there are no hES cells in the hRPE cell product. As discussed above, conventional methods (such as RT-PCR, Western Blotting, and flow cytometry) are insufficiently sensitive for determination of whether there are a few residual hES cells in a population of about 500,000 differentiated cells.

Example 2

This example describes an assay having exquisite sensitivity for detection of pluripotent hES cells in a cell population. Using this assay, cells differentiated from hES cells were tested to determine whether any residual hES cells remained in the population. This assay can provide valuable safety information because any residual hES cells have the potential to form tumors upon implantation into a recipient.

In this example, it is demonstrated that two different aspects of the assay (each of which could be used independently from one another) contributed to the sensitivity of the assay: first, plating under conditions that supported the maintenance of hES cells to minimize cell differentiation that could result in loss of hES cell marker expression; and second, development of a technique that permitted evaluation of every cell in a population, with a trained operator able to observe between about one and ten million cells per hour.

It is currently accepted in scientific literature that pluripotent hES cells (which can form teratomas in vivo) express a known set of molecular markers, and Oct-4 expression is critical for retention of pluripotency while loss of this marker is associated with cellular differentiation. Any cell expressing this marker at a detectable level may be seen as pluripotent and thus undesired in the final product. A cell that has lost Oct-4 expression can be seen as no longer pluripotent. In this assay, cells were first examined for positive alkaline phosphatase staining under visible light, then examined for Oct-4 expression by immunofluorescence.

Human retinal pigment epithelium (hRPE) cells were obtained by differentiating human embryonic stem (hES) cells as described in U.S. Pat. No. 7,736,896, U.S. Ser. No. 12/682,712, and U.S. Ser. No. 61/262,002. The hRPE cells differentiated from the MA09 hES cell line which was originated from a single human blastomere as described in U.S. Pat. No. 7,893,315. These cells were designated as MA09-hRPE.

The sensitivity of the assay to detect hES cells in cultures of RPE cells was determined. In these experiments, mixtures of MA09-hRPE and hES cells were prepared, containing 0.001%, 0.01%, 0.1%, 1% or 10% hES (a total of ~200,000 cells) and seeded in triplicate. Cells were seeded into two different types of culture conditions: either RPE culture conditions (specifically, plating on gelatin coated 4-well plates in EGM®-2 (Lonza Biologics, Basel, Switzerland) medium according to the normal procedure for culturing hRPE cells), or hES cell culture conditions (conditions that support the growth and maintenance of hES cells which in this experiment were plating on MEF and using conditioned hES-GM; see Table 2). The hES cells used were a GFP-positive hES cell line (H1 or WA01). By using this GFP-positive hES cell line, it was possible to detect the presence of cells which have derived from the hES cells whether the cells remained pluripotent or differentiated. After these initial experiments using H1, it was confirmed that similar results were obtained with another hES cell line, MA09, which did not express GFP but could be detected using anti-human nuclei antibody which stained human cells (including the hES cells) but did not stain the MEF (which are of mouse origin).

After plating, the cells were cultured to permit attachment to the substrate, then the cells were fixed with 2% paraformaldehyde, permeabilized with 0.1% NP-40 substitute (which may be done immediately or up to several weeks after fixation, e.g., after about 24 hours), and stained for alkaline phosphatase (AP) and Oct-4. AP was detected using VECTOR® Blue (Vector Laboratories) according to the manufacturer's instructions, which produces a stain that is detectable under visible light. Oct-4 was detected using immunofluorescence (using essentially the same methods as described in Example 7, below). Using a low power objective of a fluorescent microscope the entire well was first scanned in transmitted visible light as a top—to right—to the edge-down-left to the edge-down-right . . . repetitive pattern looking at each cell on the plate for the blue staining of cell indicative of alkaline phosphatase activity. Because the cells were being observed under visible light, non-stained cells were also visible, and the microscope focus was adjusted as needed to correct for any vertical deviations during scanning, thereby ensuring that the cells remained in the focal plane. Once a blue-stained cell was found, it was re-examined at higher power (×20 objective) under ultraviolet light for Oct-4 staining and then for GFP. Because the duration of observation under ultraviolet light was kept low by this method, Oct-4 and GFP stains were not photobleached. Representative photomicrographs are presented in FIG. 1. The top panels show GFP-positive (left) and Oct-4 positive (right) cells mixed with RPE cells at a 1:10 ratio (10%). DAPI staining (bottom left panel) shows all cells present in the field (both RPE and hES) and bottom right panel shows alkaline phosphatase staining. Magnification ×200.

Because AP staining is detectable under visible light, as primary screening because it allowed us to rapidly examine every cell in the population (200,000 cells in this example). Cells that were AP-positive were examined under ultraviolet light for Oct-4 staining and GFP expression. Cells positive for AP, Oct-4, and GFP are pluripotent, while cells that are GFP positive and Oct-4 negative are differentiated progeny of pluripotent cells. Some AP positive cells were GFP negative and Oct-4 negative, indicating that AP can be used to rapidly identify potential hES cells, and those cells can then be examined for a second hES cell marker (Oct-4 in this example) to identify hES cells. Because the added hES cells were constitutively GFP-positive, detected cells that were AP positive but negative for Oct-4 and negative for GFP were interpreted not to have originated from the added hES cells but rather to result from occasional AP-positive cells within the MEF population.

When the cells were plated under RPE culture conditions, we found that more than 50% of GFP-positive cells were Oct-4-negative, confirming that RPE culture conditions poorly support the pluripotent state of hES cells even after a short culture duration. However, every Oct-4 positive cell also expressed alkaline phosphatase and GFP, so this allowed us to conclude that Oct-4 expression was sufficient to identify hES cells.

However, when cells were plated under hES cell culture conditions, Oct-4 expression was retained in a much greater fraction of the GFP-positive cells, permitting detection of Oct-4 positive hES cells in cultures spiked with as low as 0.001%, hES cells. This is in agreement with our observations that the culture condition for RPE cell growth is not conducive for maintenance of hES cell cultures, but instead causes the hES cells to differentiate (see Example 3 below).

Alkaline phosphatase was more sensitive that Oct-4 allowing the detection as few 5 cells in approximately 178,000. Thus, alkaline phosphatase assay was chosen as the primary screening method. However, because AP is not a unique marker of hES cells, its expression identifies potential hES cells that can be confirmed with a more definitive marker, like Oct-4. False AP positives were seen (GFP or Oct-4 negative), and Oct-4 is used as a confirmatory assay. With 0.001% hES cells a total of 5 cells in the three wells stained positive for alkaline phosphatase and were GFP positive. Thus, using these methods the limit of detection for the immunofluorescent detection of hES cells in RPE cell cultures was concluded to be 5/600,000 cell (0.0008%).

Example 3

This example describes the results of an in vitro spiking study. Its purpose was to show that all added hESC, even at high percentage, are differentiating under RPE culture conditions over a course of 6 weeks or 2 passages—which is less than the time separating RPE at harvest for cryopreservation from hESC or differentiated EB.

The in vitro spiking study was performed with MA09 and with H1-GFP cells. Cultures contained mixtures of hESC and RPE, with 1%, 10%, or 20% hES cells. The cell populations were evaluated by staining and Q-PCR at 3 weeks (p1) and 6 weeks (p2). Microscopic observation of cultures showed that hESC began to differentiate almost immediately, forming β-D structures which disrupted RPE monolayer integrity and thus were easily seen. By the end of the time in culture, no Oct-4 positive cells were found, but some alkaline phosphatase staining persisted. AP staining was though to result from differentiated hESC, as differentiation can produce various cell types, some of which could be alkaline phosphatase-positive.

TABLE 3

Cell mixtures used in the in vitro spiking study.

| hES | MA09-hRPE |
|---|---|
| 0%* | 100%* |
| 1% | 99% |
| 10% | 90% |
| 20% | 80% |
| 100%** | 0% |

*negative control
**positive control

Freshly prepared suspensions of hRPE and hES cells, mixed in the above ratios, were plated onto gelatin coated 6-well and 4-well plates in EGM-2® medium according to the normal procedure for culturing hRPE cells. The EGM-2® medium is conducive for the proliferation of hRPE cells. The 4-well control plates were fixed with 2% paraformaldehyde or harvested (for qPCR analysis) on Day 3, to assess the initial appearance of these cultures. The remaining 6-well plates were cultured until con fluency at which time the medium was changed to EX-CELL® MDBK-MM that is utilized for the maintenance of hRPE cells. After approximately 3 weeks, the cultures were either fixed or harvested (for qPCR) or passaged into 6-well plates or 4-well plates. The plates were cultured for an additional 3 weeks before they were either fixed or harvested for qPCR. This culturing simulated the manufacturing process from the isolation of the differentiated RPE colonies to the final product.

In study 1, the hES cells added to the cultures were MA09 cells. The fixed plates were stained for hES cell marker, Oct-4 using indirect immunofluorescence followed with Alexa-conjugated secondary antibodies (identification as a red emitted light) and DAPI for visualization of the nuclei and examined under an inverted fluorescent microscope. Alkaline phosphatase activity was determined on the same plates using VECTOR® Blue kit (Vector Laboratories, Burlingame, Calif.). Additionally, live cultures were examined under the phase contrast microscope or using Hoffman Modulation Optics (HMC) for irregularities in the monolayer.

In study 2, the hES cells added to the cultures were H1-GFPp cells which constitutively express GFP. These hES cells and their progeny are readily detectable due to their GFP expression, permitting detection of the ES cells or their during the entire culturing period regardless of whether they remained pluripotent or differentiated. qPCR was performed using the TAQMAN® Gene Expression Assay (APPLIED BIOSYSTEMS®) assaying for expression of Oct-4, Nanog, Rex-1 and Sox2. Beta-actin gene expression was used for normalization.

Study 3 was identical to study 2, except that the MA09-RPE cells underwent an additional passage in culture before being mixed with the hES H1-GFPp cells.

Study 1 Results.

Since there is no direct means of positively identifying the MA09 embryonic stem cells in culture, the primary goal of this experiment involving adding MA09 hES cells into cultures of hRPE cells was to determine if cells staining for Oct-4 or alkaline phosphatase activity (which are specific for ES cells) could be detected in these mixed cultures. The results indicated that while cells staining positive for both Oct-4 and Alkaline Phosphatase were detected (double staining) at 3 days, there was no definitive positive staining for the embryonic stem cell markers at 3 weeks. Such double-positive staining cells at 3 days were mostly found in typical ES-like colonies and had ES-like morphology. Microscopic examination of all cultures showed that at 100% (positive control) hES cells behaved in a typical embryonic stem cell manner, i.e. they differentiated, forming three-dimensional structures with some free-floating embryoid body-like aggregates. Whereas pure RPE cultures (negative control) demonstrated typical for RPE growth behavior, i.e. they became elongated and less pigmented during the proliferative phase and regained epithelial polygonal pigmented appearance after the monolayer was established and the medium was changed to MDBK-MM. However, in all mixed cultures (1%, 10%, 20% hES cells) the presence of two different cell types was easily noticeable ranging from a few irregularities in the monolayer resembling differentiated derivatives of hES cells to large budding embryoid body-like and other β-D structures typical for differentiating hES cells. A few clusters of alkaline phosphatase positive cells were seen in 10% and 20% cultures, but the morphology of these stained cells was very different from ES cells—these were either fibroblast-looking cells or small cell groups inside three-dimensional differentiating aggregates of ES cells. In such three dimensional aggregates the level of non-specific antibody binding, or "noise" was higher than in cell monolayers, but we could not correlate any of the brightly stained patches with DAPI-stained nuclei which would be indicative of positive staining for Oct-4.

Study 2 and 3 Results.

The findings for both of these studies are discussed together, since the findings using both cultures of hRPE cells were identical. On day 2, GFP-positive cells were detected that had the morphology of hES cell colonies and well-detectable presence of Oct-4 by immunostaining, thus confirming the presence of ES in the RPE cultures. The hES cells grew and differentiated forming very prominent three-dimensional aggregates in RPE cultures and easily detectable (both by morphology of the derivatives and by glowing GFP-positive cellular masses). Morphological observation confirming the presence of differentiated hES cell, was seen even in 1% hES:RPE ratio. However, by the end of three weeks, no Oct-4 was detectable in the nuclei except for occasional single cells in 100% of hES cell cultures (which is consistent with our prior observations of presence of rare Oct-4 positive cells in 3 week old differentiating hES cell cultures). The specific nature of these differentiated cells was not determined, but they appeared to be quite differentiated by this time.

Tables 4 through 8 summarize the morphological observations and staining results for these cultures. In these tables, – means undetectable, ? means signal detectable but not convincingly specific, + means signal detectable, ++ means signal very strong, and +++ means signal strong and specific.

TABLE 4

Colonies with hES cell morphology

| % hESC added to RPE | Day 3 | Day 22 | Second passage, three weeks - end of study |
|---|---|---|---|
| 0 (pure RPE) | — | — | — |
| 1% | + | — | — |
| 10% | +/++ | — | — |
| 20% | ++ | — | — |
| 100% (no RPE) | +++ | — | — |

TABLE 5

Cells with other than RPE or undifferentiated hESC morphology

| % hESC added to RPE | Day 3 | Day 22 | Second passage, three weeks - end of study |
|---|---|---|---|
| 0 (pure RPE) | — | — | — |
| 1% | +/? | ++ | + |
| 10% | +/++ | ++ | ++ |
| 20% | +/? | +++ | +++ |
| 100% (no RPE) | ++ | +++ | +++ |

TABLE 6

Oct-4 staining

| % hESC added to RPE | Day 3 | Day 22 | Second passage, three weeks - end of study |
|---|---|---|---|
| 0 (pure RPE) | — | — | — |
| 1% | + | – | — |
| 10% | +/++ | – | — |
| 20% | ++ | – | — |
| 100% (no RPE) | +++ | –/? | — |

TABLE 7

Alkaline phosphatase activity

| % hESC added to RPE | Study 1, passage 1, 1 day | Study 1, passage 1, three weeks | Study 2, passage 1, three weeks | Study 2, passage 2, three weeks - end of study |
|---|---|---|---|---|
| 0 (pure RPE) | –/– | –/– | –/– | –/– |
| 1% | +/+ | +/+ | +/+ | +/– |
| 10% | –/+ | –/+ | –/+ | –/– |
| 20% | –/+ | –/+ | –/+ | –/+ |
| 100% (no RPE) | –/+ | –/+ | –/+ | –/+ |

TABLE 8

GFP-positive cells (hES cells or their derivatives) in cultures spiked with H1 cells.

| % hESC added to RPE | Day 3 | Day 22 | Second passage, three weeks - end of study |
|---|---|---|---|
| 0 (pure RPE) | — | — | — |
| 1% | +++ | +++ | +++ |
| 10% | +++ | +++ | +++ |
| 20% | +++ | +++ | +++ |
| 100% (no RPE) | +++ | +++ | +++ |

Conclusions hESC and their derivatives are detectable by microscopic observation in both early and late cultures of RPE cells even when added at 1% concentration. Colonies of hES cells (more or less differentiated) are visible at day 3 when RPE cells are still flat and under-confluent. After three weeks in culture, microscopic observation reveals large cell masses derived from hESC that are very different from RPE morphology and easily noticeable.

At day 3 some of hESC cells present in the culture still remain pluripotent, but at day 22 the outcome was dependent on the fraction of hES cells in the initial culture. In cultures initially containing 20% hES cells or fewer, all of the cells were differentiated at day 22. However, in cultures initially containing 100% hES cells, a few Oct-4 positive cells remained detectable at 22 days.

Oct-4 staining is detectable at day 3. In 1% hESC cultures, Oct-4 positive cells were more difficult to detect but in 10% and 20% these cells were readily detected.

When H1-GFPp cells were used, the GFP marker was present at all stages of the experiment and easily detectable in 10% and 20% hESC at day 3. At day 22 it was very easy to detect in all different concentrations, as derivatives of hESC grew.

Example 4

This example describes further observations upon continuing to culture the mixed populations of hES cells and RPE cells that was described in Example 3.

After three weeks in culture at passage 2 the cells were either harvested in RLT buffer for Q-PCR or fixed with 2%

PFA and stained for Oct-4. Alkaline phosphatase activity was detected using VECTOR® Blue stain in accord with the manufacturer's instructions. The samples were mounted in VECTASHIELD® with DAPI and examined/photographed.

Several areas of blue staining (indicating the presence of alkaline phosphatase reaction product) were observed in several samples. However, none of these cells were Oct-4 positive, nor were there any other Oct-4 positive cells detected in any field examined. These results indicate that ES cells remained in the culture. The observed alkaline phosphatase staining could be a result of ES cell differentiation to produce other cell types that have alkaline phosphatase activity.

GFP-positive cells were present in all examined samples and their morphology was indicative of various ES cell derivatives but did not resemble ES cells.

Positive controls (MA09 hES cells cultured for three days) showed very high level of Oct-4 staining and alkaline phosphatase activity.

Conclusions hES cells mixed with RPE cells and cultured in RPE media differentiate but continue to grow in differentiated state. Several additional tests might be performed to detect any possible ES cell contamination.

For early cultures of RPE cells (2 to 3 days) stained for Oct-4/alkaline phosphatase, at this stage the cells are under-confluent and grow as a monolayer and have not deposited too much of extracellular matrix which creates background, so presence of any single cell or small cluster should be easy to detect. For immunofluorescence studies, a sample size of at least 200,000 cells, preferably in triplicates would give greater sensitivity.

As the RPE cultures grow and mature, presence of hES cells would create irregularities in the monolayer ranging from single cell of non-epithelial morphology to large three-dimensional aggregates which may harbor undifferentiated ES cells. While single cells of non-RPE morphology may be transdifferentiated or senescent RPE, or retinal progenitors, large aggregates β-D cell aggregates of a typical for differentiating ES cells morphology may suggest presence of hES cells in the culture.

Example 5

It is widely accepted that hES cells, when grown under the conditions that do not support their pluripotent state (such as on feeder cells, defined matrix, or defined media) differentiate very quickly. This differentiation is associated with the loss of molecular markers of pluripotency, such as Oct-4 and alkaline phosphatase. RPE culture conditions do not support undifferentiated growth of hES cells, therefore it was postulated (and confirmed by these experiments) that at the time when the mixture of initially pluripotent hES cells with RPE cells is fixed, many of hES cells would already have lost or down regulated Oct-4 expression and thus become undetectable.

To quantify the effect of culture conditions on sensitivity of detection of hES cells, low concentrations of H1-GFPp cells were mixed with MA09-hRPE cells and plated either under conditions that favor maintenance of their pluripotent state or conditions that do not. Specifically, the cells were either cultured in hES cell culture media on mouse embryonic fibroblast feeder cells (MEFs), or in endothelial growth media supplemented with 2% FES (EGM-2®) on gelatin. EGM-2® is a medium that is conducive to RPE proliferation but does not maintain the pluripotent state of hES cells. To decrease the time for differentiation to occur in culture, the cells were cultured for only 16 hours before being fixed. The cells were then stained for alkaline phosphatase and Oct-4 and microscopically examined as described in Example 2. For the cell populations plated in ES cell media on feeder cells, about 80% of the GFP-positive ceils were positive for AP and Oct-4. In contrast, for the cell populations plated in EGM-2® media, only about 20% of the GFP-positive cells were positive for AP and Oct-4. From these results, we conclude that plating under conditions that favor the maintenance of the pluripotent state can greatly improve sensitivity of detecting hES cells in a cell population.

Example 6

This example shows the relative insensitivity of real-time PCR for detecting rare cell subpopulations.

Methods

The qRT-PCR LOD was assessed using mixtures of MA09-RPE cells and MA09 hES cells. Cryopreserved MA09-RPE cells were thawed and counted, and hES MA09 were also thawed and counted (using alkaline phosphatase staining to determine the number of pluripotent hES cells present). Mixtures were then formed of 400,000 cells with 100%, 10%, 1%, 0.1%, 0.01%, or 0% of the cells being hES cells and the remainder being MA09-RPE. The RNEASY® RNA isolation kit from QIAGEN® was used to extract RNA from the cell mixtures resulting in a final volume of 30 µL RNA per sample. cDNA was then synthesized from 10 µl of RNA with the QUANTITECT® cDNA synthesis kit from QIAGEN® resulting in a final volume of 20 µL cDNA. One µL of cDNA was then tested for relative gene expression in triplicate replicates normalized to the beta actin signal present in each sample. Gene expression analysis was performed using the APPLIED BIOSYSTEMS STEPONE-PLUS® with software version 2.1 and TAQMAN® gene expression assays from LIFE TECHNOLOGIES® following the manufacturer's recommended cycle conditions for comparative Ct relative quantification.

qRT-PCR assays for Nanog, Oct-4 and SOX2 were normalized to the level of expression observed in the 100% hES cell sample (RQ=Relative Quantitation) which serves as the zero set point in the graph below. The mean down-regulation of Nanog (2.51 logs) Oct-4 (2.73 logs) and SOX2 (1.63 logs) for the unspiked (0% hES) RPE sample as compared to the 100% hES control are in line with historic data for this lot. Down-regulation of all hES markers was dramatically reduced in RPE cells spiked with 1% and 10% hES cells.

Results

Figure 2A:
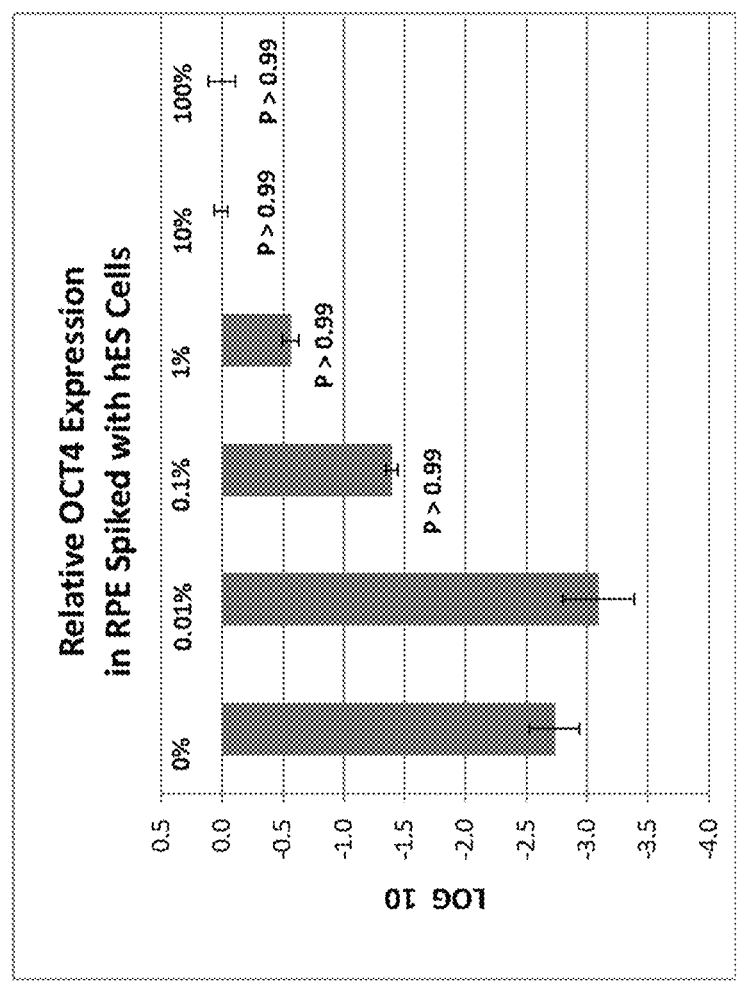
FIG. 2A-C. RNA was extracted from mixed populations of RPE cells and hES cells (containing 0%, 0.01%, 0.1%, 1%, 10%, or 100% hES cells as indicated). cDNA was then synthesized and relative gene expression was assayed in triplicate replicates normalized to the beta actin signal present in each sample. Gene expression profiling was performed by RT-qPCR using APPLIED BIOSYSTEMS STEPONEPLUS™ with software version 2.1 and TAQMAN® gene expression assays from LIFE TECHNOLOGIES® following the manufacturer's recommended cycle conditions for comparative relative quantification. Data are expressed as the mean+/−standard deviation for three replicated with P-values determined by T-Testing. Results are presented for (A) OCT4, (B) anog, and (C) SOX 2 expression.
Figure 2B:
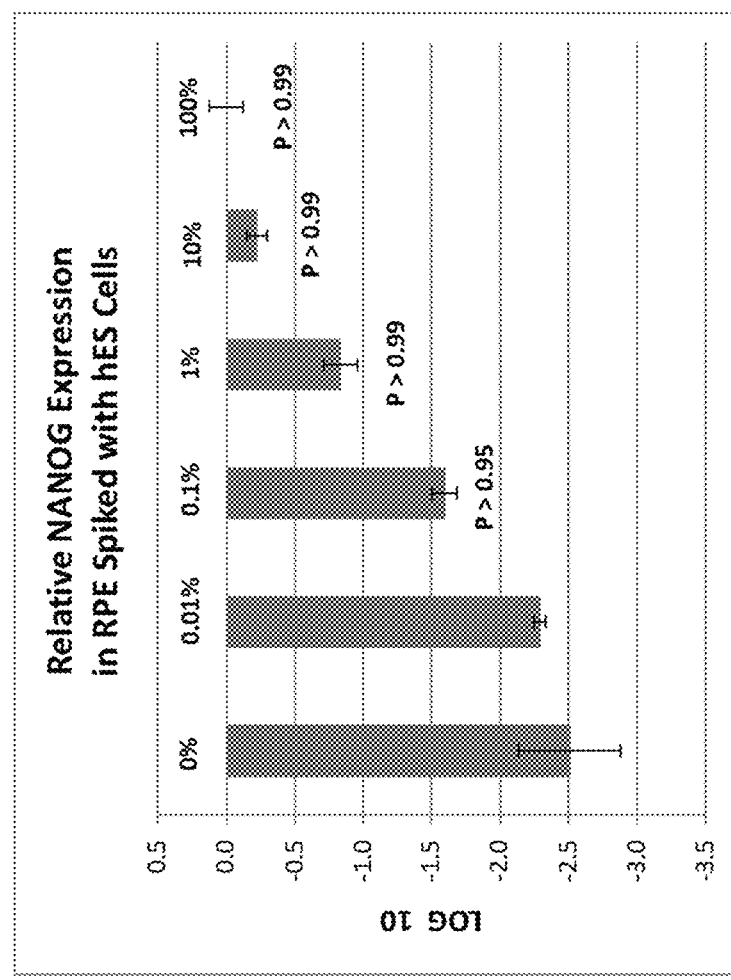
Figure 2C:
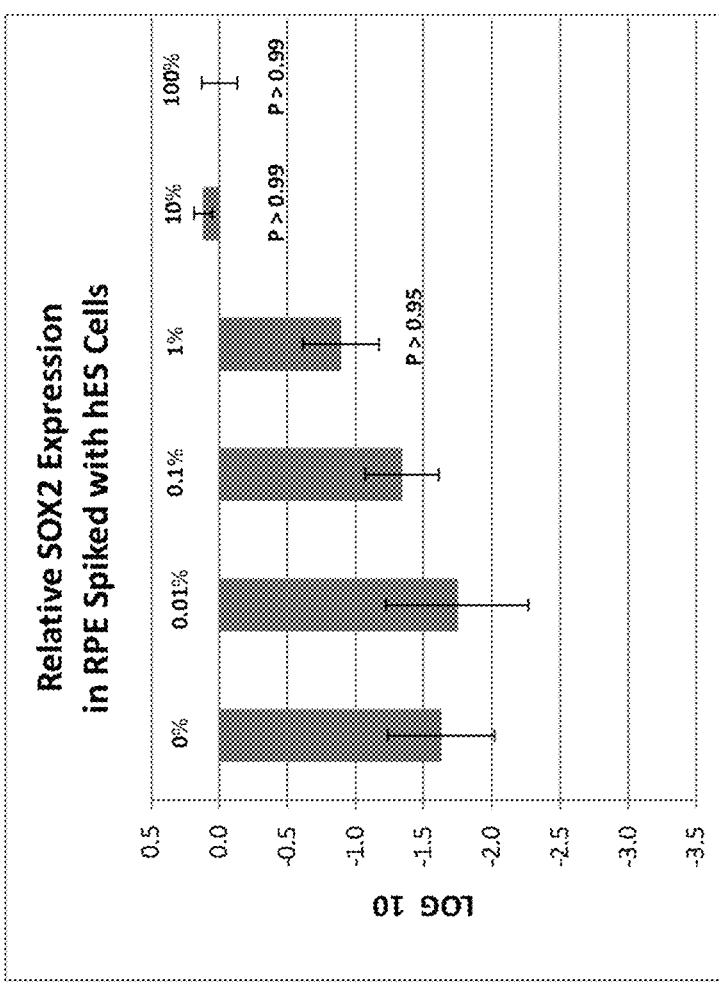

FIG. 2A-C graphically illustrates the relative gene expression (detected by qRT-PCR) for (A) Oct-4; (B) Nanog; and (C) SOX2. Statistically significant differences between the RPE control (0% hES) versus the 0.1% spiked sample are evident for Nanog and Oct-4. However, at the 0.1% spiked dose the extent of SOX2 down-regulation is comparable to that seen in 100% RPE sample. Expression for all three hES cell markers in the 0.001% spiked sample is indistinguishable from that observed the 100% RPE control. Therefore, the qRT-PCR assay would not detect a potential hES cell contamination at the 0.01% level.

In this study, the qRT-PCR LOD for two (Nanog and Oct-4) out of three hES markers was at the 0.1% hES cell level. However, depending on the extent of down-regulation for a particular lot of RPE, it is questionable whether the qRT-PCR would give a consistent and reliable indication of hES cell contamination even at this level. In conclusion, the qRT-PCR assay for hES expression is 3 to 4 orders of magnitude less sensitive than the immunostaining assays described above.

Example 7

This example further demonstrates the exquisite sensitivity of detection of rare hES cells within a population of RPE cells using staining methods. These experiments measure the sensitivity of an assay for detecting undifferentiated (pluripotent) hESC in a population of RPE. RPE were spiked with defined, relatively low numbers of hESC (both H1 and MA09 in different experiments) onto MEF in hESC medium for minimal time that allows the cells to attach and spread, so they remain adherent during immunostaining procedure. These conditions (MEF, conditioned hESC-GM medium, minimal exposure to RPE) preserved pluripotency of hESC. After 14-16 h the plates were fixed and stained, then examined. Nuclei per field (DAPI stain) were counted in several random fields for total cell number per well examined. Because AP staining is expressed in other cell types in addition to pluripotent cells, AP+/Oct4− cells were likely originated from MEF; thus, each AP-positive cell was examined for Oct-4, and double-positive cells were counted as hES cells. As determined by comparison of Oct-4 and GFP, there was a small loss of pluripotent cells to differentiation, but under these optimized for hESC conditions this loss is minimal (the loss was much higher without MEF and in RPE medium).

Methods

MA09 hES and RPE cells were prepared at a ratio 8 hES cells to 10 million RPE cells. Negative controls consisted of RPE cells without added hES cells. Two million RPE cells containing a calculated average of 1.6 hES cells were suspended in hES conditioned cell growth medium and seeded into 6-well plates containing 500,000 of feeder cells (MEF that were previously treated with mitomycin C) to promote the retention of hES pluripotency. Cells were cultured for approximately 16 hours prior to fixing and staining. After 14-18 hours, medium was removed, cultures rinsed with PBS, permeabilized with 0.1% NP-40 (10 minutes) and rinsed again. Nonspecific binding was blocked with 10% normal goat serum (30-60 minutes). Primary antibodies against Oct-4 were added followed by washing and incubation in secondary fluorescence labeled antibodies. An assay control to confirm staining conditions and to eliminate any nonspecific staining attributed to the MEF present in the cultures was performed using double staining with anti-human nuclear (anti-HuNu) antibody and Oct-4. Cultures were then stained for the presences of alkaline phosphatase (blue) using VECTOR® Blue (VECTOR LABORATORIES®). After the AP color change was complete, the stain was removed and cells were washed and stained with DAPI (fluorescence DNA staining).

When using MA09 cells which have no GFP or another internal marker, we included a control of hESC on MEF only (no RPE) stained for the same markers plus anti-human nuclei. Because hES cells are prone to differentiate without the mutual reinforcement of surrounding hES cells, this control experiment permitted us to determine the upper bound of the number of undifferentiated hES cells that could remain after plating. In these control experiments, the same numbers of hES cells were plated in the same plate area on MEFs in hES cell medium (conditioned hES-GM; see Table 2) but in the absence of RPE cells. The cultures were then stained with an anti-human nuclei (anti-HuNu) antibody to permit detection of the human cells on top of the MEFs and remaining undifferentiated hES cells were counted. These measurements determined how many undifferentiated hES cells would remain when plated in low density but under the best culture conditions (plating in hES medium on MEFs). The number of undifferentiated hES cells detected in these control plates were used as the denominator when calculating the percentage of undifferentiated cells that were detected. When 5 hES cells per 600,000 were introduced as calculated, at least two double-positive were detected. When such low numbers of contaminating cells are introduced, "noise" effects can increase in prominence, as cell loss during manipulations such as pipetting is constant and is not correlated with decreasing percentage of contaminating cells.

Results

As discussed above, a sizeable fraction of hES cells can lose Oct-4 staining during the time course (24 hours) of culture prior to an immunostaining assay. The loss of Oct-4 staining was attributable to maintaining the cultures in RPE growth medium prior to staining. Additional studies confirmed a similar loss of Oct-4 expression in MA09 hES cells during the course of the culturing (approximately 18 hours). Thus, depending on the assay conditions, a percentage of the initially pluripotent hES cells were down-regulated for Oct-4 expression by the time that they were fixed for immunostaining, which would diminish the sensitivity of detection of hES cells in the original cell population.

To minimize the loss of Oct-4 expression, the assay conditions were modified to incorporate the use of MEF feeder cells and hES conditioned growth medium to promote the persistence of hES pluripotent markers during the course of the assay. AP was retained as a primary screening tool because the positive signal (blue cell staining) can be seen in a bright field, allowing the operator to remain in the plane of focus. In contrast, scanning cells for fluorescence requires viewing cells under fluorescent light, which may result in the cells deviating from the plane of focus and may lead to missing a positive signal. In addition, AP staining allows the operator to examine every cell among millions to pinpoint AP positive cells for subsequent examination to confirm Oct-4 expression.

These studies confirmed that this method for detecting rare subpopulations of pluripotent MA09 hES cells in an RPE cell population exhibits exquisite sensitivity.

For each of the two studies reported in this example, all of the cells in 4 to 5 wells of a 6-well plate were first inspected for AP (blue) staining. Any AP positive cell was then re-examined for red fluorescence indicating the presence of Oct-4. Cells were examined for staining using the same scanning method as described in preceding examples (looking for blue-stained cells in the bright field, moving from the top left of the plate in a pattern "right-down-left-down, repeat" until the right-most bottom field had been inspected. In this way, every blue-stained AP positive cell was inspected for Oct-4 (red) staining. The total number of cells inspected per well was determined by counting the number of DAPI stained nuclei in photomicrographs of three randomly selected fields (0.26 mm$^2$/field) and multiplying the mean cells per field by the total number of fields per six-well (960 mm$^2$ per well/0.26 mm$^2$ per field)=3692 fields per six well. Note that each well also contained approximately 500,000 MEF, so a reference well containing only MEF was set up and MEF nuclei were also DAPI stained and counted to obtain accurate numbers of RPE/hES cells excluding MEF. As an alternative, the number of human cells (as opposed to mouse-derived MEFs) counted per well could be determined by counting cells stained with a human-specific marker, such as HuNu.

In these studies, a positive response was defined as a minimum of two double stained cells in RPE preparations spiked at a calculated ratio of 1.6 MA09 hES cells for every 2 million RPE cell. The LOD for detecting contaminating hES is therefore at a level of 0.00008%. Note that this is an order of magnitude more sensitive than that previously reported for the GFP-hES studies. At least two factors account for the enhanced sensitivity 1) the use of MEF and hES conditioned media to retain pluripotency of the hES and 2) increasing the number of cells inspected increases the sensitivity of the assay.

Results of these studies are summarized in Table 9 below.

TABLE 9

2 Million RPE Spiked with a Calculated 1.6 MA09 hES Cells Seeded in Six-Wells with 0.5 Million MEF

|  | Study 1 | Study 2 |
| --- | --- | --- |
| Nuclei/field | 737, 749, 563 | 646, 642, 682 |
| Mean nuclei/field | 683 | 657 |
| Mean Nuclei per Well $^{(a)}$ | 2.52 million | 2.4 million |
| Number of Wells Inspected | 4 | 5 |
| Total Cells Inspected $^{(b)}$ | 10.1 million | 12.1 million |
| Oct-4$^+$ AP$^+$ Positive Cells | 3 | 2 |
| Calculated Total Human Cells Inspected $^{(c)}$ | 8.1 million | 9.6 million |

$^{(a)}$ Mean Nuclei per Field × 3962
$^{(b)}$ Mean Nuclei per Well × Number of Wells Inspected
$^{(c)}$ Total Cells Inspected - MEF contribution (0.5 million × Number of Wells)

In an additional study, two blinded operators examined wells containing 100% RPE cells and RPE cells spiked with 0.0001% hES. All operators identified all the double positive (Oct-4/AP stained) cells in the spiked well whereas no hES staining was observed by any operator in the 100% RPE control.

Example 8

This example describes a further exemplary methods of detecting target cells within a population. Target cells are detected using a first antibody coupled directly or indirectly to Alkaline Phosphatase (AP) and a second antibody coupled to a fluorescent label. This method may be used to detect rare cells of a type that do not express AP (or insufficiently express AP that are insufficient for robust detection). Additionally, this method may be used to detect rare cells that endogenously express AP (e.g., ES cells), in which instance the antibody coupled to AP would be expected to increase AP staining intensity. The first and second antibodies specifically bind to different markers of the rare cell type. For example, where the target cell type is an ES cell, the antibodies specifically bind two different ES cell markers such as alkaline phosphatase, Oct-4, Nanog, Stage-specific embryonic antigen-3 (SSEA-3), Stage-specific embryonic antigen-4 (SSEA-4), TRA-1-60, TRA-1-81, TRA-2-49/6E, Sox2, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (hTERT), SALL4, E-CADHERIN, Cluster designation 30 (CD30), Cripto (TDGF-1), GCTM-2, Genesis, Germ cell nuclear factor, and Stem cell factor (SCF or c-Kit ligand).

Respective coupling of the antibodies to AP and the fluorescent label may be direct or indirect, e.g., through a secondary antibody, actin/biotin affinity, and other methods of indirect coupling. The cells are then stained for alkaline phosphatase activity to permit visualization of cells that bound to the first antibody under visible light. The cell population is then examined under visible light as described in the preceding examples to identify AP-positive cells; AP-positive cells are then examined under ultraviolet light to detect cells that are also labeled by the second antibody. Cells that bound both the first and second antibody are identified as cells of the target type. Optionally, the cell population is plated under conditions that favor growth and/or survival of the target cell type. Optionally, the total number of cells examined is estimated, for example by counting the numbers of cells in random fields and scaling up to the total area counted, and a predetermined minimum number of cells may be examined to ensure a desired level of sensitivity. Where the culture conditions include the presence of feeder cells, counting of the cell population may be performed in the presence of a label that distinguishes the cell population from the feeder cells (e.g., a species-specific antibody or lineage-specific antibody, where the feeder cells are of a different species or type than the cell population), which may be performed in a duplicate well.

Example 9

This example describes a further exemplary methods of detecting target cells within a population. The cell population is stained to detect two different target cell markers using a first and second stain that are visually distinguishable from one another. For example, the cells may be labeled with a first and second antibody, each coupled directly or indirectly to two different enzymes that catalyze reactions that give visible products (e.g., selected from among alkaline phosphatase, beta galactosidase, and a peroxidase such as horse radish peroxidase). The cells are then contacted with substrates of the two different enzymes to catalyze reactions that gives a visible product, wherein the substrates are chosen such that their products are different colors from one another. Alternatively, the products may be the same color as one another but chosen to have distinguishable staining patterns (e.g., one coupled to an antibody that stains nuclei and the other coupled to an antibody that stains the cytoplasmic membrane). As an example, one of the enzymes may be alkaline phosphatase and its substrate may be Vector Red or Vector Blue (producing red and blue products, respectively), and the other enzyme may be a peroxidase and its substrate may be 3,3'-Diaminobenzidine (DAB) (producing a dark brown product). Another exemplary enzyme that may be used is beta galactosidase with the substrate X-Gal (5-Bromo-4-chloro-3-indolyl β-D-galactopyranoside) (producing a blue product) which may readily be used together with peroxidase/DAB (brown product) or AP/Vector Red (red product). Other suitable combinations of enzyme/substrate combinations that produce visually distinguishable products are readily identifiable through routine experimentation. An advantage of this method is that the rare cells may be detected using visible light only without the need for examination under fluorescent light. Additionally, if desired, a further fluorescent label may be utilized (e.g., coupled to an antibody to a third marker) thereby permitting further verification of whether detected cells (i.e., labeled by the first and/or second label) by examination under ultraviolet light.

While the invention has been described by way of examples and preferred embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

Those skilled in the art will recognize, or be able to ascertain using no more than routine experimentation, many equivalents to the specific embodiments of the invention described herein. Such equivalents are intended to be encompassed by the following claims.

Each document cited herein (including all patents, patent applications, and other publications) is hereby incorporated by reference in its entirety to the same extent as if each individual was specifically and individually indicated to be incorporated by reference in its entirety. U.S. Provisional Patent Application Nos. 60/998,766, filed Oct. 12, 2007, 60/998,668, filed Oct. 12, 2007, 61/009,908, filed Jan. 2, 2008, and 61/009,911, filed Jan. 2, 2008, the disclosures of each of the foregoing applications are hereby incorporated by reference in their entirety. In addition, the disclosure of WO 2009/051671 is hereby incorporated by reference in its entirety.

What is claimed is:

1. A method of confirming absence of contaminating pluripotent stem cells in a preparation of differentiated cells generated by differentiation of said pluripotent stem cells, comprising:
   (a) providing a preparation of differentiated cells produced by in vitro differentiation of pluripotent stem cells in a differentiation medium, and culturing said preparation of differentiated cells in a stem cell medium, wherein the stem cell medium maintains pluripotent stem cells in their pluripotent state;
   (b) applying a first stain and a second stain to said preparation of differentiated cells, wherein
      said first stain detects a first embryonic stem cell marker, expression of which is indicative of presence of said contaminating pluripotent stem cells, and
      said second stain detects a second embryonic stem cell marker, expression of which is indicative of presence of said contaminating pluripotent stem cells,
      wherein said first embryonic stem cell marker is different from said second embryonic stem cell marker,
      wherein said first embryonic stem cell maker is alkaline phosphatase; and
   (c) confirming absence of contaminating pluripotent stem cells, if no cells positive for both said first stain and said second stain are identified by microscopic observation.

2. The method of claim 1, wherein said first stain is observable under visible light and said second stain is observable under ultraviolet light.

3. The method of claim 1, wherein said first stain comprises an antibody that specifically binds to said first embryonic stem cell marker.

4. The method of claim 1, wherein said first stain comprises an alkaline phosphatase substrate.

5. The method of claim 1, wherein said second stain comprises a primary antibody that specifically binds to said second embryonic stem cell marker, wherein said primary antibody is directly or indirectly coupled to a fluorescent label.

6. The method of claim 1, wherein said second embryonic stem cell marker is selected from the group consisting of: Oct-4, Nanog, Stage-specific embryonic antigen-3 (SSEA-3), Stage-specific embryonic antigen-4 (SSEA-4), TRA-1-60, TRA-1-81, TRA-2-49/6E, Sox2, and Lin28.

7. The method of claim 1, wherein said preparation of differentiated cells contains at least $10^5$ cells, at least $10^6$ cells, at least $10^7$ cells, at least $10^8$ cells, at least $10^9$ cells, at least $10^{10}$ cells, or between $10^5$ and $10^{10}$ cells.

8. The method of claim 1, wherein said contaminating pluripotent stem cells are embryonic stem cells or induced pluripotent (iPS) cells.

9. The method of claim 1, wherein said preparation of differentiated cells comprises retinal pigment epithelium (RPE) cells differentiated from pluripotent stem cells.

10. The method of claim 9, wherein said RPE cells are human RPE cells.

11. The method of claim 9, wherein said RPE cells are made by a method comprising:
   (a) providing pluripotent stem cells;
   (b) culturing the pluripotent stem cells to form a multilayer population of pluripotent stem cells or embryoid bodies comprising pluripotent stem cells;
   (c) culturing the multilayer population or embryoid bodies in the differentiation medium for a sufficient duration for RPE cells to appear in the culture of cells; and
   (d) isolating the RPE cells from the culture.

12. The method of claim 1, wherein the second embryonic stem cell marker is Nanog.

13. The method of claim 1, wherein the second embryonic stem cell marker is Oct-4.

14. The method of claim 1, wherein said preparation of differentiated cells is cultured on feeder cells.

15. The method of claim 14, wherein said feeder cells are murine embryonic fibroblasts (MEFs) or human adult skin fibroblasts.

16. The method of claim 1, wherein the pluripotent stem cells are human embryonic stem cells or human induced pluripotent stem cells, and the preparation of differentiated cells comprises human RPE cells differentiated in vitro from said pluripotent stem cells.

17. The method of claim 16, wherein the second embryonic cell marker is Oct-4.

18. The method of claim 1, wherein the method detects contaminating pluripotent stem cells that are present at as little as 0.0008% of the preparation of differentiated cells.

19. The method of claim 17, wherein the method detects contaminating pluripotent stem cells that are present at as little as 0.0008% of the preparation of differentiated cells.

20. The method of claim 1, wherein said preparation of differentiated cells is cultured in conditions that comprise leukemia inhibitory factor (LIF).

21. The method of claim 1, wherein the preparation of differentiated cells comprises at least about 95% differentiated RPE cells.

22. The method of claim 1, wherein said first stain and said second stain are visually distinguishable.

* * * * *